(12) United States Patent
Kim et al.

(10) Patent No.: US 10,759,841 B2
(45) Date of Patent: *Sep. 1, 2020

(54) GENE THERAPY FOR DIABETIC NEUROPATHY USING AN HGF ISOFORM

(71) Applicant: Helixmith Co., Ltd., Seoul (KR)

(72) Inventors: Jong Mook Kim, Seoul (KR); Jae Gyun Jeong, Seoul (KR)

(73) Assignee: Helixmith Co., Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/387,587

(22) Filed: Apr. 18, 2019

(65) Prior Publication Data
US 2019/0241632 A1 Aug. 8, 2019

Related U.S. Application Data

(63) Continuation of application No. 15/942,440, filed on Mar. 31, 2018, now abandoned, which is a continuation of application No. 14/355,792, filed as application No. PCT/KR2012/002224 on Mar. 27, 2012, now Pat. No. 9,963,493.

(30) Foreign Application Priority Data

Nov. 3, 2011 (KR) .................. 10-2011-0113786

(51) Int. Cl.
| | | |
|---|---|---|
| C07K 14/475 | (2006.01) | |
| A61K 48/00 | (2006.01) | |
| A61K 38/18 | (2006.01) | |
| A61K 31/711 | (2006.01) | |

(52) U.S. Cl.
CPC ........ *C07K 14/4753* (2013.01); *A61K 31/711* (2013.01); *A61K 38/1833* (2013.01); *A61K 48/005* (2013.01)

(58) Field of Classification Search
None
See application file for complete search history.

(56) References Cited

FOREIGN PATENT DOCUMENTS

| WO | WO 99/36103 A1 | 7/1999 | |
|---|---|---|---|
| WO | WO 2007/142651 A1 | 12/2007 | |
| WO | WO 2009/093880 A2 | 7/2009 | |
| WO | WO-2009093880 A2 * | 7/2009 | ............. A61K 31/70 |

OTHER PUBLICATIONS

Gu et al The Journal of Gene Medicine, 13, 602-610 9 (Year: 2011).*
Ajroud-Driss S, Christiansen M, Allen JA, Kessler JA. Phase 1/2 open-label dose-escalation study of plasmid DNA expressing two isoforms of hepatocyte growth factor in patients with painful diabetic peripheral neuropathy. Mol Ther. 2013;21:1279-1286.
Akita H, Takagi N, Ishihara N, et al. Hepatocyte growth factor improves synaptic localization of the NMDA receptor and intracellular signaling after excitotoxic injury in cultured hippocampal neurons. Exp Neurol. 2008;210:83-94.
Apfel, SC, Schwartz, S, Adornato, BT, Freeman, R, Biton, V, Rendell, M et al. (2000). Efficacy and safety of recombinant human nerve growth factor in patients with diabetic polyneuropathy: A randomized controlled trial. rhNGF Clinical Investigator Group. JAMA 284: 2215-2221.
Bansal et al., "Diabetic neuropathy," Postgrad Med J. 82(964):95-100 (2006).
Bissonette GB, Bae MH, Suresh T, et al. Prefrontal cognitive deficits in mice with altered cerebral cortical GABAergic interneurons. Behav Brain Res. 2014;259:143-151.
Bottaro DP, Rubin JS, Faletto DL, et al. Identification of the hepatocyte growth factor receptor as the c-met proto-oncogene product. Science. 1991;251:802-804.
Bril, V, England, J, Franklin, GM, Backonja, M, Cohen, J, Del Toro, D et al.; American Academy of Neurology; American Association of Neuromuscular and Electrodiagnostic; Medicine; American Academy of Physical Medicine and Rehabilitation. (2011). Evidence-based guideline: Treatment of painful diabetic neuropathy: report of the American Academy of Neurology, the American Association of Neuromuscular and Electrodiagnostic Medicine, and the American Academy of Physical Medicine and Rehabilitation. Neurology 76: 1758-1765.
Bussolino, F, Di Renzo, MF, Ziche, M, Bocchietto, E, Olivero, M, Naldini, L et al. (1992). Hepatocyte growth factor is a potent angiogenic factor which stimulates endothelial cell motility and growth. J Cell Biol 119: 629-641.
Calabrese EJ, Baldwin LA. Hormesis: the dose-response revolution. Annu Rev Pharmacol Toxicol. 2003;43:175-197.
Calabrese EJ. Enhancing and regulating neurite outgrowth. Crit Rev Toxicol. 2008;38:391-418.
Callaghan, BC, Cheng, HT, Stables, CL, Smith, AL and Feldman, EL (2012). Diabetic neuropathy: clinical manifestations and current treatments. Lancet Neurol 11:521-534.
Cameron, NE, Eaton, SE, Cotter, MA and Tesfaye, S (2001). Vascular factors and metabolic interactions in the pathogenesis of diabetic neuropathy. Diabetologia 44:1973-1988.
Canton, A, Burgos, R, Hernandez, C, Mateo, C, Segura, RM, Mesa, J et al. (2000). Hepatocyte growth factor in vitreous and serum from patients with proliferative diabetic retinopathy. Br J Ophthalmol 84: 732-735.
Carlsson, M, Osman, NF, Ursell, PC, Martin, AJ and Saeed, M (2008). Quantitative MR measurements of regional and global left ventricular function and strain after intramyocardial transfer of VM202 into infarcted swine myocardium. Am J Physiol Heart Circ Physiol 295: H522-H532.
Cheng C, Guo GF, Martinez JA, et al. Dynamic plasticity of axons within a cutaneous milieu. J Neurosci. 2010;30:14735-14744.

(Continued)

*Primary Examiner* — Anoop K Singh
(74) *Attorney, Agent, or Firm* — Fenwick & West LLP

(57) ABSTRACT

The present invention relates to a pharmaceutical composition for the prevention or treatment of diabetic neuropathy, wherein the pharmaceutical composition comprises, as active ingredients, different types of isoforms of HGF or a polynucleotide encoding the isoforms. The present invention is the first invention demonstrating that diabetic neuropathy can be prevented and treated using different types of isoforms of HGF. According to the present invention, it is possible to very effectively treat diabetic neuropathy.

2 Claims, 20 Drawing Sheets

Specification includes a Sequence Listing.

(56) References Cited

OTHER PUBLICATIONS

Cho, KR, Choi, JS, Hahn, W, Kim, DS, Park, JS, Lee, DS et al. (2008). Therapeutic angiogenesis using naked DNA expressing two isoforms of the hepatocyte growth factor in a porcine acute myocardial infarction model. Eur J Cardiothorac Surg 34:857-863.
Cleeland CS, Ryan KM. Pain assessment: global use of the Brief Pain Inventory. Ann Acad Med Singapore. 1994;23:129-138 (abstract only).
Davies, M, Brophy, S, Williams, R and Taylor, A (2006). The prevalence, severity, and impact of painful diabetic peripheral neuropathy in type 2 diabetes. Diabetes Care 29:1518-1522.
De Palma Hum Gene Ther. 2003; 14(12): 1193-206.
Dworkin, RH, Turk, DC, Wyrwich, KW, Beaton, D, Cleeland, CS, Farrar, JT et al. (2008). Interpreting the clinical importance of treatment outcomes in chronic pain clinical trials: IMMPACT recommendations. J Pain 9: 105-121.
Ebens, A, Brose, K, Leonardo, ED, Hanson, MG Jr, Bladt, F, Birchmeier, C et al.(1996). Hepatocyte growth factor/scatter factor is an axonal chemoattractant and a neurotrophic factor for spinal motor neurons. Neuron 17: 1157-1172.
Ecke, Goodman & Gilman's The Pharmacological basis of Therapeutics, 1996, McGraw-Hill, New York, NY. pp. 77-101.
Edwards, JL, Vincent, AM, Cheng, HT and Feldman, EL (2008). Diabetic neuropathy: mechanisms to management. Pharmacol Ther 120: 1-34.
Elbaz A, Bower JH, Maraganore DM, et al. Risk tables for parkinsonism and Parkinson's disease. J Clin Epidemiol. 2002;55:25-31.
Funakoshi H, Nakamura T. Identification of HGF-like protein as a novel neurotrophic factor for avian dorsal root ganglion sensory neurons. Biochem Biophys Res Commun. 2001;283:606-612.
Gascon, E, Gaillard, S, Malapert, P, Liu, Y, Rodat-Despoix, L, Samokhvalov, IM et al.(2010). Hepatocyte growth factor-Met signaling is required for Runx1 extinction and peptidergic differentiation in primary nociceptive neurons. J Neurosci 30: 12414-12423.
Gautam et al (Am J Respir Med, 2002;1(1):35-46.
Gille, J, Khalik, M, Konig, V and Kaufmann, R (1998). Hepatocyte growth factor/scatter factor (HGF/SF) induces vascular permeability factor (VPF/VEGF) expression by cultured keratinocytes. J Invest Dermatol 111: 1160-1165.
Gore, M, Brandenburg, NA, Dukes, E, Hoffman, DL, Tai, KS and Stacey, B (2005). Pain severity in diabetic peripheral neuropathy is associated with patient functioning, symptom levels of anxiety and depression, and sleep. J Pain Symptom Manage 30:374-385.
Gu, Y, Zhang, J, Guo, L, Cui, S, Li, X, Ding, D et al. (2011). A phase I clinical study of naked DNA expressing two isoforms of hepatocyte growth factor to treat patients with critical limb ischemia. J Gene Med 13: 602-610.
Hahn, W, Pyun, WB, Kim, DS, Yoo, WS, Lee, SD, Won, JH et al. (2011). Enhanced cardioprotective effects by coexpression of two isoforms of hepatocyte growth factor from naked plasmid DNA in a rat ischemic heart disease model. J Gene Med 13:549-555.
Hashimoto N, Yamanaka H, Fukuoka T, et al. Expression of hepatocyte growth factor in primary sensory neurons of adult rats. Brain Res Mol Brain Res. 2001;97:83-88.
Hashimoto, N, Yamanaka, H, Fukuoka, T, Dai, Y, Obata, K, Mashimo, T et al. (2001). Expression of HGF and cMet in the peripheral nervous system of adult rats following sciatic nerve injury. Neuroreport 12: 1403-1407.
Hebert LE, Weuve J, Scherr PA, Evans DA. Alzheimer disease in the United States (2010-2050) estimated using the 2010 census. Neurology. 2013;80:1778-1783.
Henry, TD, Hirsch, AT, Goldman, J, Wang, YL, Lips, DL, McMillan, WD et al. (2011). Safety of a non-viral plasmid-encoding dual isoforms of hepatocyte growth factor in critical limb ischemia patients: a phase I study. Gene Ther 18: 788-794.
International Search Report for International Application No. PCT/KR2012/002224, dated Oct. 12, 2012 (6 pages).
Jayasankar, V, Woo, YJ, Pirolli, TJ, Bish, LT, Berry, MF, Burdick, J et al. (2005). Induction of angiogenesis and inhibition of apoptosis by hepatocyte growth factor effectively treats postischemic heart failure. J Card Surg 20: 93-101.
Jensen MP, Chodroff MJ, Dworkin RH. The impact of neuropathic pain on health-related quality of life: review and implications. Neurology 2007;68:1178-1182 (abstract only).
Kaiser Science, 317, 2007, 580.
Kato N, Nemoto K, Nakanishi K, et al. Nonviral gene transfer of human hepatocyte growth factor improves streptozotocin-induced diabetic neuropathy in rats. Diabetes. 2005;54:846-854.
Kato N, Nemoto K, Nakanishi K, et al. Nonviral HVJ (hemagglutinating virus of Japan) liposome-mediated retrograde gene transfer of human hepatocyte growth factor into rat nervous system promotes functional and histological recovery of the crushed nerve. Neurosci Res. 2005;52:299-310.
Kay et al Nature Reviews Genetics 12, 316-328, 2011.
Keizer D, Fael D, Wierda JMKH, van Wijhe M. Quantitative sensory testing with Von Frey monofilaments in patients with allodynia: what are we quantifying? Clin J Pain. 2008;24:463-466.
Kim et al., "Development of innovative biomedicine: A case study on cardiovascular gene medicine using naked DNA expressing two isoforms of hepatocyte growth factor," Second workshop of new medicine developer, ViroMed Co. Ltd., published Jun. 1, 2011 (55 pages).
Kim, JS, Hwang, HY, Cho, KR, Park, EA, Lee, W, Paeng, JC et al. (2013). Intramyocardial transfer of hepatocyte growth factor as an adjunct to CABG: phase I clinical study. Gene Ther (doi:10.1038/gt.2012.87).
Koike H, Ishida A, Shimamura M, et al. Prevention of onset of Parkinson's disease by in vivo gene transfer of human hepatocyte growth factor in rodent model: a model of gene therapy for Parkinson's disease. Gene Ther. 2006;13:1639-1644.
Konstorum A, Sprowl SA, Waterman ML, et al. Predicting mechanism of biphasic growth factor action on tumor growth using a multi-species model with feedback control. J Coupled Syst Multiscale Dyn. 2013;1:459-467.
Lee, Y, Park, EJ, Yu, SS, Kim, DK and Kim, S (2000). Improved expression of vascular endothelial growth factor by naked DNA in mouse skeletal muscles: implication for gene therapy of ischemic diseases. Biochem Biophys Res Commun 272: 230-235.
Lin et al., "VEGF and its receptor-2 involved in neuropathic pain transmission mediated by P2X.sub.2/3 receptor of primary sensory neurons," Brain Res Bull. 83(5):284-91 (2010).
Liu, ML, Mars, WM, Zarnegar, R and Michalopoulos, GK (1994). Uptake and distribution of hepatocyte growth factor in normal and regenerating adult rat liver. Am J Pathol 144: 129-140.
Lokker NA, Mark MR, Luis EA, et al. Structure-function analysis of hepatocyte growth factor: identification of variants that lack mitogenic activity yet retain high affinity receptor binding. EMBO J. 1992;11:2503-2510.
Madiai et al., "Anti-fibroblast growth factor-2 antibodies attenuate mechanical allodynia in a rat model of neuropathic pain," J Mol Neurosci 27(3):315-24 (2005), Abstract Only.
Maina, F, Hilton, MC, Andres, R, Wyatt, S, Klein, R and Davies, AM (1998). Multiple roles for hepatocyte growth factor in sympathetic neuron development. Neuron 20:835-846.
Maina, F, Hilton, MC, Ponzetto, C, Davies, AM and Klein, R (1997). Met receptor signaling is required for sensory nerve development and HGF promotes axonal growth and survival of sensory neurons. Genes Dev 11: 3341-3350.
Matsumoto, K and Nakamura, T (1996). Emerging multipotent aspects of hepatocyte growth factor. J Biochem 119: 591-600.
McDowell I. Alzheimer's disease: insights from epidemiology. Aging (Milano) 2001;13:143-162 (abstract only).
Menichella et al., "CXCR4 chemokine receptor signaling mediates pain in diabetic neuropathy," Mol Pain. 10(42):1-13 (2014).
Micheva KD, Taylor CP, Smith SJ. Pregabalin reduces the release of synaptic vesicles from cultured hippocampal neurons. Mol Pharmacol. 2006;70:467-476.
Moghtaderi A, Bakhshipour A, Rashidi H. Validation of Michigan neuropathy screening instrument for diabetic peripheral neuropathy. Clin Neurol Neurosurg. 2006;108:477-481.

(56) References Cited

OTHER PUBLICATIONS

Morishita, R, Aoki, M, Yo, Y and Ogihara, T (2002). Hepatocyte growth factor as cardiovascular hormone: role of HGF in the pathogenesis of cardiovascular disease. Endocr J 49: 273-284.
Nakagami, H, Kaneda, Y, Ogihara, T and Morishita, R (2005). Hepatocyte growth factor as potential cardiovascular therapy. Expert Rev Cardiovasc Ther 3: 513-519 (abstract only).
Ngo et al. in The Protein Folding Problem and Tertiary Structure Prediction, 1994, 491-495.
Nomura M, Oketa Y, Yasui K, et al. Expression of hepatocyte growth factor in the skin of amyotrophic lateral sclerosis. Acta Neurol Scand. 2012;125:389-397.
O'Connor AB. Neuropathic pain: quality-of-life impact, costs and cost effectiveness of therapy. Pharmacoeconomics. 2009;27:95-112 (abstract only).
Perin, EC, Silva, GV, Vela, DC, Zheng, Y, Baimbridge, F, Gahremanpour, A et al. (2011). Human hepatocyte growth factor (VM202) gene therapy via transendocardial injection in a pig model of chronic myocardial ischemia. J Card Fail 17: 601-611.
Pyun et al Gene Therapy , 17, 1442-1452 (Year: 2010).
Pyun, WB, Hahn, W, Kim, DS, Yoo, WS, Lee, SD, Won, JH et al. (2010). Naked DNA expressing two isoforms of hepatocyte growth factor induces collateral artery augmentation in a rabbit model of limb ischemia. Gene Ther 17: 1442-1452.
Romano, Drug News Perspect, 16(5): 267-276, 2003.
Ropper, AH, Gorson, KC, Gooch, CL, Weinberg, DH, Pieczek, A, Ware, JH et al. (2009). Vascular endothelial growth factor gene transfer for diabetic polyneuropathy: a randomized, double-blinded trial. Ann Neurol 65: 386-393.
Russo AJ, Krigsman A, Jepson B, Wakefield A. Decreased serum hepatocyte growth factor (HGF) in autistic children with severe gastrointestinal disease. Biomark Insights. 2009;4:181-190.
Russo AJ, Pietsch SC. Decreased hepatocyte growth factor (HGF) and gamma aminobutyric acid (GABA) in individuals with obsessive-compulsive disorder (OCD) Biomark Insights. 2013;8:107-114.
Saeed, M, Martin, A, Ursell, P, Do, L, Bucknor, M, Higgins, CB et al. (2008). MR assessment of myocardial perfusion, viability, and function after intramyocardial transfer of VM202, a new plasmid human hepatocyte growth factor in ischemic swine myocardium. Radiology 249: 107-118.
Saeed, M, Saloner, D, Do, L, Wilson, M and Martin, A (2011). Cardiovascular magnetic resonance imaging in delivering and evaluating the efficacy of hepatocyte growth factor gene in chronic infarct scar. Cardiovasc Revasc Med 12: 111-122.
Said, G (2007). Diabetic neuropathy—a review. Nat Clin Pract Neurol 3: 331-340.
Shakher, J and Stevens, MJ (2011). Update on the management of diabetic polyneuropathies. Diabetes Metab Syndr Obes 4: 289-305.
Sharma S. Hepatocyte growth factor in synaptic plasticity and Alzheimer's disease. ScientificWorldJournal. 2010;10:457-461.
Shima N, Tsuda E, Goto M, et al. Hepatocyte growth factor and its variant with a deletion of five amino acids are distinguishable in their biological activity and tertiary structure. Biochem Biophys Res Commun. 1994;200:808-815.
Snedecor SJ, Sudharshan L, Cappelleri JC, et al. Systematic review and meta-analysis of pharmacological therapies for painful diabetic peripheral neuropathy. Pain Pract. 2014;14:167-184.
Soofiyani et al Advanced Pharmaceutical Bulletin, 2013, 3(2), 249-255.
Taniyama Y, Morishita R, Aoki M, et al. Therapeutic angiogenesis induced by human hepatocyte growth factor gene in rat and rabbit hindlimb ischemia models: preclinical study for treatment of peripheral arterial disease. Gene Ther. 2001;8:181-189.
Taniyama Y, Morishita R, Hiraoka K, et al. Therapeutic angiogenesis induced by human hepatocyte growth factor gene in rat diabetic hind limb ischemia model: molecular mechanisms of delayed angiogenesis in diabetes. Circulation. 2001;104:2344-2350.
Taylor CP, Angelotti T, Fauman E. Pharmacology and mechanism of action of pregabalin: the calcium channel alpha2-delta (alpha2-delta) subunit as a target for antiepileptic drug discovery. Epilepsy Res. 2007;73:137-150.
Tesfaye, S and Selvarajah, D (2012). Advances in the epidemiology, pathogenesis and management of diabetic peripheral neuropathy. Diabetes Metab Res Rev 28 Suppl 1:8-14.
Tesfaye, S, Vileikyte, L, Rayman, G, Sindrup, S, Perkins, B, Baconja, M et al.; on behalf of the Toronto Expert Panel on Diabetic Neuropathy. (2011). Painful Diabetic Peripheral Neuropathy: Consensus Recommendations on Diagnosis, Assessment and Management. Diabetes Metab Res Rev 27: 629-638.
Thompson J, Dolcet X, Hilton M, et al. HGF promotes survival and growth of maturing sympathetic neurons by PI-3 kinase- and MAP kinase-dependent mechanisms. Mol Cell Neurosci. 2004;27:441-452.
Tolbert et al., PNAS, 2010; 107: 13264-13269.
Tsuchihara, T, Ogata, S, Nemoto, K, Okabayashi, T, Nakanishi, K, Kato, N et al. (2009). Nonviral retrograde gene transfer of human hepatocyte growth factor improves neuropathic pain-related phenomena in rats. Mol Ther 17:42-50.
United States Office Action, U.S. Appl. No. 14/355,792, dated Oct. 5, 2017, 7 pages.
Veves A, Backonja M, Malik RA. Painful diabetic neuropathy: epidemiology, natural history, early diagnosis, and treatment options. Pain Med. 2008;9:660-674.
Vinik AI, Nevoret ML, Casellini C, Parson H. Diabetic neuropathy. Endocrinol Metab Clin North Am. 2013;42:747-787.
Wong, V, Glass, DJ, Arriaga, R, Yancopoulos, GD, Lindsay, RM and Conn, G (1997). Hepatocyte growth factor promotes motor neuron survival and synergizes with ciliary neurotrophic factor. J Biol Chem 272: 5187-5191.
Yang, XM, Toma, JG, Bamji, SX, Belliveau, DJ, Kohn, J, Park, M et al. (1998). Autocrine hepatocyte growth factor provides a local mechanism for promoting axonal growth. J Neurosci 18: 8369-8381.
Zelman, DC, Gore, M, Dukes, E, Tai, KS and Brandenburg, N (2005). Validation of a modified version of the brief pain inventory for painful diabetic peripheral neuropathy. J Pain Symptom Manage 29: 401-410.
Zheng LF, Wang R, Yu QP, et al. Expression of HGF/c-Met is dynamically regulated in the dorsal root ganglions and spinal cord of adult rats following sciatic nerve ligation. Neurosignals. 2010;18:49-56.
United States Office Action, U.S. Appl. No. 15/942,440, dated Jun. 1, 2018, 11 pages.

\* cited by examiner

SEQUENCE LISTING

<160> NUMBER OF SEQ ID NOS: 16

<210> SEQ ID NO 1
<211> LENGTH: 728
<212> TYPE: PRT
<213> ORGANISM: Artificial Sequence
<220> FEATURE:
<223> OTHER INFORMATION: amino acid sequence of flHGF

<400> SEQUENCE: 1

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
```

```
                355                 360                 365
Asp Pro Asn Ile Arg Val Gly Tyr Cys Ser Gln Ile Pro Asn Cys Asp
370                 375                 380
Met Ser His Gly Gln Asp Cys Tyr Arg Gly Asn Gly Lys Asn Tyr Met
385                 390                 395                 400
Gly Asn Leu Ser Gln Thr Arg Ser Gly Leu Thr Cys Ser Met Trp Asp
                405                 410                 415
Lys Asn Met Glu Asp Leu His Arg His Ile Phe Trp Glu Pro Asp Ala
            420                 425                 430
Ser Lys Leu Asn Glu Asn Tyr Cys Arg Asn Pro Asp Asp Ala His
        435                 440                 445
Gly Pro Trp Cys Tyr Thr Gly Asn Pro Leu Ile Pro Trp Asp Tyr Cys
    450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
Asn Gly Ile Pro Thr Arg Thr Asn Ile Gly Trp Met Val Ser Leu Arg
            500                 505                 510
Tyr Arg Asn Lys His Ile Cys Gly Gly Ser Leu Ile Lys Glu Ser Trp
        515                 520                 525
Val Leu Thr Ala Arg Gln Cys Phe Pro Ser Arg Asp Leu Lys Asp Tyr
    530                 535                 540
Glu Ala Trp Leu Gly Ile His Asp Val His Gly Arg Gly Asp Glu Lys
545                 550                 555                 560
Cys Lys Gln Val Leu Asn Val Ser Gln Leu Val Tyr Gly Pro Glu Gly
                565                 570                 575
Ser Asp Leu Val Leu Met Lys Leu Ala Arg Pro Ala Val Leu Asp Asp
            580                 585                 590
Phe Val Ser Thr Ile Asp Leu Pro Asn Tyr Gly Cys Thr Ile Pro Glu
        595                 600                 605
Lys Thr Ser Cys Ser Val Tyr Gly Trp Gly Tyr Thr Gly Leu Ile Asn
    610                 615                 620
Tyr Asp Gly Leu Leu Arg Val Ala His Leu Tyr Ile Met Gly Asn Glu
625                 630                 635                 640
Lys Cys Ser Gln His His Arg Gly Lys Val Thr Leu Asn Glu Ser Glu
                645                 650                 655
Ile Cys Ala Gly Ala Glu Lys Ile Gly Ser Gly Pro Cys Glu Gly Asp
            660                 665                 670
Tyr Gly Gly Pro Leu Val Cys Glu Gln His Lys Met Arg Met Val Leu
        675                 680                 685
Gly Val Ile Val Pro Gly Arg Gly Cys Ala Ile Pro Asn Arg Pro Gly
    690                 695                 700
Ile Phe Val Arg Val Ala Tyr Tyr Ala Lys Trp Ile His Lys Ile Ile
705                 710                 715                 720
Leu Thr Tyr Lys Val Pro Gln Ser
                725

<210> SEQ ID NO 2
<211> LENGTH: 723
<212> TYPE: PRT
<213> ORGANISM: Artificial Sequence
<220> FEATURE:
<223> OTHER INFORMATION: amino acid sequence of dHGF
```

```
<400> SEQUENCE: 2

Met Trp Val Thr Lys Leu Leu Pro Ala Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
                180                 185                 190

Tyr Glu Val Cys Asp Ile Pro Gln Cys Ser Glu Val Glu Cys Met Thr
            195                 200                 205

Cys Asn Gly Glu Ser Tyr Arg Gly Leu Met Asp His Thr Glu Ser Gly
    210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
            260                 265                 270

Thr Arg Trp Glu Tyr Cys Ala Ile Lys Thr Cys Ala Asp Asn Thr Met
    275                 280                 285

Asn Asp Thr Asp Val Pro Leu Glu Thr Thr Glu Cys Ile Gln Gly Gln
290                 295                 300

Gly Glu Gly Tyr Arg Gly Thr Val Asn Thr Ile Trp Asn Gly Ile Pro
305                 310                 315                 320

Cys Gln Arg Trp Asp Ser Gln Tyr Pro His Glu His Asp Met Thr Pro
                325                 330                 335

Glu Asn Phe Lys Cys Lys Asp Leu Arg Glu Asn Tyr Cys Arg Asn Pro
            340                 345                 350

Asp Gly Ser Glu Ser Pro Trp Cys Phe Thr Thr Asp Pro Asn Ile Arg
    355                 360                 365

Val Gly Tyr Cys Ser Gln Ile Pro Asn Cys Asp Met Ser His Gly Gln
370                 375                 380

Asp Cys Tyr Arg Gly Asn Gly Lys Asn Tyr Met Gly Asn Leu Ser Gln
385                 390                 395                 400

Thr Arg Ser Gly Leu Thr Cys Ser Met Trp Asp Lys Asn Met Glu Asp
                405                 410                 415
```

Leu His Arg His Ile Phe Trp Glu Pro Asp Ala Ser Lys Leu Asn Glu
            420                 425                 430

Asn Tyr Cys Arg Asn Pro Asp Asp Ala His Gly Pro Trp Cys Tyr
            435                 440                 445

Thr Gly Asn Pro Leu Ile Pro Trp Asp Tyr Cys Pro Ile Ser Arg Cys
450                 455                 460

Glu Gly Asp Thr Thr Pro Thr Ile Val Asn Leu Asp His Pro Val Ile
465                 470                 475                 480

Ser Cys Ala Lys Thr Lys Gln Leu Arg Val Val Asn Gly Ile Pro Thr
            485                 490                 495

Arg Thr Asn Ile Gly Trp Met Val Ser Leu Arg Tyr Arg Asn Lys His
            500                 505                 510

Ile Cys Gly Gly Ser Leu Ile Lys Glu Ser Trp Val Leu Thr Ala Arg
            515                 520                 525

Gln Cys Phe Pro Ser Arg Asp Leu Lys Asp Tyr Glu Ala Trp Leu Gly
            530                 535                 540

Ile His Asp Val His Gly Arg Gly Asp Glu Lys Cys Lys Gln Val Leu
545                 550                 555                 560

Asn Val Ser Gln Leu Val Tyr Gly Pro Glu Gly Ser Asp Leu Val Leu
            565                 570                 575

Met Lys Leu Ala Arg Pro Ala Val Leu Asp Asp Phe Val Ser Thr Ile
            580                 585                 590

Asp Leu Pro Asn Tyr Gly Cys Thr Ile Pro Glu Lys Thr Ser Cys Ser
            595                 600                 605

Val Tyr Gly Trp Gly Tyr Thr Gly Leu Ile Asn Tyr Asp Gly Leu Leu
            610                 615                 620

Arg Val Ala His Leu Tyr Ile Met Gly Asn Glu Lys Cys Ser Gln His
625                 630                 635                 640

His Arg Gly Lys Val Thr Leu Asn Glu Ser Glu Ile Cys Ala Gly Ala
            645                 650                 655

Glu Lys Ile Gly Ser Gly Pro Cys Glu Gly Asp Tyr Gly Gly Pro Leu
            660                 665                 670

Val Cys Glu Gln His Lys Met Arg Met Val Leu Gly Val Ile Val Pro
            675                 680                 685

Gly Arg Gly Cys Ala Ile Pro Asn Arg Pro Gly Ile Phe Val Arg Val
            690                 695                 700

Ala Tyr Tyr Ala Lys Trp Ile His Lys Ile Ile Leu Thr Tyr Lys Val
705                 710                 715                 720

Pro Gln Ser

<210> SEQ ID NO 3
<211> LENGTH: 207
<212> TYPE: PRT
<213> ORGANISM: Artificial Sequence
<220> FEATURE:
<223> OTHER INFORMATION: amino acid sequence of NK1

<400> SEQUENCE: 3

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
         50                  55                  60

Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
                115                 120                 125

Ile Ile Gly Lys Gly Arg Ser Tyr Lys Gly Thr Val Ser Ile Thr Lys
        130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
                180                 185                 190

Asn Pro Glu Val Arg Tyr Glu Val Cys Asp Ile Pro Gln Cys Ser
                195                 200                 205

<210> SEQ ID NO 4
<211> LENGTH: 290
<212> TYPE: PRT
<213> ORGANISM: Artificial Sequence
<220> FEATURE:
<223> OTHER INFORMATION: amino acid sequence of NK2

<400> SEQUENCE: 4

Met Trp Val Thr Lys Leu Leu Pro Ala Leu Leu Leu Gln His Val Leu
 1               5                  10                  15

Leu His Leu Leu Leu Leu Pro Ile Ala Ile Pro Tyr Ala Glu Gly Gln
                 20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
         50                  55                  60

Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
                115                 120                 125

Ile Ile Gly Lys Gly Arg Ser Tyr Lys Gly Thr Val Ser Ile Thr Lys
        130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
                180                 185                 190

Asn Pro Glu Val Arg Tyr Glu Val Cys Asp Ile Pro Gln Cys Ser Glu
                195                 200                 205

```
Val Glu Cys Met Thr Cys Asn Gly Glu Ser Tyr Arg Gly Leu Met Asp
    210                 215                 220
His Thr Glu Ser Gly Lys Ile Cys Gln Arg Trp Asp His Gln Thr Pro
225                 230                 235                 240
His Arg His Lys Phe Leu Pro Glu Arg Tyr Pro Asp Lys Gly Phe Asp
                245                 250                 255
Asp Asn Tyr Cys Arg Asn Pro Asp Gly Gln Pro Arg Pro Trp Cys Tyr
                260                 265                 270
Thr Leu Asp Pro His Thr Arg Trp Glu Tyr Cys Ala Ile Lys Thr Cys
            275                 280                 285
Glu Thr
    290

<210> SEQ ID NO 5
<211> LENGTH: 470
<212> TYPE: PRT
<213> ORGANISM: Artificial Sequence
<220> FEATURE:
<223> OTHER INFORMATION: amino acid sequence of NK4

<400> SEQUENCE: 5

Met Trp Val Thr Lys Leu Leu Pro Ala Leu Leu Leu Gln His Val Leu
1               5                   10                  15
Leu His Leu Leu Leu Leu Pro Ile Ala Ile Pro Tyr Ala Glu Gly Gln
                20                  25                  30
Arg Lys Arg Arg Asn Thr Ile His Glu Phe Lys Lys Ser Ala Lys Thr
            35                  40                  45
Thr Leu Ile Lys Ile Asp Pro Ala Leu Lys Ile Lys Thr Lys Lys Val
    50                  55                  60
Asn Thr Ala Asp Gln Cys Ala Asn Arg Cys Thr Arg Asn Lys Gly Leu
65                  70                  75                  80
Pro Phe Thr Cys Lys Ala Phe Val Phe Asp Lys Ala Arg Lys Gln Cys
                85                  90                  95
Leu Trp Phe Pro Phe Asn Ser Met Ser Ser Gly Val Lys Lys Glu Phe
                100                 105                 110
Gly His Glu Phe Asp Leu Tyr Glu Asn Lys Asp Tyr Ile Arg Asn Cys
            115                 120                 125
Ile Ile Gly Lys Gly Arg Ser Tyr Lys Gly Thr Val Ser Ile Thr Lys
    130                 135                 140
Ser Gly Ile Lys Cys Gln Pro Trp Ser Ser Met Ile Pro His Glu His
145                 150                 155                 160
Ser Phe Leu Pro Ser Ser Tyr Arg Gly Lys Asp Leu Gln Glu Asn Tyr
                165                 170                 175
Cys Arg Asn Pro Arg Gly Glu Glu Gly Gly Pro Trp Cys Phe Thr Ser
            180                 185                 190
Asn Pro Glu Val Arg Tyr Glu Val Cys Asp Ile Pro Gln Cys Ser Glu
    195                 200                 205
Val Glu Cys Met Thr Cys Asn Gly Glu Ser Tyr Arg Gly Leu Met Asp
    210                 215                 220
His Thr Glu Ser Gly Lys Ile Cys Gln Arg Trp Asp His Gln Thr Pro
225                 230                 235                 240
His Arg His Lys Phe Leu Pro Glu Arg Tyr Pro Asp Lys Gly Phe Asp
                245                 250                 255
Asp Asn Tyr Cys Arg Asn Pro Asp Gly Gln Pro Arg Pro Trp Cys Tyr
                260                 265                 270
```

Thr Leu Asp Pro His Thr Arg Trp Glu Tyr Cys Ala Ile Lys Thr Cys
            275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu
465                 470

<210> SEQ ID NO 6
<211> LENGTH: 2187
<212> TYPE: DNA
<213> ORGANISM: Artificial Sequence
<220> FEATURE:
<223> OTHER INFORMATION: nucleotide sequence of cHGF

<400> SEQUENCE: 6
atgtgggtga ccaaactcct gccagccctg ctgctgcagc atgtcctcct gcatctcctc        60
ctgctcccca tcgccatccc ctatgcagag ggacaaagga aagaagaaa tacaattcat       120 gaattcaaaa aatcagcaaa gactacccta atcaaaatag atccagcact gaagataaaa       180
accaaaaaag tgaatactgc agaccaatgt gctaatagat gtactaggaa taaaggactt       240
ccattcactt gcaaggcttt tgttttgat aaagcaagaa acaatgcct ctggttcccc       300 ttcaatagca tgtcaagtgg agtgaaaaaa gaatttggcc atgaatttga cctctatgaa       360
aacaaagact acattagaaa ctgcatcatt ggtaaaggac gcagctacaa gggaacagta       420
tctatcacta gagtggcat caaatgtcag ccctggagtt ccatgatacc acacgaacac       480 agcttttgc cttcgagcta tcggggtaaa gacctacagg aaactactg tcgaaatcct       540 cgagggaag aaggggggacc ctggtgttc acaagcaatc agaggtacg ctacgaagtc       600 tgtgacattc ctcagtgttc agaagttgaa tgcatgacct gcaatgggga gagttatcga       660
ggtctcatga tcatacaga tcaggcaag atttgtcagc ctgggatca tcagacacca       720 caccggcaca aattcttgcc tgaaagatat ccgacaagg ctttgatga taattattgc       780 cgcaatcccg atggccagcc gaggccatgt gctatactc ttgaccctca caccgctgg       840 gagtactgtg caattaaaac atgcgctgac aatactatga atgacactga tgttcctttg       900

| | |
|---|---|
| gaaacaactg aatgcatcca aggtcaagga aaggctaca ggggcactgt caataccatt | 960 |
| tggaatggaa ttccatgtca gcgttgggat tctcagtatc ctcacagca tgacatgact | 1020 |
| cctgaaaatt tcaagtgcaa ggacctacga gaaaattact gccgaaatcc agatgggtct | 1080 |
| gaatcaccct ggtgttttac cactgatcca aacatccgag ttggctactg ctcccaaatt | 1140 |
| ccaaactgtg atatgtcaca tggacaagat tgttatcgtg gaatggcaa aaattatatg | 1200 |
| ggcaacttat cccaaacaag atctggacta acatgttcaa tgtgggacaa gaacatggaa | 1260 |
| gacttacatc gtcatatctt ctgggaacca gatgcaagta agctgaatga gaattactgc | 1320 |
| cgaaatccag atgatgatgc tcatggaccc tggtgctaca cgggaaatcc actcattcct | 1380 |
| tgggattatt gccctatttc tcgttgtgaa ggtgatacca cacctacaat agtcaattta | 1440 |
| gaccatcccg taatatcttg tgccaaaacg aaacaattgc gagttgtaaa tgggattcca | 1500 |
| acacgaacaa acataggatg gatggttagt ttgagataca gaaataaaca tatctgcgga | 1560 |
| ggatcattga taaggagag ttgggttctt actgcacgac agtgtttccc ttctcgagac | 1620 |
| ttgaaagatt atgaagcttg gcttggaatt catgatgtcc acggaagagg agatgagaaa | 1680 |
| tgcaaacagg ttctcaatgt tcccagctg gtatatggcc ctgaaggatc agatctggtt | 1740 |
| ttaatgaagc ttgccaggcc tgctgtcctg atgatttttg ttagtacgat tgatttacct | 1800 |
| aattatggat gcacaattcc tgaaaagacc agttgcagtg tttatggctg gggctacact | 1860 |
| ggattgatca actatgatgg cctattacga gtggcacatc tctatataat gggaaatgag | 1920 |
| aaatgcagcc agcatcatcg agggaaggtg actctgaatg agtctgaaat atgtgctggg | 1980 |
| gctgaaaaga ttgatcagg accatgtgag ggggattatg tggcccact tgtttgtgag | 2040 |
| caacataaaa tgagaatggt tcttggtgtc attgttcctg gtcgtggatg tgccattcca | 2100 |
| aatcgtcctg gtatttttgt ccagtagca tattatgcaa aatggataca caaaattatt | 2160 |
| ttaacatata aggtaccaca gtcatag | 2187 |

<210> SEQ ID NO 7
<211> LENGTH: 7113
<212> TYPE: DNA
<213> ORGANISM: Artificial Sequence
<220> FEATURE:
<223> OTHER INFORMATION: nucleotide sequence of hybrid HGF

<400> SEQUENCE: 7

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aagaagaaa tacaattcat | 120 |
| gaattcaaaa atcagcaaa gactacccta atcaaaatag atccagcact gaagataaaa | 180 |
| accaaaaaag tgaatactgc agaccaatgt gctaatagat gtactaggaa taaaggactt | 240 |
| ccattcactt gcaaggcttt tgttttgat aaagcaagaa acaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatt ggtaaaggac gcagctacaa gggaacagta | 420 |
| tctatcacta gagtggcat caaatgtcag ccctggagtt ccatgatacc acacgaacac | 480 |
| aggtaagaac agtatgaaga aaagagatga agcctctgtc ttttttacat gttaacagtc | 540 |
| tcatattagt ccttcagaat aattctacaa tcctaaaata acttagccaa cttgctgaat | 600 |
| tgtattacgg caaggtttat atgaattcat gactgatatt tagcaaatga ttaattaata | 660 |
| tgttaataaa atgtagccaa aacaatatct taccttaatg cctcaatttg tagatctcgg | 720 |
| tatttgtgaa ataataacgt aaacttcgtt taaaaggatt cttcttcctg tctttgagaa | 780 |

```
agtacggcac tgtgcagggg gagaggttga ttgtgaaaaa tcagaggtag atgagaatct      840
tactgagggc tgagggttct ttaaccttgg tggatctcaa cattggttgc acattaaaat      900
cacctgctgc aagcccttga cgaatcttac ttagaagatg acaacacaga acaattaaat      960
cagaatctct ggggagaata gggcaccagt attttttgag ctcccaccat gattccaaag     1020
tgcagccaaa tttgagaacc actgctaaaa gctcaagctt cagattgacc agcttttcca     1080
tctcacctat cgcctaaaga ccaaattgga taaatgtgtt cattacgaca gatgggtact     1140
atttaaagat gagtaaacac aatatactta ggctcgtcag actgagagtt ttaatcatca     1200
ctgaggaaaa acatagatat ctaatactga ctggagtatt agtcaaggct tatttcacac     1260
acaattttat cagaaaccaa agtagtttaa aacagctctc cccttattag taatgcattg     1320
gagggtttac tttaccatgt accttgctga gcactgtacc ttgttaatct catttacttg     1380
taatgagaac cacacagcgg gtagttttat tggttctatt ttacctacat gacaaaactg     1440
aagcataaaa acacttagta agttttcagt gtcatgcaca actaggaagt gacatggcca     1500
gaatataagc ccagtcacca tcactctata acctgcgctt taacaacttc agggcatga     1560 cacatttggc cggtcagtag aacccatgct gtgatttgtt tttgcagtgg tggtgatgac     1620
tgccttgttg aatccacttt ttattctatt ccattttggg gacacaattc tgcaagatga     1680
ttcttcatta ggaaacagag atgagttatt gaccaacaca gaaagaaaaa gagtttgttg     1740
ctccacactg ggattaaacc tatgatcttg gcctaattaa cactagctag taagtgtcca     1800
agctgatcat ctctcaaaca tttcaataac agaaaacaac aattttcaaa attagttact     1860
tacaattatg tagaaatgcc tctaaaacac agtatttttcc ttatattaca aaacaaaaa     1920 ttataattgg ttttgtcctc ttttgagagt ttgcatggtg ttactccctg catagtgaag     1980
aaaacatttt atttaagtag atggatctaa gttttttcatg aacaaaggaa tgacatttga     2040
aatcaatcct accctagtcc aggagaatgc attagattaa cctagtagag gtcttatttc     2100
accctgagtt ttctatgatc gtgattctct gctggaggag taattgtgaa atagatctct     2160
ctgggaactg gcttcctagt ccaatcagct cttttaccaa tgaacacttc cttgtgatat     2220
agatgtttat ggccgagagg atccagtata ttaataaaat ccctttttgt attcaatgag     2280
ggaaacacat aattttcatc aattagcagc ttattggaat atctgcatga tggtttaaca     2340
cttttaagtg ttgactaaag attaattta cagaaaatag aaaagaaat atgtttctgt     2400 ctggaggaat gatttattgt tgaccctaa attgaaatat tttactagtg cttaatgga     2460 aagatgatga aagatgatga aattaatgta gaagcttaac tagaaaatca ggtgacctga     2520
tatctacatc tgtatccttc attggccacc cagcattcat taatgaatca gatgatggaa     2580
tagatcaagt ttcctaggaa cacagtgaat attaaaagaa aacaagggga gcctagcacc     2640
tagaagacct agtttatatt tcaaagtata tttggatgta acccaatttt aaacatttcc     2700
tcacttgtct ctcttaaagc cttgccaaca gcaaggacga agaaccaaaa atagtgtata     2760
tatgaataaa tgcttattac agaatctgct gactggcaca tgctttgtgt gtaatgggtt     2820
ctcataaaca cttgttgaat gaacacacat aagtgaaaga gcatggctag gcttcatccc     2880
ttggtcaaat atgggtgct aaagaaaagc aggggaaata cattgggaca ctaacaaaaa     2940
aaaacagtta atttaggtaa aagataaaat acaccacaga atgaagaaaa gagatgaccc     3000
agactgctct ttaaccttca tgtcctagag aggttttga tatgaattgc attcagaatt     3060
gtggaaagga gcccatcttt tctcttcatt ttgatttat taactccaat ggggggaattt     3120
```

```
tattcgtgtt ttggccatat ctactttga tttctacatt attctctctt cctttctacc    3180
tgtatttgtc ctaataaatt gttgacttat taattcacta cttcctcaca gcttttttt    3240
ggctttacaa atccactgga aaggtatatg ggtgtatcac tttgtgtatt tcggtgtgca    3300
tgtgtagagg ggacaaaaat cctctctcaa actataaata ttgagtattt gtgtattgaa    3360
catttgctat aactactagg tttcttaaat aatcttaata tataaaatga tatagaaaaa    3420
gggaaattat agttcgtatt attcatctaa gtgaagagat taaaacccag ggagtaaata    3480
aattgtctaa ggactaaggt tgtatactat ttaggtgata gatatggggc aaccgtatgg    3540
gttttatgat taacaaataa acttctcacc actctaccat atcaactttt ccataaaaga    3600
gagctatagt attctttgct taaataaatt tgattagtgc atgacttctt gaaaacatat    3660
aaagcaaaag tcacatttga ttctatcaga aaagtgagta agccatggcc caaacaaaag    3720
atgcattaaa atattctgga atgatggagc taaaagtaag aaaaatgact ttttaaaaaa    3780
gtttactgtt aggaattgtg aaattatgct gaatttagt tgcattataa ttttgtcag    3840
tcatacggtc tgacaacctg tcttatttct atttccccat atgaggaatg ctagttaagt    3900
atggatatta actattacta cttagatgca ttgaagttgc ataatatgga taatacttca    3960
ctggttccct gaaaatgttt agttagtaat aagtctctta cactatttgt tttgtccaat    4020
aatttatatt ttctgaagac ttaactctag aatacactca tgtcaaaatg aaagaatttc    4080
attgcaaaat attgcttggt acatgacgca tacctgtatt tgttttgtgt cacaacatga    4140
aaaatgatgg tttattagaa gtttcattgg gtaggaaaca catttgaatg gtatttacta    4200
agatactaaa atccttggac ttcactctaa ttttagtgcc atttagaact caaggtctca    4260
gtaaaagtag aaataaagcc tgttaacaaa acacaagctg aatattaaaa atgtaactgg    4320
atttcaaag aaatgtttac tggtattacc tgtagatgta tattctttat tatgatcttt    4380
tgtgtaaagt ctggcagaca aatgcaatat ctaattgttg agtccaatat cacaagcagt    4440
acaaagtat aaaaaagact tggccttttc taatgtgtta aaatacttta tgctggtaat    4500
aacactaaga gtagggcact agaaatttta agtgaagata atgtgttgca gttactgcac    4560
tcaatggctt actattataa accaaaactg ggatcactaa gctccagtca gtcaaaatga    4620
tcaaaattat tgaagagaat aagcaattct gttctttatt aggacacagt agatacagac    4680
tacaaagtgg agtgtgctta ataagaggta gcatttgtta agtgtcaatt actctattat    4740
cccttggagc ttctcaaaat aaccatataa ggtgtaagat gttaaaggtt atggttacac    4800
tcagtgcaca ggtaagctaa taggctgaga gaagctaaat tacttactgg ggtctcacag    4860
taagaaagtg agctgaagtt tcagcccaga tttaactgga ttctgggctc tttattcatg    4920
ttacttcatg aatctgtttc tcaattgtgc agaaaaaagg gggctattta taagaaaagc    4980
aataaacaaa caagtaatga tctcaaataa gtaatgcaag aaatagtgag atttcaaaat    5040
cagtggcagc gatttctcag ttctgtccta agtggccttg ctcaatcacc tgctatcttt    5100
tagtggagct ttgaaattat gtttcagaca acttcgattc agttctagaa tgtttgactc    5160
agcaaattca caggctcatc tttctaactt gatggtgaat atggaaattc agctaaatgg    5220
atgttaataa aattcaaacg ttttaaggac agatgaaaat gacagaattt taaggtaaaa    5280
tatatgaagg aatataagat aaaggatttt tctaccttca gcaaaaacat acccactaat    5340
tagtaaaatt aataggcaaa aaaagttgc atgctcttat actgtaatga ttatcatttt    5400
aaaactagct ttttgccttc gagctatcgg ggtaaagacc tacaggaaaa ctactgtcga    5460
aatcctcgag gggaagaagg gggaccctgg tgtttcacaa gcaatccaga ggtacgctac    5520
```

```
gaagtctgtg acattcctca gtgttcagaa gttgaatgca tgacctgcaa tggggagagt    5580
tatcgaggtc tcatggatca tacagaatca ggcaagattt gtcagcgctg ggatcatcag    5640
acaccacacc ggcacaaatt cttgcctgaa agatatcccg acaagggctt tgatgataat    5700
tattgccgca atcccgatgg ccagccgagg ccatggtgct atactcttga ccctcacacc    5760
cgctgggagt actgtgcaat taaaacatgc gctgacaata ctatgaatga cactgatgtt    5820
cctttggaaa caactgaatg catccaaggt caaggagaag gctacagggg cactgtcaat    5880
accatttgga atggaattcc atgtcagcgt tgggattctc agtatcctca cgagcatgac    5940
atgactcctg aaaatttcaa gtgcaaggac ctacgagaaa attactgccg aaatccagat    6000
gggtctgaat caccctggtg ttttaccact gatccaaaca tccgagttgg ctactgctcc    6060
caaattccaa actgtgatat gtcacatgga caagattgtt atcgtgggaa tggcaaaaat    6120
tatatgggca acttatccca aacaagatct ggactaacat gttcaatgtg gacaagaac     6180 atggaagact acatcgtcta tatcttctgg gaaccagatg caagtaagct gaatgagaat    6240
tactgccgaa atccagatga tgatgctcat ggaccctggt gctacacggg aaatccactc    6300
attccttggg attattgccc tatttctcgt tgtgaaggtg ataccacacc tacaatagtc    6360
aatttagacc atcccgtaat atcttgtgcc aaaacgaaac aattgcgagt tgtaaatggg    6420
attccaacac gaacaaacat aggatggatg gttagtttga gatacagaaa taaacatatc    6480
tgcggaggat cattgataaa ggagagttgg gttcttactg cacgacagtg tttcccttct    6540
cgagacttga aagattatga agcttggctt ggaattcatg atgtccacgg aagaggagat    6600
gagaaatgca acaggttcct caatgttccc cagctggtat atggccctga aggatcagat    6660
ctggttttaa tgaagcttgc caggcctgct gtcctggatg attttgttag tacgattgat    6720
ttacctaatt atggatgcac aattcctgaa aagaccagtt gcagtgttta tggctggggc    6780
tacactggat tgatcaacta tgatggccta ttacgagtgg cacatctcta tataatggga    6840
aatgagaaat gcagccagca tcatcgaggg aaggtgactc tgaatgagtc tgaaatatgt    6900
gctggggctg aaaagattgg atcaggacca tgtgaggggg attatggtgg cccacttgtt    6960
tgtgagcaac ataaaatgag aatggttctt ggtgtcattg ttcctggtcg tggatgtgcc    7020
attccaaatc gtcctggtat ttttgtccga gtagcatatt atgcaaaatg gatacacaaa    7080
attattttaa catataaggt accacagtca tag                                 7113
```

<210> SEQ ID NO 8
<211> LENGTH: 6190
<212> TYPE: DNA
<213> ORGANISM: Artificial Sequence
<220> FEATURE:
<223> OTHER INFORMATION: nucleotide sequence of HGF-X2

<400> SEQUENCE: 8

```
atgtgggtga ccaaactcct gccagccctg ctgctgcagc atgtcctcct gcatctcctc      60
ctgctcccca tcgccatccc ctatgcagag ggacaaagga aagaagaaa tacaattcat     120 gaattcaaaa aatcagcaaa gactacccta atcaaaatag atccagcact gaagataaaa     180
accaaaaaag tgaatactgc agaccaatgt gctaatagat gtactaggaa taaggactt      240 ccattcactt gcaaggcttt tgtttttgat aaagcaagaa acaatgcct ctggttcccc      300 ttcaatgca tgtcaagtgg agtgaaaaaa gaatttggcc atgaatttga cctctatgaa      360
aacaaagact acattagaaa ctgcatcatt ggtaaaggac gcagctacaa gggaacagta     420
```

```
tctatcacta agagtggcat caaatgtcag ccctggagtt ccatgatacc acacgaacac      480
aggtaagaac agtatgaaga aaagagatga agcctctgtc ttttttacat gttaacagtc      540
tcatattagt ccttcagaat aattctacaa tcctaaaata acttagccaa cttgctgaat      600
tgtattacgg caaggtttat atgaattcat gactgatatt tagcaaatga ttaattaata      660
tgttaataaa atgtagccaa acaatatctt taccttaatg cctcaatttg tagatctcgg      720
tatttgtgaa ataataacgt aaacttcgtt taaaaggatt cttcttcctg tctttgagaa      780
agtacggcac tgtgcagggg gagaggttga ttgtgaaaaa tcagaggtag atgagaatct      840
tactgagggc tgagggttct ttaaccttgg tggatctcaa cattggttgc acattaaaat      900
cacctgctgc aagcccttga cgaatcttac ttagaagatg acaacacaga acaattaaat      960
cagaatctct ggggagaata gggcaccagt attttttgag ctcccaccat gattccaaag     1020
tgcagccaaa tttgagaacc actgctaaaa gctcaagctt cagattgacc agcttttcca     1080
tctcacctat cgcctaaaga ccaaattgga taaatgtgtt cattacgaca gatgggtact     1140
atttaaagat gagtaaacac aatatactta ggctcgtcag actgagagtt ttaatcatca     1200
ctgaggaaaa acatagatat ctaatactga ctggagtatt agtcaaggct tatttcacac     1260
acaattttat cagaaaccaa agtagttaaa aacagctctc cccttattag taatgcattg     1320
gagggtttac tttaccatgt accttgctga gcactgtacc ttgttaatct catttacttg     1380
taatgagaac cacacagcgg gtagtttatt tggttctatt ttacctacat gacaaaactg     1440
aagcataaaa acacttagta agttttcagt gtcatgcaca actaggaagt gacatggcca     1500
gaatataagc ccagtcacca tcactctata acctgcgctt ttaacaactt cagggcatga     1560
cacatttggc cggtcagtag aacccatgct gtgatttgtt tttgcagtgg tggtgatgac     1620
tgccttgttg aatccacttt ttattctatt ccattttggg gacacaattc tgcaagatga     1680
ttcttcatta ggaaacagag atgagttatt gaccaacaca gaaagaaaaa gagtttgttg     1740
ctccacactg ggattaaacc tatgatcttg gcctaattaa cactagctag taagtgtcca     1800
agctgatcat ctctacaaca tttcaataac agaaaacaac aattttcaaa attagttact     1860
tacaattatg tagaaatgcc tctaaaacac agtattttcc ttatattaca aaaacaaaaa     1920
ttataattgg ttttgtcctc ttttgagagt ttgcatggtg ttactccctg catagtgaag     1980
aaaacatttt atttaagtag atggatctaa gttttcatg aacaaaggaa tgacatttga      2040
aatcaatcct accctagtcc aggagaatgc attagattaa cctagtagag gtcttatttc     2100
accctgagtt ttctatgatc gtgattctct gctggaggag taattgtgaa atagatctct     2160
ctgggaactg gcttcctagt ccaatcagct cttttaccaa tgaacacttc cttgtgatat     2220
agatgtttat ggccgagagg atcccttcct ttctacctgt atttgtccta ataaattgtt     2280
gacttattaa ttcactactt cctcacagct ttttttggc tttacaaatc cactggaaag      2340
gtatatgggt gtatcacttt gtgtatttcg gtgtgcatgt gtagagggga caaaaatcct     2400
ctctcaaact ataaatattg agtatttgtg tattgaacat ttgctataac tactaggttt     2460
cttaaataat cttaatatat aaaatgatat agaaaagggg aaattatagt tcgtattatt     2520
catctaagtg aagagattaa aacccaggga gtaaataaat tgtctaagga ctaaggttgt     2580 atactatttta ggtgatagat atggggcaac cgtatgggtt ttatgattaa caaataaact    2640
tctcaccact ctaccatatc aacttttcca taaaagagag ctatagtatt ctttgcttaa     2700
ataaatttga ttagtgcatg acttcttgaa aacatataaa gcaaagtca catttgattc      2760 tatcagaaaa gtgagtaagc catggcccaa acaaaagatg cattaaaata ttctggaatg     2820
```

```
atggagctaa aagtaagaaa aatgactttt taaaaaagtt tactgttagg aattgtgaaa    2880
ttatgctgaa ttttagttgc attataattt ttgtcagtca tacggtctga caacctgtct    2940
tatttctatt tccccatatg aggaatgcta gttaagtatg gatattaact attactactt    3000
agatgcattg aagttgcata atatggataa tacttcactg gttccctgaa aatgtttagt    3060
tagtaataag tctcttacac tatttgtttt gtccaataat ttatattttc tgaagactta    3120
actctagaat acactcatgt caaaatgaaa gaatttcatt gcaaatatt gcttggtaca     3180 tgacgcatac ctgtatttgt tttgtgtcac aacatgaaaa atgatggttt attagaagtt    3240
tcattgggta ggaaacacat ttgaatggta tttactaaga tactaaaatc cttggacttc    3300
actctaattt tagtgccatt tagaactcaa ggtctcagta aaagtagaaa taaagcctgt    3360
taacaaaaca caagctgaat attaaaaatg taactggatt ttcaaagaaa tgtttactgg    3420
tattacctgt agatgtatat tctttattat gatcttttgt gtaaagtctg cagacaaat    3480 gcaatatcta attgttgagt ccaatatcac aagcagtaca aaagtataaa aaagacttgg    3540
ccttttctaa tgtgttaaaa tactttatgc tggtaataac actaagagta gggcactaga    3600
aattttaagt gaagataatg tgttgcagtt actgcactca atggcttact attataaacc    3660
aaaactggga tcactaagct ccagtcagtc aaaatgatca aaattattga agagaataag    3720
caattctgtt cttttattagg acacagtaga tacagactac aaagtggagt gtgcttaata    3780
agaggtagca tttgttaagt gtcaattact ctattatccc ttggagcttc tcaaaataac    3840
catataaggt gtaagatgtt aaaggttatg gttacactca gtgcacaggt aagctaatag    3900
gctgagagaa gctaaattac ttactggggt ctcacagtaa gaaagtgagc tgaagtttca    3960
gcccagattt aactggattc tgggctcttt attcatgtta cttcatgaat ctgtttctca    4020
attgtgcaga aaaaggggg ctatttataa gaaaagcaat aaacaaacaa gtaatgatct     4080
caaataagta atgcaagaaa tagtgagatt tcaaaatcag tggcagcgat ttctcagttc    4140
tgtcctaagt ggccttgctc aatcacctgc tatcttttag tggagctttg aaattatgtt    4200
tcagacaact tcgattcagt tctagaatgt ttgactcagc aaattcacag gctcatcttt    4260
ctaacttgat ggtgaatatg gaaattcagc taaatggatg ttaataaaat tcaaacgttt    4320
taaggacaga tgaaaatgac agaattttaa ggtaaaatat atgaaggaat ataagataaa    4380 ggattttct accttcagca aaaacatacc cactaattag taaaattaat aggcaaaaaa     4440
aagttgcatg ctcttatact gtaatgatta tcattttaaa actagctttt tgccttcgag    4500
ctatcggggt aaagacctac aggaaaacta ctgtcgaaat cctcgagggg aagaagggg     4560 accctggtgt ttcacaagca atccagaggt acgctacgaa gtctgtgaca ttcctcagtg    4620
ttcagaagtt gaatgcatga cctgcaatgg ggagagttat cgaggtctca tggatcatac    4680
agaatcaggc aagatttgtc agcgctggga tcatcagaca ccacaccggc acaaattctt    4740
gcctgaaaga tatcccgaca agggctttga tgataattat tgccgcaatc ccgatggcca    4800
gccgaggcca tggtgctata ctcttgaccc tcacacccgc tgggagtact gtgcaattaa    4860
aacatgcgct gacaatacta tgaatgacac tgatgttcct ttggaaacaa ctgaatgcat    4920
ccaaggtcaa ggagaaggct acaggggcac tgtcaatacc atttggaatg gaattccatg    4980
tcagcgttgg gattctcagt atcctcacga gcatgacatg actcctgaaa atttcaagtg    5040
caaggaccta cgagaaaatt actgccgaaa tccagatggg tctgaatcac cctggtgttt    5100
taccactgat ccaaacatcc gagttggcta ctgctcccaa attccaaact gtgatatgtc    5160
```

| | |
|---|---|
| acatggacaa gattgttatc gtgggaatgg caaaaattat atgggcaact tatcccaaac | 5220 |
| aagatctgga ctaacatgtt caatgtggga caagaacatg gaagacttac atcgtcatat | 5280 |
| cttctgggaa ccagatgcaa gtaagctgaa tgagaattac tgccgaaatc cagatgatga | 5340 |
| tgctcatgga ccctggtgct acacgggaaa tccactcatt ccttgggatt attgccctat | 5400 |
| ttctcgttgt gaaggtgata ccacacctac aatagtcaat ttagaccatc ccgtaatatc | 5460 |
| ttgtgccaaa acgaaacaat tgcgagttgt aaatgggatt ccaacacgaa caaacatagg | 5520 |
| atggatggtt agtttgagat acagaaataa acatatctgc ggaggatcat tgataaagga | 5580 |
| gagttgggtt cttactgcac gacagtgttt cccttctcga gacttgaaag attatgaagc | 5640 |
| ttggcttgga attcatgatg tccacggaag aggagatgag aaatgcaaac aggttctcaa | 5700 |
| tgtttcccag ctggtatatg gccctgaagg atcagatctg gttttaatga agcttgccag | 5760 |
| gcctgctgtc ctggatgatt ttgttagtac gattgattta cctaattatg gatgcacaat | 5820 |
| tcctgaaaag accagttgca gtgtttatgc ctggggctac actggattga tcaactatga | 5880 |
| tggcctatta cgagtggcac atctctatat aatgggaaat gagaaatgca gccagcatca | 5940 |
| tcgagggaag gtgactctga atgagtctga aatatgtgct ggggctgaaa agattggatc | 6000 |
| aggaccatgt gagggggatt atggtggccc acttgtttgt gagcaacata aaatgagaat | 6060 |
| ggttcttggt gtcattgttc ctggtcgtgg atgtgccatt ccaaatcgtc ctggtatttt | 6120 |
| tgtccgagta gcatattatg caaaatggat acacaaaatt attttaacat ataaggtacc | 6180 |
| acagtcatag | 6190 |

<210> SEQ ID NO 9
<211> LENGTH: 5190
<212> TYPE: DNA
<213> ORGANISM: Artificial Sequence
<220> FEATURE:
<223> OTHER INFORMATION: nucleotide sequence of HGF-X3

<400> SEQUENCE: 9

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aaagaagaaa tacaattcat | 120 |
| gaattcaaaa aatcagcaaa gactacccta atcaaaatag atccagcact gaagataaaa | 180 |
| accaaaaaag tgaatactgc agaccaatgt gctaatagat gtactaggaa taaggacttc | 240 |
| ccattcactt gcaaggcttt tgttttgat aaagcaagaa acaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatt ggtaaaggac gcagctacaa gggaacagta | 420 |
| tctatcacta gagtggcat caatgtcag ccctggagtt ccatgatacc acacgaacac | 480 |
| aggtaagaac agtatgaaga aaagagatga agcctctgtc tttttacat gttaacagtc | 540 |
| tcatattagt ccttcagaat aattctacaa tcctaaaata acttagccaa cttgctgaat | 600 |
| tgtattacgg caaggtttat atgaattcat gactgatatt tagcaaatga ttaattaata | 660 |
| tgttaataaa atgtagccaa acaatatct taccttaatg cctcaatttg tagatctcgg | 720 |
| tatttgtgaa ataataacgt aaacttcgtt taaaaggatt cttcttcctg tctttgagaa | 780 |
| agtacggcac tgtgcagggg gagaggttga ttgtgaaaaa tcagaggtag atgagaatct | 840 |
| tactgagggc tgagggttct ttaaccttgg tggatctcaa cattggttgc acattaaaat | 900 |
| cacctgctgc aagcccttga cgaatcttac ttagaagatg acaacacaga acaattaaat | 960 |
| cagaatctct ggggagaata gggcaccagt attttttgag ctcccaccat gattccaaag | 1020 |

```
tgcagccaaa tttgagaacc actgctaaaa gctcaagctt cagattgacc agcttttcca    1080
tctcacctat cgcctaaaga ccaaattgga taaatgtgtt cattacgaca gatgggtact    1140
atttaaagat gagtaaacac aatatactta ggctcgtcag actgagagtt ttaatcatca    1200
ctgaggaaaa acatagatat ctaatactga ctggagtatt agtcaaggct tatttcacac    1260
acaattttat cagaaaccaa agtagtttaa aacagctctc cccttattag taatgcattg    1320
gagggtttac tttaccatgt accttgctga gcactgtacc ttgttaatct catttacttg    1380
taatgagaac cacacagcgg gtagttttat tggttctatt ttacctacat gacaaaactg    1440
aagcataaaa acacttagta agttttcagt gtcatgcaca actaggaagt gacatggcca    1500
gaatataagc ccagtcacca tcactctata acctgcgctt taacaactt cagggcatga     1560 cacatttggc cggtcagtag aacccatgct gtgatttgtt tttgcagtgg tggtgatgac    1620
tgccttgttg aatccacttt ttattctatt ccattttggg gacacaattc tgcaagatga    1680
ttcttcatta ggaaacagag atgagttatt gaccaacaca gaaagaaaaa gagtttgttg    1740
ctccacactg ggattaaacc tatgatcttg gcctaattaa cactagctag taagtgtcca    1800
agctgatcat ctctacaaca tttcaataac agaaaacaac aattttcaaa attagttact    1860
tacaattatg tagaaatgcc tctaaaacac agtattttcc ttatattaca aaaacaaaaa    1920
ttataattgg ttttgtcctc ttttgagagt ttgcatggtg ttactccctg catagtgaag    1980
aaaacatttt atttaagtag atggatctaa gttttttcatg aacaaaggaa tgacatttga   2040
aatcaatcct accctagtcc aggagaatgc attagattaa cctagtagag gtcttatttc    2100
accctgagtt ttctatgatc gtgattctct gctggaggag taattgtgaa atagatctct    2160 ctggaactg gcttcctagt ccaatcagct cttttaccaa tgaacacttc cttgtgatat      2220
agatgtttat ggccgagagg atcctgggta ggaaacacat ttgaatggta tttactaaga    2280
tactaaaatc cttggacttc actctaattt tagtgccatt tagaactcaa ggtctcagta    2340
aaagtagaaa taaagcctgt taacaaaaca caagctgaat attaaaaatg taactggatt    2400
ttcaaagaaa tgtttactgg tattacctgt agatgtatat tctttattat gatcttttgt    2460
gtaaagtctg gcagacaaat gcaatatcta attgttgagt ccaatatcac aagcagtaca    2520
aaagtataaa aaagacttgg cctttcctaa tgtgttaaaa tactttatgc tggtaataac    2580
actaagagta gggcactaga aattttaagt gaagataatg tgttgcagtt actgcactca    2640
atggcttact attataaacc aaaactggga tcactaagct ccagtcagtc aaaatgatca    2700
aaattattga agagaataag caattctgtt ctttattagg acacagtaga tacagactac    2760
aaagtggagt gtgcttaata agaggtagca tttgttaagt gtcaattact ctattatccc    2820
ttggagcttc tcaaaataac catataaggt gtaagatgtt aaaggttatg gttacactca    2880
gtgcacaggt aagctaatag gctgagagaa gctaaattac ttactggggt ctcacagtaa    2940
gaaagtgagc tgaagtttca gcccagattt aactggattc tgggctcttt attcatgtta    3000
cttcatgaat ctgtttctca attgtgcaga aaaaggggg ctatttataa gaaaagcaat      3060
aaacaaacaa gtaatgatct caaataagta atgcaagaaa tagtgagatt tcaaaatcag    3120
tggcagcgat ttctcagttc tgtcctaagt ggccttgctc aatcacctgc tatcttttag    3180
tggagctttg aaattatgtt tcagacaact tcgattcagt tctagaatgt ttgactcagc    3240
aaattcacag gctcatcttt ctaacttgat ggtgaatatg gaaattcagc taaatggatg    3300
ttaataaaat tcaaacgttt taaggacaga tgaaaatgac agaatttaa ggtaaaatat      3360
```

-continued

| | |
|---|---|
| atgaaggaat ataagataaa ggattttct accttcagca aaaacatacc cactaattag | 3420 |
| taaaattaat aggcaaaaaa aagttgcatg ctcttatact gtaatgatta tcattttaaa | 3480 |
| actagctttt tgccttcgag ctatcggggt aaagacctac aggaaaacta ctgtcgaaat | 3540 |
| cctcgagggg aagaaggggg accctggtgt tcacaagca atccagaggt acgctacgaa | 3600 |
| gtctgtgaca ttcctcagtg ttcagaagtt gaatgcatga cctgcaatgg ggagagttat | 3660 |
| cgaggtctca tggatcatac agaatcaggc aagatttgtc agcgctggga tcatcagaca | 3720 |
| ccacaccggc acaaattctt gcctgaaaga tatcccgaca agggctttga tgataattat | 3780 |
| tgccgcaatc ccgatggcca gccgaggcca tggtgctata ctcttgaccc tcacacccgc | 3840 |
| tgggagtact gtgcaattaa acatgcgct gacaatacta tgaatgacac tgatgttcct | 3900 |
| ttggaaacaa ctgaatgcat ccaaggtcaa ggagaaggct acaggggcac tgtcaatacc | 3960 |
| atttggaatg gaattccatg tcagcgttgg gattctcagt atcctcacga gcatgacatg | 4020 |
| actcctgaaa atttcaagtg caaggaccta cgagaaaatt actgccgaaa tccagatggg | 4080 |
| tctgaatcac cctggtgttt taccactgat ccaaacatcc gagttggcta ctgctcccaa | 4140 |
| attccaaact gtgatatgtc acatggacaa gattgttatc gtgggaatgg caaaaattat | 4200 |
| atgggcaact tatcccaaac aagatctgga ctaacatgtt caatgtggga caagaacatg | 4260 |
| gaagacttac atcgtcatat cttctgggaa ccagatgcaa gtaagctgaa tgagaattac | 4320 |
| tgccgaaatc cagatgatga tgctcatgga ccctggtgct acacgggaaa tccactcatt | 4380 |
| ccttgggatt attgccctat ttctcgttgt gaaggtgata ccacacctac aatagtcaat | 4440 |
| ttagaccatc ccgtaatatc ttgtgccaaa acgaaacaat gcgagttgt aaatgggatt | 4500 |
| ccaacacgaa caaacatagg atggatggtt agtttgagat acagaaataa acatatctgc | 4560 |
| ggaggatcat tgataaagga gagttgggtt cttactgcac gacagtgttt cccttctcga | 4620 |
| gacttgaaag attatgaagc ttggcttgga attcatgatg tccacggaag aggagatgag | 4680 |
| aaaatgcaaac aggttctcaa tgtttcccag ctggtatatg gccctgaagg atcagatctg | 4740 |
| gtttaatga agcttgccag gcctgctgtc ctggatgatt ttgttagtac gattgattta | 4800 |
| cctaattatg gatgcacaat tcctgaaaag accagttgca gtgtttatgg ctggggctac | 4860 |
| actggattga tcaactatga tggcctatta cgagtggcac atctctatat aatgggaaat | 4920 |
| gagaaatgca gccagcatca tcgagggaag gtgactctga atgagtctga aatatgtgct | 4980 |
| ggggctgaaa agattggatc aggaccatgt gagggggatt atggtggccc acttgtttgt | 5040 |
| gagcaacata aaatgagaat ggttcttggt gtcattgttc ctggtcgtgg atgtgccatt | 5100 |
| ccaaatcgtc ctggtatttt tgtccgagta gcatattatg caaaatggat acacaaaatt | 5160 |
| attttaacat ataaggtacc acagtcatag | 5190 |

<210> SEQ ID NO 10
<211> LENGTH: 4241
<212> TYPE: DNA
<213> ORGANISM: Artificial Sequence
<220> FEATURE:
<223> OTHER INFORMATION: nucleotide sequence of HGF-X4

<400> SEQUENCE: 10

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aagaagaaa tacaattcat | 120 |
| gaattcaaaa aatcagcaaa gactacccta atcaaaatag atccagcact gaagataaaa | 180 |
| accaaaaaag tgaatactgc agaccaatgt gctaatagat gtactaggaa taaggactt | 240 |

```
ccattcactt gcaaggcttt tgtttttgat aaagcaagaa aacaatgcct ctggttcccc      300
ttcaatagca tgtcaagtgg agtgaaaaaa gaatttggcc atgaatttga cctctatgaa      360
aacaaagact acattagaaa ctgcatcatt ggtaaaggac gcagctacaa gggaacagta      420
tctatcacta gagtggcat caaatgtcag ccctggagtt ccatgatacc acacgaacac       480
aggtaagaac agtatgaaga aaagagatga agcctctgtc ttttttacat gttaacagtc      540
tcatattagt ccttcagaat aattctacaa tcctaaaata acttagccaa cttgctgaat      600
tgtattacgg caaggtttat atgaattcat gactgatatt tagcaaatga ttaattaata      660
tgttaataaa atgtagccaa aacaatatct taccttaatg cctcaatttg tagatctcgg      720
tatttgtgaa ataataacgt aaacttcgtt taaaaggatt cttcttcctg tctttgagaa      780
agtacggcac tgtgcagggg gagaggttga ttgtgaaaaa tcagaggtag atgagaatct      840
tactgagggc tgagggttct ttaaccttgg tggatctcaa cattggttgc acattaaaat      900
cacctgctgc aagcccttga cgaatcttac ttagaagatg acaacacaga acaattaaat      960
cagaatctct ggggagaata gggcaccagt attttttgag ctcccaccat gattccaaag     1020
tgcagccaaa tttgagaacc actgctaaaa gctcaagctt cagattgacc agcttttcca     1080
tctcacctat cgcctaaaga ccaaattgga taaatgtgtt cattacgaca gatgggtact     1140
atttaaagat gagtaaacac aatatactta ggctcgtcag actgagagtt ttaatcatca     1200
ctgaggaaaa acatagatat ctaatactga ctggagtatt agtcaaggct tatttcacac     1260
acaattttat cagaaaccaa agtagttaa aacagctctc cccttattag taatgcattg      1320
gagggtttac tttaccatgt accttgctga gcactgtacc ttgttaatct catttacttg     1380
taatgagaac cacacagcgg gtagttttat tggttctatt ttacctacat gacaaaactg     1440
aagcataaaa acacttagta agttttcagt gtcatgcaca actaggaagt gacatggcca     1500
gaatataagc ccagtcacca tcactctata acctgcgctt ttaacaactt cagggcatga     1560
cacatttggc cggtcagtag aacccatgct gtgatttgtt tttgcagtgg tggtgatgac     1620
tgccttgttg aatccacttt ttattctatt ccattttggg gacacaattc tgcaagatga     1680
ttcttcatta ggaaacagag atgagttatt gaccaacaca gaaagaaaaa gagtttgttg     1740
ctccacactg ggattaaacc tatgatcttg gcctaattaa cactagctag taagtgtcca     1800
agctgatcat ctctacaaca tttcaataac agaaaacaac aatttcaaa attagttact      1860 tacaattatg tagaaatgcc tctaaaacac agtattttcc ttatattaca aaaacaaaaa     1920
ttataattgg ttttgtcctc ttttgagagt ttgcatggtg ttactccctg catagtgaag     1980
aaaacatttt atttaagtag atggatctaa gttttcatg aacaaggaa tgacatttga       2040 aatcaatcct accctagtcc aggagaatgc attagattaa cctagtagag gtcttatttc     2100
accctgagtt ttctatgatc gtgattctct gctggaggag taattgtgaa atagatctct     2160
ctgggaactg gcttcctagt ccaatcagct cttttaccaa tgaacacttc cttgtgatat     2220
agatgtttat ggccgagagg atccttatgt ttcagacaac ttcgattcag ttctagaatg     2280
tttgactcag caaattcaca ggctcatctt tctaacttga tggtgaatat ggaaattcag     2340
ctaaatggat gttaataaaa ttcaaacgtt ttaaggacag atgaaaatga cagaattta      2400 aggtaaaata tatgaaggaa tataagataa aggattttc taccttcagc aaaaacatac      2460
ccactaatta gtaaaattaa taggcaaaaa aaagttgcat gctcttatac tgtaatgatt     2520
atcattttaa aactagcttt ttgccttcga gctatcgggg taaagaccta caggaaaact     2580
```

-continued

| | |
|---|---|
| actgtcgaaa tcctcgaggg gaagaagggg gaccctggtg tttcacaagc aatccagagg | 2640 |
| tacgctacga agtctgtgac attcctcagt gttcagaagt tgaatgcatg acctgcaatg | 2700 |
| gggagagtta tcgaggtctc atggatcata cagaatcagg caagatttgt cagcgctggg | 2760 |
| atcatcagac accacaccgg cacaaattct tgcctgaaag atatcccgac aagggctttg | 2820 |
| atgataatta ttgccgcaat cccgatggcc agccgaggcc atggtgctat actcttgacc | 2880 |
| ctcacacccg ctgggagtac tgtgcaatta aacatgcgc tgacaatact atgaatgaca | 2940 |
| ctgatgttcc tttggaaaca actgaatgca tccaaggtca aggagaaggc tacaggggca | 3000 |
| ctgtcaatac catttggaat ggaattccat gtcagcgttg ggattctcag tatcctcacg | 3060 |
| agcatgacat gactcctgaa aatttcaagt gcaaggacct acgagaaaat tactgccgaa | 3120 |
| atccagatgg gtctgaatca ccctggtgtt ttaccactga tccaaacatc cgagttggct | 3180 |
| actgctccca aattccaaac tgtgatatgt cacatggaca agattgttat cgtgggaatg | 3240 |
| gcaaaaatta tatgggcaac ttatcccaaa caagatctgg actaacatgt tcaatgtggg | 3300 |
| acaagaacat ggaagactta catcgtcata tcttctggga accagatgca agtaagctga | 3360 |
| atgagaatta ctgccgaaat ccagatgatg atgctcatgg accctggtgc tacacgggaa | 3420 |
| atccactcat tccttgggat tattgcccta tttctcgttg tgaaggtgat accacaccta | 3480 |
| caatagtcaa tttagaccat cccgtaatat cttgtgccaa aacgaaacaa ttgcgagttg | 3540 |
| taaatgggat tccaacacga acaaacatag gatggatggt tagtttgaga tacagaaata | 3600 |
| aacatatctg cggaggatca ttgataaagg agagttgggt tcttactgca cgacagtgtt | 3660 |
| tcccttctcg agacttgaaa gattatgaag cttggcttgg aattcatgat gtccacggaa | 3720 |
| gaggagatga gaaatgcaaa caggttctca atgtttccca gctggtatat ggccctgaag | 3780 |
| gatcagatct ggttttaatg aagcttgcca ggcctgctgt cctggatgat tttgttagta | 3840 |
| cgattgattt acctaattat ggatgcacaa ttcctgaaaa gaccagttgc agtgtttatg | 3900 |
| gctggggcta cactggattg atcaactatg atggcctatt acgagtggca catctctata | 3960 |
| taatgggaaa tgagaaatgc agccagcatc atcgagggaa ggtgactctg aatgagtctg | 4020 |
| aaatatgtgc tggggctgaa aagattgat caggaccatg tgaggggat tatggtggcc | 4080 |
| cacttgtttg tgagcaacat aaaatgagaa tggttcttgg tgtcattgtt cctggtcgtg | 4140 |
| gatgtgccat tccaaatcgt cctggtattt ttgtccgagt agcatattat gcaaaatgga | 4200 |
| tacacaaaat tattttaaca tataaggtac cacagtcata g | 4241 |

<210> SEQ ID NO 11
<211> LENGTH: 5602
<212> TYPE: DNA
<213> ORGANISM: Artificial Sequence
<220> FEATURE:
<223> OTHER INFORMATION: nucleotide sequence of HGF-X5

<400> SEQUENCE: 11

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aagaagaaa tacaattcat | 120 |
| gaattcaaaa aatcagcaaa gactacccta atcaaaatag atccagcact gaagataaaa | 180 |
| accaaaaaag tgaatactgc agaccaatgt gctaatagat gtactaggaa taaaggactt | 240 |
| ccattcactt gcaaggcttt tgttttttga taaagcaagaa aacaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatt ggtaaaggac gcagctacaa gggaacagta | 420 |

```
tctatcacta agagtggcat caaatgtcag ccctggagtt ccatgatacc acacgaacac    480
aggtaagaac agtatgaaga aaagagatga agcctctgtc ttttttacat gttaacagtc    540
tcatattagt ccttcagaat aattctacaa tcctaaaata acttagccaa cttgctgaat    600
tgtattacgg caaggtttat atgaattcat gactgatatt tagcaaatga ttaattaata    660
tgttaataaa atgtagccaa aacaatatct taccttaatg cctcaatttg tagatctcgg    720
tatttgtgga tccagtatat taataaaatc ccttttttgta ttcaatgagg gaaacacata   780
attttcatca attagcagct tattggaata tctgcatgat ggtttaacac ttttaagtgt    840
tgactaaaga ttaattttac agaaaataga aaaagaaata tgtttctgtc tggaggaatg    900
atttattgtt gaccctaaa ttgaaatatt ttactagtgg cttaatggaa agatgatgaa     960
agatgatgaa attaatgtag aagcttaact agaaaatcag gtgacctgat atctacatct   1020
gtatccttca ttggccaccc agcattcatt aatgaatcag atgatggaat agatcaagtt   1080
tcctaggaac acagtgaata ttaaaagaaa acaaagggag cctagcacct agaagaccta   1140
gtttatattt caagtatat ttggatgtaa cccaatttta aacatttcct cacttgtctc    1200
tcttaaagcc ttgccaacag caaggacaga gaaccaaaaa tagtgtatat atgaataaat   1260
gcttattaca gaatctgctg actggcacat gctttgtgtg taatgggttc tcataaacac   1320
ttgttgaatg aacacacata agtgaaagag catggctagg cttcatccct tggtcaaata   1380
tggggtgcta agaaaagca ggggaaatac attgggacac taacaaaaaa aaacagttaa    1440
tttaggtaaa agataaaata caccacagaa tgaagaaaag agtgacccca gactgctctt   1500
taaccttcat gtcctagaga ggttttttgat atgaattgca ttcagaattg tggaaaggag   1560
cccatctttt ctcttcattt tgattttatt aactccaatg ggggaatttt attcgtgttt   1620
tggccatatc tactttttgat ttctacatta ttctctcttc ctttctacct gtatttgtcc   1680
taataaattg ttgacttatt aattcactac ttcctcacag cttttttttg gctttacaaa   1740
tccactggaa aggtatatgg gtgtatcact ttgtgtattt cggtgtgcat gtgtagaggg   1800
gacaaaaatc ctctctcaaa ctataaatat tgagtatttg tgtattgaac atttgctata   1860
actactaggt ttcttaaata atcttaatat ataaatgat atagaaaaag ggaaattata    1920
gttcgtatta ttcatctaag tgaagagatt aaaacccagg gagtaaataa attgtctaag   1980
gactaaggtt gtatactatt taggtgatag atatggggca accgtatggg ttttatgatt   2040
aacaaataaa cttctcacca ctctaccata tcaacttttc cataaaagag agctatagta   2100
ttctttgctt aaataaattt gattagtgca tgacttcttg aaaacatata aagcaaaagt   2160
cacatttgat tctatcagaa aagtgagtaa gccatggccc aaacaaaaga tgcattaaaa   2220
tattctggaa tgatggagct aaaagtaaga aaaatgactt tttaaaaaag tttactgtta   2280
ggaattgtga aattatgctg aattttagtt gcattataat ttttgtcagt catacggtct   2340
gacaacctgt cttatttcta tttccccata tgaggaatgc tagttaagta tggatattaa   2400
ctattactac ttagatgcat tgaagttgca taatatggat aatacttcac tggttccctg   2460
aaaatgttta gttagtaata agtctcttac actatttgtt ttgtccaata atttatattt   2520
tctgaagact taactctaga atacactcat gtcaaaatga aagaatttca ttgcaaaata   2580
ttgcttggta catgacgcat acctgtattt gttttgtgtc acaacatgaa aaatgatggt   2640
ttattagaag tttcattggg taggaaacac atttgaatgg tatttactaa gatactaaaa   2700
tccttggact tcactctaat tttagtgcca tttagaactc aaggtctcag taaaagtaga   2760
```

```
aataaagcct gttaacaaaa cacaagctga atattaaaaa tgtaactgga ttttcaaaga      2820
aatgtttact ggtattacct gtagatgtat attctttatt atgatctttt gtgtaaagtc      2880
tggcagacaa atgcaatatc taattgttga gtccaatatc acaagcagta caaaagtata      2940
aaaaagactt ggccttttct aatgtgttaa aatactttat gctggtaata acactaagag      3000
tagggcacta gaaattttaa gtgaagataa tgtgttgcag ttactgcact caatggctta      3060
ctattataaa ccaaaactgg gatcactaag ctccagtcag tcaaaatgat caaaattatt      3120
gaagagaata agcaattctg ttctttatta ggacacagta gatacagact acaaagtgga      3180
gtgtgcttaa taagaggtag catttgttaa gtgtcaatta ctctattatc ccttggagct      3240
tctcaaaata accatataag gtgtaagatg ttaaaggtta tggttacact cagtgcacag      3300
gtaagctaat aggctgagag aagctaaatt acttactggg gtctcacagt aagaaagtga      3360
gctgaagttt cagcccagat ttaactggat tctgggctct ttattcatgt tacttcatga      3420
atctgtttct caattgtgca gaaaaaaggg ggctatttat aagaaaagca ataaacaaac      3480
aagtaatgat ctcaaataag taatgcaaga aatagtgaga tttcaaaatc agtggcagcg      3540
atttctcagt tctgtcctaa gtggccttgc tcaatcacct gctatctttt agtggagctt      3600
tgaaattatg tttcagacaa cttcgattca gttctagaat gtttgactca gcaaattcac      3660
aggctcatct ttctaacttg atggtgaata tggaaattca gctaaatgga tgttaataaa      3720
attcaaacgt tttaaggaca gatgaaaatg acagaatttt aaggtaaaat atatgaagga      3780
atataagata aaggattttt ctaccttcag caaaaacata cccactaatt agtaaaatta      3840
ataggcaaaa aaaagttgca tgctcttata ctgtaatgat tatcatttta aaactagctt      3900
tttgccttcg agctatcggg gtaaagacct acaggaaaac tactgtcgaa atcctcgagg      3960
ggaagaaggg ggaccctggt gtttcacaag caatccagag gtacgctacg aagtctgtga      4020
cattcctcag tgttcagaag ttgaatgcat gacctgcaat ggggagagtt atcgaggtct      4080
catggatcat acagaatcag gcaagatttg tcagcgctgg gatcatcaga caccacaccg      4140
gcacaaattc ttgcctgaaa gatatcccga caagggcttt gatgataatt attgccgcaa      4200
tcccgatggc cagccgaggc catggtgcta tactcttgac cctcacaccc gctgggagta      4260
ctgtgcaatt aaaacatgcg ctgacaatac tatgaatgac actgatgttc ctttggaaac      4320
aactgaatgc atccaaggtc aaggagaagg ctacaggggc actgtcaata ccatttggaa      4380
tggaattcca tgtcagcgtt gggattctca gtatcctcac gagcatgaca tgactcctga      4440
aaatttcaag tgcaaggacc tacgagaaaa ttactgccga atccagatgg ggtctgaatc      4500
accctggtgt tttaccactg atccaaacat ccgagttggc tactgctccc aaattccaaa      4560
ctgtgatatg tcacatggac aagattgtta tcgtgggaat ggcaaaaatt atatgggcaa      4620
cttatcccaa acaagatctg gactaacatg ttcaatgtgg gacaagaaca tggaagactt      4680
acatcgtcat atcttctggg aaccagatgc aagtaagctg aatgagaatt actgccgaaa      4740
tccagatgat gatgctcatg gaccctggtg ctacacggga aatccactca ttccttggga      4800
ttattgccct atttctcgtt gtgaaggtga taccacacct acaatagtca atttagacca      4860
tcccgtaata tcttgtgcca aaacgaaaca attgcgagtt gtaaatggga ttccaacacg      4920
aacaaacata ggatggatgg ttagtttgag atacagaaat aaacatatct gcggaggatc      4980
attgataaag gagagttggg ttcttactgc acgacagtgt ttcccttctc gagacttgaa      5040
agattatgaa gcttggcttg gaattcatga tgtccacgga agaggagatg agaaatgcaa      5100
acaggttctc aatgtttccc agctggtata tggccctgaa ggatcagatc tggttttaat      5160
```

| | |
|---|---|
| gaagcttgcc aggcctgctg tcctggatga ttttgttagt acgattgatt tacctaatta | 5220 |
| tggatgcaca attcctgaaa agaccagttg cagtgtttta ggctggggct acactggatt | 5280 |
| gatcaactat gatggcctat tacgagtggc acatctctat ataatgggaa atgagaaatg | 5340 |
| cagccagcat catcgaggga aggtgactct gaatgagtct gaaatatgtg ctggggctga | 5400 |
| aaagattgga tcaggaccat gtgaggggga ttatggtggc ccacttgttt gtgagcaaca | 5460 |
| taaaatgaga atggttcttg gtgtcattgt tcctggtcgt ggatgtgcca ttccaaatcg | 5520 |
| tcctggtatt tttgtccgag tagcatatta tgcaaaatgg atacacaaaa ttattttaac | 5580 |
| atataaggta ccacagtcat ag | 5602 |

<210> SEQ ID NO 12
<211> LENGTH: 4679
<212> TYPE: DNA
<213> ORGANISM: Artificial Sequence
<220> FEATURE:
<223> OTHER INFORMATION: nucleotide sequence of HGF-X6

<400> SEQUENCE: 12

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aagaagaaa tacaattcat | 120 |
| gaattcaaaa atcagcaaa gactacccta atcaaaatag atccagcact gaagataaaa | 180 |
| accaaaaaag tgaatactgc agaccaatgt gctaatagat gtactaggaa taaaggactt | 240 |
| ccattcactt gcaaggcttt tgttttttgat aaagcaagaa acaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatt ggtaaaggac gcagctacaa gggaacagta | 420 |
| tctatcacta gagtggcat caaatgtcag ccctggagtt ccatgatacc acacgaacac | 480 |
| aggtaagaac agtatgaaga aaagagatga agcctctgtc tttttttacat gttaacagtc | 540 |
| tcatattagt ccttcagaat aattctacaa tcctaaaata acttagccaa cttgctgaat | 600 |
| tgtattacgg caaggtttat atgaattcat gactgatatt tagcaaatga ttaattaata | 660 |
| tgttaataaa atgtagccaa acaatatct taccttaatg cctcaatttg tagatctcgg | 720 |
| tatttgtgga tcccttcctt tctacctgta tttgtcctaa taaattgttg acttattaat | 780 |
| tcactacttc ctcacagctt ttttttggct ttacaaatcc actggaaagg tatatggtg | 840 |
| tatcactttg tgtatttcgg tgtgcatgtg tagaggggac aaaaatcctc tctcaaacta | 900 |
| taaatattga gtatttgtgt attgaacatt tgctataact actaggtttc ttaaataatc | 960 |
| ttaatatata aaatgatata gaaaagggaa attatagtt cgtattattc atctaagtga | 1020 |
| agagattaaa acccagggag taaataaatt gtctaaggac taaggttgta tactatttag | 1080 |
| gtgatagata tggggcaacc gtatgggttt tatgattaac aaataaactt ctcaccactc | 1140 |
| taccatatca actttttccat aaaagagagc tatagtattc tttgcttaaa taaatttgat | 1200 |
| tagtgcatga cttcttgaaa acatataaag caaaagtcac atttgattct atcagaaaag | 1260 |
| tgagtaagcc atggcccaaa caaaagatgc attaaaatat tctggaatga tggagctaaa | 1320 |
| agtaagaaaa atgacttttt aaaaaagttt actgttagga attgtgaaat tatgctgaat | 1380 |
| tttagttgca ttataatttt tgtcagtcat acggtctgac aacctgtctt atttctatttt | 1440 |
| ccccatatga ggaatgctag ttaagtatgg atattaacta ttactactta gatgcattga | 1500 |
| agttgcataa tatggataat acttcactgg ttccctgaaa atgtttagtt agtaataagt | 1560 |

```
ctcttacact atttgttttg tccaataatt tatattttct gaagacttaa ctctagaata   1620
cactcatgtc aaaatgaaag aatttcattg caaaatattg cttggtacat gacgcatacc   1680
tgtatttgtt ttgtgtcaca acatgaaaaa tgatggttta ttagaagttt cattgggtag   1740
gaaacacatt tgaatggtat ttactaagat actaaaatcc ttggacttca ctctaatttt   1800
agtgccattt agaactcaag gtctcagtaa aagtagaaat aaagcctgtt aacaaaacac   1860
aagctgaata ttaaaaatgt aactggattt caaagaaat gtttactggt attacctgta    1920
gatgtatatt ctttattatg atcttttgtg taaagtctgg cagacaaatg caatatctaa   1980
ttgttgagtc caatatcaca agcagtacaa agtataaaa aagacttggc cttttctaat    2040
gtgttaaaat actttatgct ggtaataaca ctaagagtag ggcactagaa attttaagtg   2100
aagataatgt gttgcagtta ctgcactcaa tggcttacta ttataaacca aaactgggat   2160
cactaagctc cagtcagtca aaatgatcaa aattattgaa gagaataagc aattctgttc   2220
tttattagga cacagtagat acagactaca agtggagtg tgcttaataa gaggtagcat    2280
ttgttaagtg tcaattactc tattatccct tggagcttct caaaataacc atataaggtg   2340
taagatgtta aaggttatgg ttacactcag tgcacaggta agctaatagg ctgagagaag   2400
ctaaattact tactggggtc tcacagtaag aaagtgagct gaagtttcag cccagattta   2460
actggattct gggctcttta ttcatgttac ttcatgaatc tgtttctcaa ttgtgcagaa   2520 aaaggggc tatttataag aaaagcaata acaaacaag taatgatctc aaataagtaa      2580
tgcaagaaat agtgagattt caaaatcagt ggcagcgatt tctcagttct gtcctaagtg   2640
gccttgctca atcacctgct atcttttagt ggagctttga aattatgttt cagacaactt   2700
cgattcagtt ctagaatgtt tgactcagca aattcacagg ctcatctttc taacttgatg   2760
gtgaatatgg aaattcagct aaatggatgt taataaaatt caaacgtttt aaggacagat   2820
gaaaatgaca gaattttaag gtaaaatata tgaaggaata taagataaag gatttttcta   2880
ccttcagcaa aaacataccc actaattagt aaaattaata ggcaaaaaaa agttgcatgc   2940
tcttatactg taatgattat cattttaaaa ctagcttttt gccttcgagc tatcggggta   3000
aagacctaca ggaaaactac tgtcgaaatc ctcgagggga agaaggggga ccctggtgtt   3060
tcacaagcaa tccagaggta cgctacgaag tctgtgacat tcctcagtgt tcagaagttg   3120
aatgcatgac ctgcaatggg gagagttatc gaggtctcat ggatcataca gaatcaggca   3180
agatttgtca gcgctgggat catcagacac cacaccggca caaattcttg cctgaaagat   3240
atcccgacaa gggctttgat gataattatt gccgcaatcc cgatggccag ccgaggccat   3300
ggtgctatac tcttgacccgt cacacccgct gggagtactg tgcaattaaa acatgcgctg   3360
acaatactat gaatgacact gatgttcctt tggaaacaac tgaatgcatc caaggtcaag   3420
gagaaggcta caggggcact gtcaatacca tttggaatgg aattccatgt cagcgttggg   3480
attctcagta tcctcacgag catgacatga ctcctgaaaa tttcaagtgc aaggacctac   3540
gagaaaatta ctgccgaaat ccagatgggt ctgaatcacc ctggtgtttt accactgatc   3600
caaacatccg agttggctac tgctcccaaa ttccaaactg tgatatgtca catggacaag   3660
attgttatcg tgggaatggc aaaaattata tgggcaactt atcccaaaca agatctggac   3720
taacatgttc aatgtgggac aagaacatgg aagacttaca tcgtcatatc ttctgggaac   3780
cagatgcaag taagctgaat gagaaattact gccgaaatcc agatgatgat gctcatggac   3840
cctggtgcta cacgggaaat ccactcattc cttgggatta ttgccctatt tctcgttgtg   3900
aaggtgatac cacacctaca atagtcaatt tagaccatcc cgtaatatct tgtgccaaaa   3960
```

-continued

```
cgaaacaatt gcgagttgta aatgggattc caacacgaac aaacatagga tggatggtta    4020
gtttgagata cagaaataaa catatctgcg gaggatcatt gataaaggag agttgggttc    4080
ttactgcacg acagtgtttc ccttctcgag acttgaaaga ttatgaagct tggcttggaa    4140
ttcatgatgt ccacggaaga ggagatgaga aatgcaaaca ggttctcaat gtttcccagc    4200
tggtatatgg ccctgaagga tcagatctgg ttttaatgaa gcttgccagg cctgctgtcc    4260
tggatgattt tgttagtacg attgatttac ctaattatgg atgcacaatt cctgaaaaga    4320
ccagttgcag tgtttatggc tggggctaca ctggattgat caactatgat ggcctattac    4380
gagtggcaca tctctatata tgggaaatg agaaatgcag ccagcatcat cgagggaagg    4440
tgactctgaa tgagtctgaa atatgtgctg gggctgaaaa gattggatca ggaccatgtg    4500
agggggatta tggtggccca cttgtttgtg agcaacataa aatgagaatg gttcttggtg    4560
tcattgttcc tggtcgtgga tgtgccattc caaatcgtcc tggtatttt gtccgagtag    4620 catattatgc aaaatggata cacaaaatta ttttaacata aaggtacca cagtcatag    4679
```

<210> SEQ ID NO 13
<211> LENGTH: 3679
<212> TYPE: DNA
<213> ORGANISM: Artificial Sequence
<220> FEATURE:
<223> OTHER INFORMATION: nucleotide sequence of HGF-X7

<400> SEQUENCE: 13

```
atgtgggtga ccaaactcct gccagccctg ctgctgcagc atgtcctcct gcatctcctc      60
ctgctcccca tcgccatccc ctatgcagag ggacaaagga aagaagaaa tacaattcat     120 gaattcaaaa aatcagcaaa gactacccta atcaaaatag atccagcact gaagataaaa     180
accaaaaaag tgaatactgc agaccaatgt gctaatagag tactaggaa taaaggactt     240 ccattcactt gcaaggcttt tgttttttgat aaagcaagaa acaatgcct ctggttcccc     300 ttcaatagca tgtcaagtgg agtgaaaaaa gaatttggcc atgaatttga cctctatgaa     360
aacaaagact acattagaaa ctgcatcatt ggtaaaggac gcagctacaa gggaacagta     420
tctatcacta gagtggcat caaatgtcag ccctggagtt ccatgatacc acacgaacac     480
aggtaagaac agtatgaaga aaagagatga agcctctgtc tttttacat gttaacagtc     540 tcatattagt ccttcagaat aattctacaa tcctaaaata acttagccaa cttgctgaat     600
tgtattacgg caaggttat atgaattcat gactgatatt tagcaaatga ttaattaata     660
tgttaataaa atgtagccaa aacaatatct taccttaatg cctcaatttg tagatctcgg     720
tatttgtgga tcctgggtag gaaacacatt tgaatggtat ttactaagat actaaaatcc     780
ttggacttca ctctaatttt agtgccattt agaactcaag gtctcagtaa agtagaaat     840 aaagcctgtt aacaaaacac aaactgaata ttaaaatgt aactggattt tcaaagaaat     900
gtttactggt attacctgta gatgtatatt ctttattatg atctttttgtg taaagtctgg     960 cagacaaatg caatatctaa ttgttgagtc caatatcaca agcagtacaa aagtataaaa    1020
aagacttggc cttttctaat gtgttaaaat actttatgct ggtaataaca ctaagagtag    1080
ggcactagaa attttaagtg aagataatgt gttgcagtta ctgcactcaa tggcttacta    1140
ttataaacca aaactgggat cactaagctc cagtcagtca aaatgatcaa attattgaa    1200 gagaataagc aattctgttc tttattagga cacagtagat acagactaca aagtggagtg    1260
tgcttaataa gaggtagcat ttgttaagtg tcaattactc tattatccct tggagcttct    1320
```

| | |
|---|---|
| caaaataacc atataaggtg taagatgtta aaggttatgg ttacactcag tgcacaggta | 1380 |
| agctaatagg ctgagagaag ctaaattact tactggggtc tcacagtaag aaagtgagct | 1440 |
| gaagtttcag cccagattta actggattct gggctcttta ttcatgttac ttcatgaatc | 1500 |
| tgtttctcaa ttgtgcagaa aaaggggggc tatttataag aaaagcaata aacaaacaag | 1560 |
| taatgatctc aaataagtaa tgcaagaaat agtgagattt caaaatcagt ggcagcgatt | 1620 |
| tctcagttct gtcctaagtg gccttgctca atcacctgct atcttttagt ggagctttga | 1680 |
| aattatgttt cagacaactt cgattcagtt ctagaatgtt tgactcagca aattcacagg | 1740 |
| ctcatctttc taacttgatg gtgaatatgg aaattcagct aaatggatgt taataaaatt | 1800 |
| caaacgtttt aaggacagat ggaaatgaca gaattttaag gtaaaatata tgaaggaata | 1860 |
| taagataaag gattttcta ccttcagcaa aaacataccc actaattagt aaaattaata | 1920 |
| ggcgaaaaaa agttgcatgc tcttatactg taatgattat catttttaaaa ctagcttttt | 1980 |
| gccttcgagc tatcggggta aagacctaca ggaaaactac tgtcgaaatc ctcgagggga | 2040 |
| agaaggggga ccctggtgtt tcacaagcaa tccagaggta cgctacgaag tctgtgacat | 2100 |
| tcctcagtgt tcagaagttg aatgcatgac ctgcaatggg gagagttatc gaggtctcat | 2160 |
| ggatcataca gaatcaggca agatttgtca gcgctgggat catcagacac cacaccggca | 2220 |
| caaattcttg cctgaaagat atcccgacaa gggctttgat gataattatt gccgcaatcc | 2280 |
| cgatggccag ccgaggccat ggtgctatac tcttgaccct cacacccgct gggagtactg | 2340 |
| tgcaattaaa acatgcgctg acaatactat gaatgacact gatgttcctt tggaaacaac | 2400 |
| tgaatgcatc caaggtcaag gagaaggcta caggggcact gtcaatacca tttggaatgg | 2460 |
| aattccatgt cagcgttggg attctcagta tcctcacgag catgacatga ctcctgaaaa | 2520 |
| tttcaagtgc aaggacctac gagaaaatta ctgccgaaat ccagatgggt ctgaatcacc | 2580 |
| ctggtgtttt accactgatc caaacatccg agttggctac tgctcccaaa ttccaaactg | 2640 |
| tgatatgtca catggacaag attgttatcg tgggaatggc aaaaattata tgggcaactt | 2700 |
| atcccaaaca gatctggac taacatgttc aatgtgggac aagaacatgg aagacttaca | 2760 |
| tcgtcatatc ttctgggaac cagatgcaag taagctgaat gagaattact gccgaaatcc | 2820 |
| agatgatgat gctcatggac cctggtgcta cacgggaaat ccactcattc cttgggatta | 2880 |
| ttgccctatt tctcgttgtg aaggtgatac cacacctaca atagtcaatt tagaccatcc | 2940 |
| cgtaatatct tgtgccaaaa cgaaacaatt gcgagttgta aatgggattc caacacgaac | 3000 |
| aaacatagga tggatggtta gtttgagata cagaaataaa catatctgcg gaggatcatt | 3060 |
| gataaaggag agttgggttc ttactgcacg acagtgtttc ccttctcgag acttgaaaga | 3120 |
| ttatgaagct tggcttggaa ttcatgatgt ccacggaaga ggagatgaga atgcaaaca | 3180 |
| ggttctcaat gtttcccagc tggtatatgg ccctgaagga tcagatctgg ttttaatgaa | 3240 |
| gcttgccagg cctgctgtcc tggatgattt tgttagtacg attgatttac ctaattatgg | 3300 |
| atgcacaatt cctgaaaaga ccagttgcag tgtttatggc tggggctaca ctggattgat | 3360 |
| caactatgat ggcctattac gagtggcaca tctctatata atgggaaatg agaaatgcag | 3420 |
| ccagcatcat cgagggaagg tgactctgaa tgagtctgaa atatgtgctg ggctgaaaa | 3480 |
| gattggatca ggaccatgtg agggggatta tggtggccca cttgtttgtg agcaacataa | 3540 |
| aatgagaatg gttcttggtg tcattgttcc tggtcgtgga tgtgccattc caatcgtcc | 3600 |
| tggtattttt gtccgagtag catattatgc aaaatggata cacaaaatta ttttaacata | 3660 |
| taaggtacca cagtcatag | 3679 |

<210> SEQ ID NO 14
<211> LENGTH: 2729
<212> TYPE: DNA
<213> ORGANISM: Artificial Sequence
<220> FEATURE:
<223> OTHER INFORMATION: nucleotide sequence of HGF-X8

<400> SEQUENCE: 14

| | | | | | | |
|---|---|---|---|---|---|---|
| atgtgggtga | ccaaactcct | gccagccctg | ctgctgcagc | atgtcctcct | gcatctcctc | 60 |
| ctgctcccca | tcgccatccc | ctatgcagag | ggacaaagga | aaagaagaaa | tacaattcat | 120 |
| gaattcaaaa | aatcagcaaa | gactacccta | atcaaaatag | atccagcact | gaagataaaa | 180 |
| accaaaaaag | tgaatactgc | agaccaatgt | gctaatagat | gtactaggaa | taaaggactt | 240 |
| ccattcactt | gcaaggcttt | tgtttttgat | aaagcaagaa | acaatgcct | ctggttcccc | 300 |
| ttcaatagca | tgtcaagtgg | agtgaaaaaa | gaatttggcc | atgaatttga | cctctatgaa | 360 |
| aacaaagact | acattagaaa | ctgcatcatt | ggtaaaggac | gcagctacaa | gggaacagta | 420 |
| tctatcacta | agagtggcat | caaatgtcag | ccctggagtt | ccatgatacc | acacgaacac | 480 |
| aggtaagaac | agtatgaaga | aaagagatga | agcctctgtc | ttttttacat | gttaacagtc | 540 |
| tcatattagt | ccttcagaat | aattctacaa | tcctaaaata | acttagccaa | cttgctgaat | 600 |
| tgtattacgg | caaggtttat | atgaattcat | gactgatatt | tagcaaatga | ttaattaata | 660 |
| tgttaataaa | atgtagccaa | acaatatct | taccttaatg | cctcaatttg | tagatctcgg | 720 |
| tatttgtgga | tccttatgtt | tcagacaact | tcgattcagt | tctagaatgt | ttgactcagc | 780 |
| aaattcacag | gctcatcttt | ctaacttgat | ggtgaatatg | gaaattcagc | taaatggatg | 840 |
| ttaataaaat | tcaaacgttt | taaggacaga | tgaaaatgac | agaattttaa | ggtaaaatat | 900 |
| atgaaggaat | ataagataaa | ggatttttct | accttcagca | aaacatacc | cactaattag | 960 |
| taaaattaat | aggcaaaaaa | aagttgcatg | ctcttatact | gtaatgatta | tcatttttaaa | 1020 |
| actagctttt | tgccttcgag | ctatcggggt | aaagacctac | aggaaaacta | ctgtcgaaat | 1080 |
| cctcgagggg | aagaaggggg | accctggtgt | tcacaagca | atccagaggt | acgctacgaa | 1140 |
| gtctgtgaca | ttcctcagtg | ttcagaagtt | gaatgcatga | cctgcaatgg | ggagagttat | 1200 |
| cgaggtctca | tggatcatac | agaatcaggc | aagatttgtc | agcgctggga | tcatcagaca | 1260 |
| ccacaccggc | acaaattctt | gcctgaaaga | tatcccgaca | agggctttga | tgataattat | 1320 |
| tgccgcaatc | ccgatggcca | gccgaggcca | tggtgctata | ctcttgaccc | tcacacccgc | 1380 |
| tgggagtact | gtgcaattaa | acatgcgct | gacaatacta | tgaatgacac | tgatgttcct | 1440 |
| ttggaaacaa | ctgaatgcat | ccaaggtcaa | ggagaaggct | acaggggcac | tgtcaatacc | 1500 |
| atttggaatg | gaattccatg | tcagcgttgg | gattctcagt | atcctcacga | gcatgacatg | 1560 |
| actcctgaaa | atttcaagtg | caaggaccta | cgagaaaatt | actgccgaaa | tccagatggt | 1620 |
| ctgaatcacc | ctggtgtttt | accactgatc | aaacatccg | agttggctac | tgctcccaaa | 1680 |
| ttccaaactg | tgatatgtca | catggacaag | attgttatcg | tgggaatggc | aaaaattata | 1740 |
| tgggcaactt | atcccaaaca | agatctggac | taacatgttc | aatgtgggac | aagaacatgg | 1800 |
| aagacttaca | tcgtcatatc | ttctgggaac | cagatgcaag | taagctgaat | gagaattact | 1860 |
| gccgaaatcc | agatgatgat | gctcatggac | cctggtgcta | cacgggaaat | ccactcattc | 1920 |
| cttgggatta | ttgccctatt | tctcgttgtg | aaggtgatac | cacacctaca | atagtcaatt | 1980 |
| tagaccatcc | cgtaatatct | tgtgccaaaa | cgaaacaatt | gcgagttgta | aatgggattc | 2040 |

```
caacacgaac aaacatagga tggatggtta gtttgagata cagaaataaa catatctgcg    2100
gaggatcatt gataaaggag agttgggttc ttactgcacg acagtgtttc ccttctcgag    2160
acttgaaaga ttatgaagct tggcttggaa ttcatgatgt ccacggaaga ggagatgaga    2220
aatgcaaaca ggttctcaat gtttcccagc tggtatatgg ccctgaagga tcagatctgg    2280
ttttaatgaa gcttgccagg cctgctgtcc tggatgattt tgttagtacg attgatttac    2340
ctaattatgg atgcacaatt cctgaaaaga ccagttgcag tgtttatggc tggggctaca    2400
ctggattgat caactatgat ggcctattac gagtggcaca tctctatata atgggaaatg    2460
agaaatgcag ccagcatcat cgagggaagg tgactctgaa tgagtctgaa atatgtgctg    2520
gggctgaaaa gattggatca ggaccatgtg aggggggatta tggtggccca cttgtttgtg    2580
agcaacataa aatgagaatg gttcttggtg tcattgttcc tggtcgtgga tgtgccattc    2640
caaatcgtcc tggtattttt gtccgagtag catattatgc aaaatggata cacaaaatta    2700
ttttaacata taaggtacca cagtcatag                                     2729
```

```
<210> SEQ ID NO 15
<211> LENGTH: 26
<212> TYPE: DNA
<213> ORGANISM: Artificial Sequence
<220> FEATURE:
<223> OTHER INFORMATION: forward primer

<400> SEQUENCE: 15
caaatgtcag ccctggagtt ccatga                                          26

<210> SEQ ID NO 16
<211> LENGTH: 26
<212> TYPE: DNA
<213> ORGANISM: Artificial Sequence
<220> FEATURE:
<223> OTHER INFORMATION: reverse primer

<400> SEQUENCE: 16
ctggattgct tgtgaaacac cagggt                                          26
```

GENE THERAPY FOR DIABETIC NEUROPATHY USING AN HGF ISOFORM

CROSS-REFERENCE TO RELATED APPLICATIONS

This application is a continuation of U.S. application Ser. No. 15/942,440, filed Mar. 31, 2018, which is a continuation of Ser. No. 14/355,792, filed May 30, 2014, which is a National Stage of International Application No. PCT/KR2012/002224, filed Mar. 27, 2012; which claims the benefit of KR Application No. 10-2011-0113786, filed Nov. 3, 2011, each of which is incorporated in its entirety by reference.

SEQUENCE LISTING

The instant application contains a Sequence Listing which has been submitted via EFS-Web and is hereby incorporated by reference in its entirety. Said ASCII copy, created on Mar. 30, 2018, is named 43077US_CRF_sequencelisting.txt, and is 77,473 bytes in size.

TECHNICAL FIELD

The present invention relates to a composition for the prevention or treatment of diabetic neuropathy, comprising, as active ingredients, different types of isoforms of hepatocyte growth factor (HGF) or at least one polynucleotide encoding the isoforms.

BACKGROUND ART

Hepatocyte growth factor (HGF) is a heparin-binding glycoprotein also known as scatter factor or hepatopoietin-A. HGF that has been first identified as a potent hepatotropic growth factor (Nakamura et al., Nature 342:440 (1989)) is a mesenchymal-derived heparin-binding protein having multiple biological effects such as mitogenesis, motogenesis, and morphogenesis of various types of cells. A gene encoding HGF is located at chromosome 7q21.1, and involves 18 exons and 17 introns (Seki T., et al., Gene 102:213-219 (1991)).

A transcript of about 6 kb is transcribed from the HGF gene, and then a full-length polypeptide HGF precursor (flHGF) composed of 728 amino acids is synthesized therefrom, wherein the flHGF includes the following domains: N-terminal hairpin loop-kringle 1-kringle 2-kringle 3-kringle 4-inactivated serine protease. Simultaneously, several other HGF polypeptide isoforms are synthesized by an alternative splicing of the HGF gene. Known isoforms include deleted variant HGF (deletion of five amino acids from kringle 1 of the full-length HGF), NK1 (N-terminal hairpin loop-kringle 1), NK2 (N-terminal hairpin loop-kringle 1-kringle 2), and NK4 (N-terminal hairpin loop-kringle 1-kringle 2-kringle 3-kringle 4). In addition, there are allelic variants of each isoform. The biologically inactive precursors may be converted into active forms of disulfide-linked heterodimer by protease in serum. In the heterodimers, the alpha chain having a high molecular weight forms four kringle domains and an N-terminal hairpin loop like a pre-activated peptide region of plasminogen. The kringle domains of a triple disulfide-bonded loop structure consisting of about 80 amino acids may play an important role in protein-protein interaction. The low-molecular weight beta chain forms an inactive serine protease-like domain. dHGF consisting of 723 amino acids is a polypeptide with deletion of five amino acids in the first kringle domain of the alpha chain, i.e., F, L, P, S and S, due to alternative splicing between exon 4 and exon 5.

In vivo, two isoforms of HGF (flHGF having 728 amino acids and dHGF having 723 amino acids) are generated through alternative splicing between exon 4 and exon 5. Both of flHGF and dHGF are the same in view of several biological functions, but are different from each other in terms of immunological characteristics and several biological characteristics. For example, flHGF exhibits about 20-fold, 10-fold and 2-fold higher activities than dHGF in terms of promoting DNA synthesis in human umbilical cord venous endothelial cell, arterial smooth muscle cell, and NSF-60 (murine myeloblast cell), respectively. dHGF exhibits about 3-fold and 2-fold higher activities than flHGF in terms of promoting DNA synthesis of LLC-PK1 (pig kidney epithelial cells), and OK (American opossum kidney epithelial cells), and mouse interstitial cells, respectively. In addition, flHGF exhibits 70-fold higher solubility in PBS than dHGF. Several anti-dHGF monoclonal antibodies recognize only dHGF and flHGF or a reduced form of dHGF, which implies that the three-dimensional structures of HGF and dHGF are different.

HGF has been shown to stimulate angiogenesis by regulating the growth of endothelial cells and migration of vascular smooth muscle cells. Due its angiogenic activity, HGF is regarded as one of the promising candidates in therapeutic angiogenesis. "Therapeutic angiogenesis" means an intervention that utilizes angiogenic factors as recombinant proteins or genes, for the treatment of ischemic diseases, such as coronary artery disease (CAD) or peripheral artery disease (PAD). HGF has been also known to stimulate not only the growth but also the migration of endothelial cells (Bussolino et al., J Cell Biol. 119:629 (1992); Nakamura et al., J Hypertens 14:1067 (1996)), and has been tested for its role as a re-endothelialization stimulating agent (Yasuda et al., Circulation 101:2546 (2000); Hayashi et al., Gene Ther 7:1664 (2000)). All of the studies on HGF gene therapy described above have been conducted by using flHGF cDNA encoding 728 amino acids, but not dHGF cDNA encoding 723 amino acids.

Diabetic Neuropathies are serious and dangerous diabetic complications, and, in many cases, they lead to simultaneous occurrence of several types of neuropathies. Diabetic neuropathies are largely classified into polyneuropathy and focal neuropathy. The polyneuropathy includes hyperglycemic neuropathy, distal symmetric polyneuropathy, autonomic neuropathy, acute sensory neuropathy, acute painful sensory neuropathy, chronic sensorimotor neuropathy, and the like. The focal neuropathy includes cranial neuropathy, truncal neuropathy, limb neuropathy, thoracolumbar radiculoneuropathy, lumbosacral radiculoplexus neuropathy, and the like (Andrew J. M. et al., Diabetescare 28:956-962 (2005); J Gareth Llewelyn et al., J Neurol Neurosurg Psychiatry 74:15-19 (2003)). Diabetic Neuropathy has severe pain and loss of mobility as its representative symptoms. According to statistics from the U.S., 60 to 70% of people with diabetes have been known to have diabetic neuropathy (American Diabetes Association (ADA), National Institute of Diabetes and Digestive and Kidney Disease (NIDDK)), and 3.9 million or more diabetic patients aged 40 or over have been known to have diabetic neuropathy. The economic cost of these is estimated to be up to $13.7 billion per year, and this cost is expected to increase continuously.

Currently permitted drugs for diabetic neuropathy are only Lyrica® of Pfizer and Cymbalta® of Eli Lilly. However, these two drugs are merely a kind of painkiller alleviating pains shown in diabetic neuropathy, and may not delay the progress of disease or fundamentally ameliorate symptoms. Besides this medicine treatment, allopathy for pain relief, motor function improvement, and mental stress reduction are being used. There is no fundamental treatment at present, and the control of diabetes through dietary control is the only way to minimize the occurrence of diabetic neuropathy. Therefore, new novel of therapeutic agents capable of suppressing or ameliorating the progress of diabetic neuropathy need to be developed.

Throughout this application, several patents and publications are referenced and citations are provided in parentheses. The disclosure of these patents and publications is incorporated into this application in order to more fully describe this invention and the state of the art to which this invention pertains.

DETAILED DESCRIPTION OF THE INVENTION

Technical Problem

The present inventors have endeavored to develop therapeutic agents capable of effectively treating diabetic neuropathy. As a result, the present inventors have found that the expression of different types of isoforms of hepatocyte growth factor (HGF) can effectively treat diabetic neuropathy, and then completed the present invention.

Therefore, the present invention has been made in view of the above-mentioned problems, and an aspect of the present invention is to provide a pharmaceutical composition for preventing or treating diabetic neuropathy.

Another aspect of the present invention is to provide a method for preventing or treating diabetic neuropathy.

Other purposes and advantages of the present disclosure will become clarified by the following detailed description of the invention, claims, and drawings.

Technical Solution

In accordance with an aspect of the present invention, there is provided a pharmaceutical composition for the prevention or treatment of diabetic neuropathy, the composition including, as active ingredients, different types of isoforms of hepatocyte growth factor (HGF) or at least one polynucleotide encoding the isoforms.

In accordance with another aspect of the present invention, there is provided a method for the prevention or treatment of diabetic neuropathy, the method including administering to a mammal a composition containing, as active ingredients, different types of isoforms of hepatocyte growth factor (HGF) or at least one polynucleotide encoding the isoforms.

The present inventors have endeavored to develop therapeutic agents capable of effectively treating diabetic neuropathy. As a result, the present inventors have found that the expression of different types of isoforms of hepatocyte growth factor (HGF) can effectively treat diabetic neuropathy.

The present invention is mainly characterized in that different types of isoforms of hepatocyte growth factor (HGF) or at least one polynucleotide sequence encoding the isoforms are used to prevent and treat diabetic neuropathy.

Treatment strategy of the present invention may be largely classified into two types: protein therapy and gene therapy.

According to the protein therapeutic agent strategy of the present invention, two or more types of isomeric proteins of HGF are used. The two or more types of isomeric proteins of HGF may be provided by one polypeptide or separate polypeptides. Preferably, the two or more types of isomeric proteins of HGF are provided by one polypeptide.

According to the gene therapeutic agent strategy of the present invention, at least one nucleotide sequence encoding two or more types of isomers of HGF is used. A polynucleotide sequence encoding two or more types of isomers of HGF may be provided by one polynucleotide or separate polynucleotides. Preferably, the polynucleotide sequence encoding two or more types of isomers of HGF is provided by one polynucleotide.

Hereinafter, the present invention will be described in detail.

As used herein, the term "isoform of HGF" refers to an HGF polypeptide having an amino acid sequence that is at least 80% identical to a naturally occurring HGF amino acid sequence in an animal, including all allelic variants. For example, the isoform of HGF has a meaning including all of normal forms or wild types of HGF and various variants of HGF (e.g., splice variants and deletion variants).

According to a preferable embodiment of the present invention, the different types of isoforms of HGF include two or more isoforms selected from the group consisting of full-length HGF, (flHGF), deleted variant HGF (dHGF), NK1, NK2, and NK4.

According to a more preferable embodiment of the present invention, the different types of isoforms of HGF of the present invention include flHGF and dHGF.

As used herein, the term "flHGF" refers to a sequence of amino acids 1-728 of the HGF protein from an animal, preferably a mammal, and more preferably a human. Human flHGF includes the amino acid sequence of SEQ ID NO: 1.

As used herein, the term "dHGF" refers to the deleted variant of the HGF protein produced by alternative splicing of the HGF gene from an animal, and preferably a mammal. More preferably, the term "dHGF" refers to human HGF with deletion of five amino acids (F, L, P, S, and S) in the first kringle domain of the alpha chain from the full length HGF sequence, consisting of 723 amino acids. The human dHGF includes the amino acid sequence of SEQ ID NO: 2.

As used herein, the term "NK1" refers to an isoform of HGF from an animal, preferably a mammal, and more preferably a human, consisting of the N-terminal hairpin loop and the kringle 1 domain. Human NK1 includes the amino acid sequence of SEQ ID NO: 3.

As used herein, the term "NK2" refers to an isoform of HGF from an animal, preferably a mammal, and more preferably a human, consisting of the N-terminal hairpin loop, the kringle 1 domain, and the kringle 2 domain. Human NK2 includes the amino acid sequence of SEQ ID NO: 4.

As used herein, the term "NK4" refers to an isoform of HGF from an animal, preferably a mammal, and more preferably a human, consisting of the N-terminal hairpin loop, the kringle 1 domain, the kringle 2 domain, the kringle 3 domain, and the kringle 4 domain. Human NK4 includes the amino acid sequence of SEQ ID NO: 5.

According to a preferable embodiment of the present invention, the different types of isoforms of HGF may be encoded by separate polynucleotides or a single polynucleotide. Herein, the different types of isoforms of HGF may include two or more polynucleotides when being encoded by separate polynucleotides, and the different types of isoforms of HGF may include at least one polynucleotide when being encoded by a single polynucleotide.

The polynucleotide of the present invention may be operatively linked to at least one regulatory sequence (e.g., a promoter or an enhancer) regulating expression of the isoforms of HGF.

When the two or more types of isoforms of HGF are encoded by separate polynucleotides, an expression cassette may be constructed in two manners. According to a first manner, the expression cassette is constructed by linking an expression regulatory sequence to a coding sequence (CDS) of each isoform. According to a second manner, the expression cassette is constructed by using an internal ribosomal entry site (IRES), like "expression regulatory sequence-CDS of first isomer-IRES-CDS of second isomer-transcription termination sequence". The IRES allows the gene translation to start at the IRES sequence, thereby resulting in the expression of two genes of interest in the same construct.

When two or more types of isoforms of HGF are encoded by a single polynucleotide, the polynucleotide encoding all the two or more types of isoforms of HGF is operatively linked to a single expression regulatory sequence.

Herein, the isoforms of HGF may be encoded by a hybrid HGF gene simultaneously expressing two or more different types of isoforms of HGF, e.g., flHGF and dHGF.

According to a preferable embodiment of the present invention, the hybrid HGF gene includes cDNA corresponding exon 1-18 of human HGF and intron 4 of a human HGF gene or its fragment, which is inserted between exon 4 and exon 5 of the cDNA.

According to a more preferable embodiment of the present invention, the hybrid HGF gene includes a nucleotide sequence selected from the group consisting of SEQ ID NO: 7 to SEQ ID NO: 14.

The hybrid HGF gene including intron 4 is 7112 bp long and includes the nucleotide sequence of SEQ ID NO: 7. The hybrid HGF gene may selectively include a fragment of intron 4 between exon 4 and exon 5 of HGF cDNA.

According to a preferable embodiment of the present invention, the sequence additionally inserted between exon 4 and exon 5 includes: intron 4 of the human HGF gene, nucleotides 392-2247, nucleotides 392-727, nucleotides 2229-5471, nucleotides 5117-5471, nucleotides 3167-5471, nucleotides 4167-5471, or a combination thereof, of SEQ ID NO: 7.

More preferably, the sequence additionally inserted between exon 4 and exon 5 of the therapeutic nucleotide sequence used in the present invention is (i) nucleotides 392-2247 and nucleotides 2229-5471 of SEQ ID NO: 7; (ii) nucleotides 392-2247 and nucleotides 5117-5471 of SEQ ID NO: 7; (iii) nucleotides 392-2247 and nucleotides 3167-5471 of SEQ ID NO: 7; (iv) nucleotides 392-2247 and nucleotides 4167-5471 of SEQ ID NO: 7; (v) nucleotides 392-727 and nucleotides 2229-5471 of SEQ ID NO: 7; (vi) nucleotides 392-727 and nucleotides 5117-5471 of SEQ ID NO: 7; (vii) nucleotides 392-727 and nucleotides 3167-5471 of SEQ ID NO: 7; or (viii) nucleotides 392-727 and nucleotides 4167-5471 of SEQ ID NO: 7.

The therapeutic nucleotide sequence of the present invention according to the sequence additionally inserted between exon 4 and exon 5 is summarized as below. (i) (exon 1 to exon 4)-(nucleotides 392-2247-nucleotides 2297-5471 of SEQ ID NO: 7)-(exon 5 to exon 18); (ii) (exon 1 to exon 4)-(nucleotides 392-2247-nucleotides 5117-5471 of SEQ ID NO: 7)-(exon 5 to exon 18); (iii) (exon 1 to exon 4)-(nucleotides 392-2247-nucleotides 3167-5471 of SEQ ID NO: 7)-(exon 5 to exon 18); (iv) (exon 1 to exon 4)-(nucleotides 392-2247-nucleotides 4167-5471 of SEQ ID NO: 7)-(exon 5 to exon 18); (v) (exon 1 to exon 4)-(nucleotides 392-727-nucleotides 2229-5471 of SEQ ID NO: 7)-(exon 5 to exon 18); (vi) (exon 1 to exon 4)-(nucleotides 392-727-nucleotides 5117-5471 of SEQ ID NO: 7)-(exon 5 to exon 18); (vii) (exon 1 to exon 4)-(nucleotides 392-727-nucleotides 3167-5471 of SEQ ID NO: 7)-(exon 5 to exon 18); and (viii) (exon 1 to exon 4)-(nucleotides 392-727-nucleotides 4167-5471 of SEQ ID NO: 7)-(exon 5 to exon 18).

Herein, the hybrid HGF gene including a fragment of intron 4 is named "HGF-X". The HGF-X includes HGF-X2, HGF-X3, HGF-X4, HGF-X5, HGF-X6, HGF-X7, and HGF-X8 having nucleotide sequences of SEQ ID NO: 8 to SEQ ID NO: 14, respectively.

The amino acid sequences and nucleotide sequences of HGF isoforms used in this invention may include amino acid sequences and nucleotide sequences substantially identical sequences to sequences of the wild type human HGF isoforms. The substantial identity includes sequences with at least 80% identity, more preferably at least 90% identity and most preferably at least 95% identity as measured using one of the sequence comparison algorithms where the amino acid sequence or nucleotide sequence of the wild type human HGF isoform is aligned with a sequence in the maximal manner. Methods of alignment of sequences for comparison are well-known in the art. Various programs and alignment algorithms are described in: Smith and Waterman, *Adv. Appl. Math.* 2: 482 (1981); *Needleman and Wunsch, J. Mol. Bio.* 48: 443 (1970); *Pearson and Lipman, Methods in Mol. Biol.* 24: 307-31 (1988); *Higgins and Sharp, Gene* 73: 237-44 (1988); *Higgins and Sharp, CABIOS* 5: 151-3 (1989) Corpet et al., *Nuc. Acids Res.* 16: 10881-90 (1988); Huang et al., *Comp. Appl. BioSci.* 8: 155-65 (1992); and Pearson et al., *Meth. Mol. Biol.* 24: 307-31 (1994). The NCBI Basic Local Alignment Search Tool (BLAST) [Altschul et al., *J. Mol. Biol.* 215: 403-10 (1990)] is available from several sources, including the National Center for Biological Information (NBCI, Bethesda, Md.) and on the Internet, for use in connection with the sequence analysis programs blastp, blasm, blastx, tblastn and tblastx. BLAST can be accessed at http://www.ncbi.nlm.nih.gov/BLAST/. A description of how to determine sequence identity using this program is available at http://www.ncbi.nlm.nih.gov/BLAST/blasthelp.html.

As used herein, the term "prevention" refers to all the acts of suppressing diabetic neuropathy or delaying the progress of diabetic neuropathy through administration of the composition of the present invention.

As used herein, the term "treatment" refers to (a) suppression of the development of diabetic neuropathy; (b) alleviation of diabetic neuropathy; and (c) removal of diabetic neuropathy.

About 15% of persons with diabetes show signs and symptoms of diabetic neuropathy, and among them, about 50% are found to have the traumatic damage of peripheral nerves on the electroneurography. Diabetic neuropathy is common among patients aged 50 or over, and various clinical subclass types are present. Pain is one of the common symptoms of diabetic neuropathy, and the frequency of pain varies depending on the patient.

According a preferable embodiment of the present invention, the composition of the present invention can prevent or treat diabetic neuropathy through the growth of neuronal cells or the suppression of neuronal cell death.

According to the present invention, when the PC12 neuronal cell line was treated with the isoforms flHGF and dHGF, the cell growth effect was 50% and 70% higher than those in control groups treated with flHGF and dHGF alone, respectively. In addition, when SH-SY5Y neuroblasts were treated with flHGF and dHGF, the cell growth effect was 25% and 80% higher than those in control groups treated with the isoforms flHGF and dHGF alone, respectively.

According to the present invention, when the PC12 neuronal cell line treated with high-concentration glucose was treated with the isoforms flHGF and dHGF, the apoptosis of neuronal cells by glucose was reduced by about 2 fold, and the effect of inhibiting apoptosis of neuronal cells was about 1.5-fold higher than that in the control group treated with flHGF.

According to the present invention, the safety of the isoforms of HGF and the pain reduction effects of the isoforms were confirmed through clinical trials in which the patients with diabetic neuropathy were injected with a polynucleotide expressing the isoforms flHGF and dHGF. Therefore, the composition of the present invention is useful to the prevention and the treatment of diabetic neuropathy.

According to a preferable embodiment of the present invention, diabetic neuropathies of the present invention are largely classified into polyneuropathy and focal neuropathy.

According to a preferable embodiment of the present invention, the polyneuropathy of the present invention includes one or more diseases selected from the group consisting of hyperglycemic neuropathy, distal symmetric polyneuropathy, autonomic neuropathy, acute sensory neuropathy, acute painful sensory neuropathy, and chronic sensorimotor neuropathy, and the focal neuropathy of the present invention includes one or more diseases selected from the group consisting of cranial neuropathy, truncal neuropathy, limb neuropathy, thoracolumbar radiculoneuropathy, and lumbosacral radiculoplexus neuropathy. However, they are not limited thereto.

The composition of the present invention may be applied in vivo through various delivery methods conventionally known in the field of gene therapy.

According to a preferable embodiment of the present invention, the polynucleotide of the present invention is naked DNA or contained in a gene carrier. Examples of the gene carrier include plasmid, vector, and viral vector.

(i) Plasmid (Vector)

Plasmids (vectors) may be used as a gene carrier for the polynucleotide of the present invention.

It is preferred that the polynucleotide in vectors is contained in a suitable expression construct. According the expression construct, it is preferred that the polynucleotide is operatively linked to a promoter. The term "operatively linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

According to the present invention, the promoter linked to the polynucleotide is operable in, preferably, animal, more preferably, mammalian cells, to control transcription of the polynucleotide, including the promoters derived from the genome of mammalian cells or from mammalian viruses, for example, CMV (cytomegalovirus) promoter, the adenovirus late promoter, the vaccinia virus 7.5K promoter, SV40 promoter, HSV tk promoter, RSV promoter, EF1 alpha promoter, metallothionein promoter, beta-actin promoter, human IL-gene promoter, human IFN gene promoter, human IL-4 gene promoter, human lymphotoxin gene promoter and human GM-CSF gene promoter, but not limited to. More preferably, the promoter useful in this invention is a promoter derived from the IE (immediately early) gene of human CMV (hCMV) or EF1 alpha promoter, most preferably hCMV IE gene-derived promoter/enhancer and 5'-UTR (untranslated region) comprising the overall sequence of exon 1 and exon 2 sequence spanning a sequence immeidately before the ATG start codon.

The expression cassette used in this invention may comprise a polyadenylation sequence, for example, including bovine growth hormone terminator (Gimmi, E. R., et al., Nucleic Acids Res. 17:6983-6998 (1989)), SV40-derived polyadenylation sequence (Schek, N, et al., Mol. Cell Biol. 12:5386-5393 (1992)), HIV-1 polyA (Klasens, B. I. F., et al., Nucleic Acids Res. 26:1870-1876 (1998)), β-globin polyA (Gil, A., et al, Cell 49:399-406 (1987)), HSV TK polyA (Cole, C. N. and T. P. Stacy, Mol. Cell. Biol. 5:2104-2113 (1985)) or polyoma virus polyA (Batt, D. B and G. G. Carmichael, Mol. Cell. Biol. 15:4783-4790 (1995)), but not limited to.

According to a preferable embodiment, the gene carrier for the polynucleotide includes pCK, pCP, pVAX1 and pCY vecors, more preferably pCK vector of which details are found in WO 2000/040737.

(ii) Retrovirus

Retroviruses capable of carrying relatively large exogenous genes have been used as viral gene delivery vectors in the senses that they integrate their genome into a host genome and have broad host spectrum.

In order to construct a retroviral vector, the polynucleotide of the invention is inserted into the viral genome in the place of certain viral sequences to produce a replication-defective virus. To produce virions, a packaging cell line containing the gag, pol and env genes but without the LTR (long terminal repeat) and Ψ components is constructed (Mann et al., *Cell*, 33:153-159(1983)). When a recombinant plasmid containing the polynucleotide of the invention, LTR and Ψ is introduced into this cell line, the Ψ sequence allows the RNA transcript of the recombinant plasmid to be packaged into viral particles, which are then secreted into the culture media (Nicolas and Rubinstein "Retroviral vectors," In: *Vectors: A survey of molecular cloning vectors and their uses*, Rodriguez and Denhardt (eds.), Stoneham: Butterworth, 494-513(1988)). The media containing the recombinant retroviruses is then collected, optionally concentrated and used for gene delivery.

A successful gene transfer using the second-generation retroviral vector has been reported. Kasahara et al. (*Science*, 266:1373-1376(1994)) prepared variants of moloney murine leukemia virus in which the EPO (erythropoietin) sequence is inserted in the place of the envelope region, consequently, producing chimeric proteins having novel binding properties. Likely, the present gene delivery system can be constructed in accordance with the construction strategies for the second-generation retroviral vector.

(iii) Adenovirus

Adenovirus has been usually employed as a gene delivery system because of its mid-sized genome, ease of manipulation, high titer, wide target-cell range, and high infectivity. Both ends of the viral genome contains 100-200 bp ITRs (inverted terminal repeats), which are cis elements necessary for viral DNA replication and packaging. The E1 region (E1A and E1B) encodes proteins responsible for the regulation of transcription of the viral genome and a few cellular genes. The expression of the E2 region (E2A and E2B) results in the synthesis of the proteins for viral DNA replication.

Of adenoviral vectors developed so far, the replication incompetent adenovirus having the deleted E1 region is usually used. The deleted E3 region in adenoviral vectors may provide an insertion site for transgenes (Thimmappaya, B. et al., *Cell,* 31:543-551(1982); and Riordan, J. R. et al., *Science,* 245:1066-1073(1989)). Therefore, it is preferred that the decorin-encoding nucleotide sequence is inserted into either the deleted E1 region (E1A region and/or E1B region, preferably, E1B region) or the deleted E3 region. The polynucleotide of the invention may be inserted into the deleted E4 region. The term "deletion" with reference to viral genome sequences encompasses whole deletion and partial deletion as well. In nature, adenovirus can package approximately 105% of the wild-type genome, providing capacity for about 2 extra kb of DNA (Ghosh-Choudhury et al., *EMBO J.,* 6:1733-1739(1987)). In this regard, the foreign sequences described above inserted into adenovirus may be further inserted into adenoviral wild-type genome.

The adenovirus may be of any of the 42 different known serotypes or subgroups A-F. Adenovirus type 5 of subgroup C is the most preferred starting material for constructing the adenoviral gene delivery system of this invention. A great deal of biochemical and genetic information about adenovirus type 5 is known. The foreign genes delivered by the adenoviral gene delivery system are episomal, and therefore, have low genotoxicity to host cells. Therefore, gene therapy using the adenoviral gene delivery system of this invention may be considerably safe.

(iv) AAV Vectors

Adeno-associated viruses are capable of infecting non-dividing cells and various types of cells, making them useful in constructing the gene delivery system of this invention. The detailed descriptions for use and preparation of AAV vector are found in U.S. Pat. Nos. 5,139,941 and 4,797,368.

Research results for AAV as gene delivery systems are disclosed in LaFace et al, *Viology,* 162:483486(1988), Zhou et al., *Exp. Hematol.* (NY), 21:928-933(1993), Walsh et al, *J. Clin. Invest.,* 94:1440-1448(1994) and Flotte et al., *Gene Therapy,* 2:29-37(1995). Recently, an AAV vector has been approved for Phase I human trials for the treatment of cystic fibrosis.

Typically, a recombinant AAV virus is made by cotransfecting a plasmid containing the gene of interest (i.e., decorin gene and nucleotide sequence of interest to be delivered) flanked by the two AAV terminal repeats (McLaughlin et al., 1988; Samulski et al., 1989) and an expression plasmid containing the wild type AAV coding sequences without the terminal repeats (McCarty et al., *J. Virol.,* 65:2942-2945(1991)).

(v) Other Viral Vectors

Other viral vectors may be employed as a gene delivery system in the present invention. Vectors derived from viruses such as vaccinia virus (Puhlmann M. et al., *Human Gene Therapy* 10:649-657(1999); Ridgeway, "Mammalian expression vectors," In: *Vectors: A survey of molecular cloning vectors and their uses.* Rodriguez and Denhardt, eds. Stoneham: Butterworth, 467-492(1988); Baichwal and Sugden, "Vectors for gene transfer derived from animal DNA viruses: Transient and stable expression of transferred genes," In: Kucherlapati R, ed. Gene transfer. New York: Plenum Press, 117-148(1986) and Coupar et al., *Gene,* 68:1-10(1988)), lentivirus (Wang G. et al., *J. Clin. Invest.* 104(11):R55-62(1999)) and herpes simplex virus (Chamber R., et al., *Proc. Natl. Acad. Sci USA* 92:1411-1415(1995)) may be used in the present delivery systems for transferring both the polynucleotide of the invention into cells.

(vi) Liposomes

Liposomes are formed spontaneously when phospholipids are suspended in an excess of aqueous medium. Liposome-mediated nucleic acid delivery has been very successful as described in Nicolau and Sene, *Biochim. Biophys. Acta,* 721:185-190(1982) and Nicolau et al., *Methods Enzymol.,* 149:157-176(1987). Example of commercially accessible reagents for transfecting animal cells using liposomes includes Lipofectamine (Gibco BRL). Liposomes entrapping polynucleotide of the invention interact with cells by mechanism such as endocytosis, adsorption and fusion and then transfer the sequences into cells.

Where the gene delivery system is a naked recombinant DNA molecule or plasmid, the polynucleotide sequence of the invention is introduced into cells by microinjection (Capecchi, M. R., *Cell,* 22:479(1980) and Harland and Weintraub, *J. Cell Biol.* 101:1094-1099(1985)), calcium phosphate co-precipitation (Graham, F. L. et al., *Virology,* 52:456(1973) and Chen and Okayama, *Mol. Cell. Biol.* 7:2745-2752(1987)), electroporation (Neumann, E. et al., *EMBO J.,* 1:841(1982) and Tur-Kaspa et al., *Mol. Cell Biol.,* 6:716-718(1986)), liposome-mediated transfection (Wong, T. K. et al., *Gene,* 10:87(1980) and Nicolau and Sene, *Biochim. Biophys. Acta,* 721:185-190(1982); and Nicolau et al., *Methods Enzymol.,* 149:157-176(1987)), DEAE-dextran treatment (Gopal, *Mol. Cell Biol.,* 5:1188-1190(1985)), and particle bombardment (Yang et al., *Proc. Natl. Acad. Sci.,* 87:9568-9572(1990)).

When the polynucleotide sequence of the present invention is constructed based on the viral vector, the polynucleotide sequence may be delivered into cells by various viral infection methods known in the art. The infection of host cells using viral vectors are described in the above-mentioned cited documents.

The pharmaceutical composition of the present invention may comprise a pharmaceutically acceptable carrier.

The pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

Preferably, the pharmaceutical composition of this invention may be administered parenterally. For non-oral administration, intravenous injection, intraperitoneal injection, intramuscular injection, subcutaneous injection, or local injection may be employed. For example, the pharmaceutical composition may be injected by retrograde intravenous injection.

Preferably, the pharmaceutical composition of the present invention may be administered into the muscle, and more preferably into the calf muscle.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition, and physicians of ordinary skill in the art can determine an effective amount of the pharmaceutical composition for desired treatment.

According to a preferable embodiment of the present invention, the isoforms of HGF of the present invention are administered at a dose of 1 µg to 100 mg for each, and the polynucleotide encoding the isoforms is administered at a dose of 1 µg to 40 mg. When the isoforms of HGF or the polynucleotide encoding the isoforms is repeatedly administered once or more, the dose may be equal or different for each administration.

According to the conventional techniques known to those skilled in the art, the pharmaceutical composition may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

Advantageous Effects

Features and advantages of the present invention are summarized as follows:

(a) The pharmaceutical composition of the present invention for preventing or treating diabetic neuropathy contains, as active ingredients, different types of isoforms of HGF or at least one polynucleotide encoding the isoforms.

(b) The present invention first established that the use of different types of isoforms of HGF or at least one polynucleotide expressing the isomers can treat diabetic neuropathy more effectively than the use of the full-length HGF.

(c) According to the present invention, diabetic neuropathy can be treated very effectively.

MODE FOR CARRYING OUT THE INVENTION

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Preparation of Plasmid DNA Expressing Isoforms of HGF

In order to carry out the following various experiments, the present inventors used the pCK vector as a vector capable of expressing isoforms of HGF. The pCK vector is constructed such that the expression of a subject to be expressed, e.g., an HGF gene, is regulated under enhancer/promoter of the human cytomegalovirus (HCMV), and is disclosed in detail in Lee et al., Biochem. Biophys. Res. Commun. 272:230 (2000); WO 2000/040737. Currently, the pCk vector is used for clinical trials on human body, and its safety and efficacy were confirmed (Henry et al., Gene Ther. 18:788 (2011)). In order to prepare plasmid DNAs expressing hybrid HGF genes as a therapeutic agent for diabetic neuropathy, the present inventors inserted each of the hybrid HGF genes into the pCK vector according to the method disclosed in U.S. Pat. No. 7,812,146.

Figure 1:
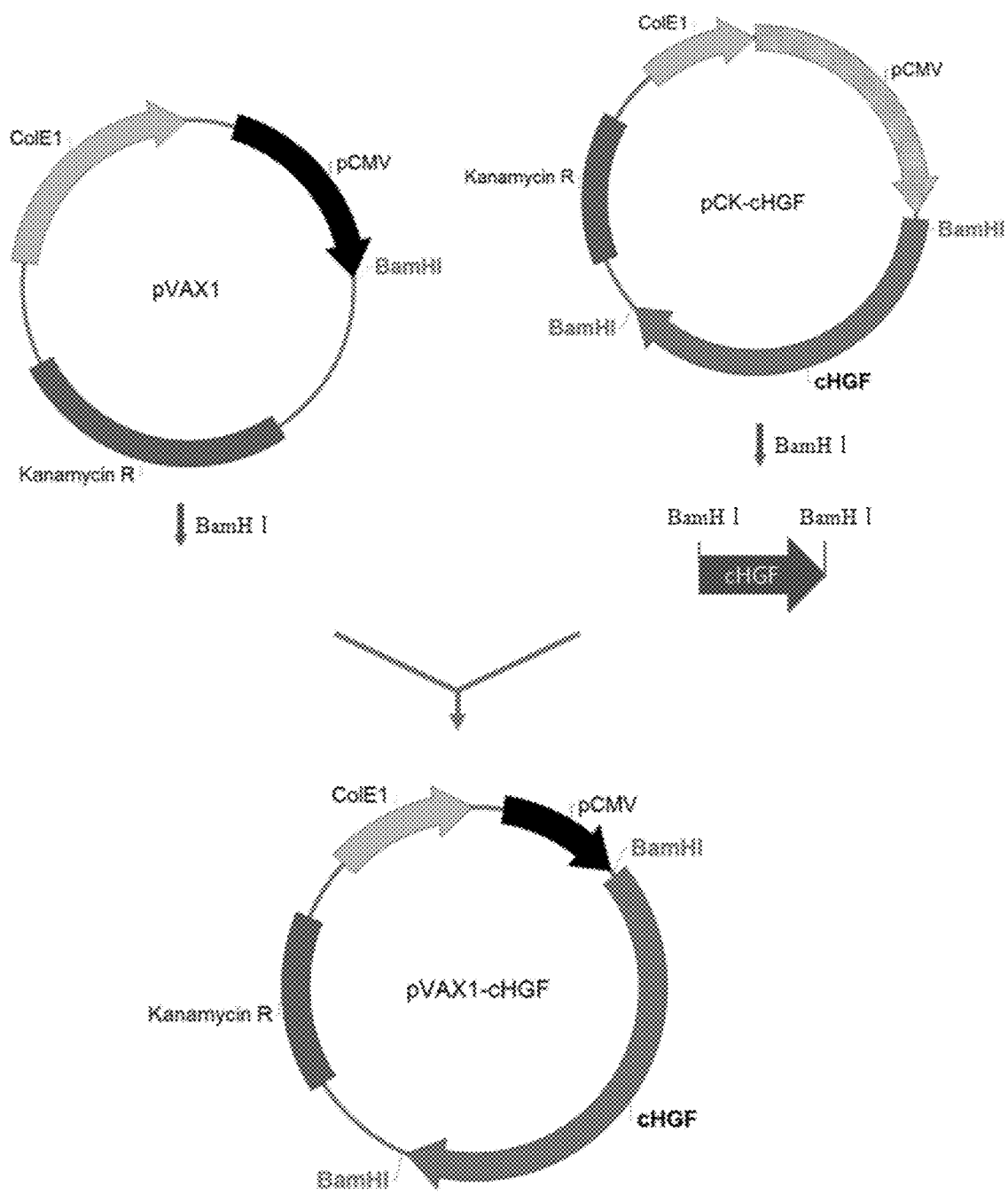
FIG. 1 is a diagram showing a procedure for constructing pVAX1-cHGF.
Figure 2:
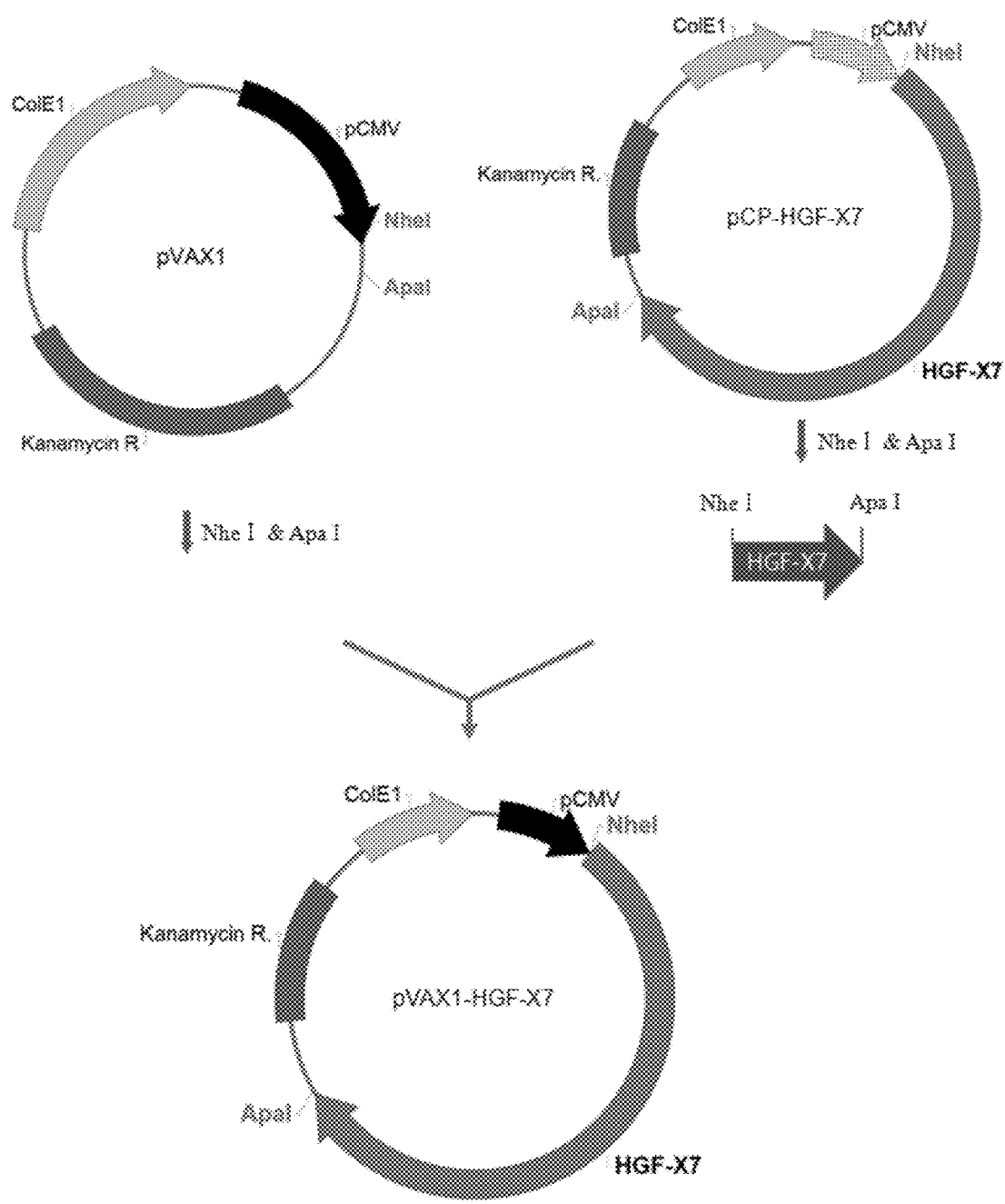
FIG. 2 is a diagram showing a procedure for constructing pVAX1-HGF-X7.

Example 2: Verification of Hybrid HGF Genes Co-Expressing Isoforms of HGF 2-1. Construction of Vector Expressing Isoforms of HGF In order to verify the expression of isoforms of HGF, gene expression vectors for cHGF (flHGF), dHGF, and a hybrid form thereof were prepared, and the HGF gene expressing vector was compared with the cHGF or dHGF expressing vector. The cHGF obtained by treating the pCK-cHGF disclosed in U.S. Pat. No. 7,812,146 with BamHI was inserted into the BamHI site of the pVAX1 (Invitrogen, USA) to construct pVAX1-cHGF (FIG. 1). The HGF-X7 obtained by treating the pCP-HGF-X7 with NheI and ApaI was inserted into the pVAX1 treated with the same enzymes to construct pVAX1-HGF-X7 (FIG. 2).

Figure 3:
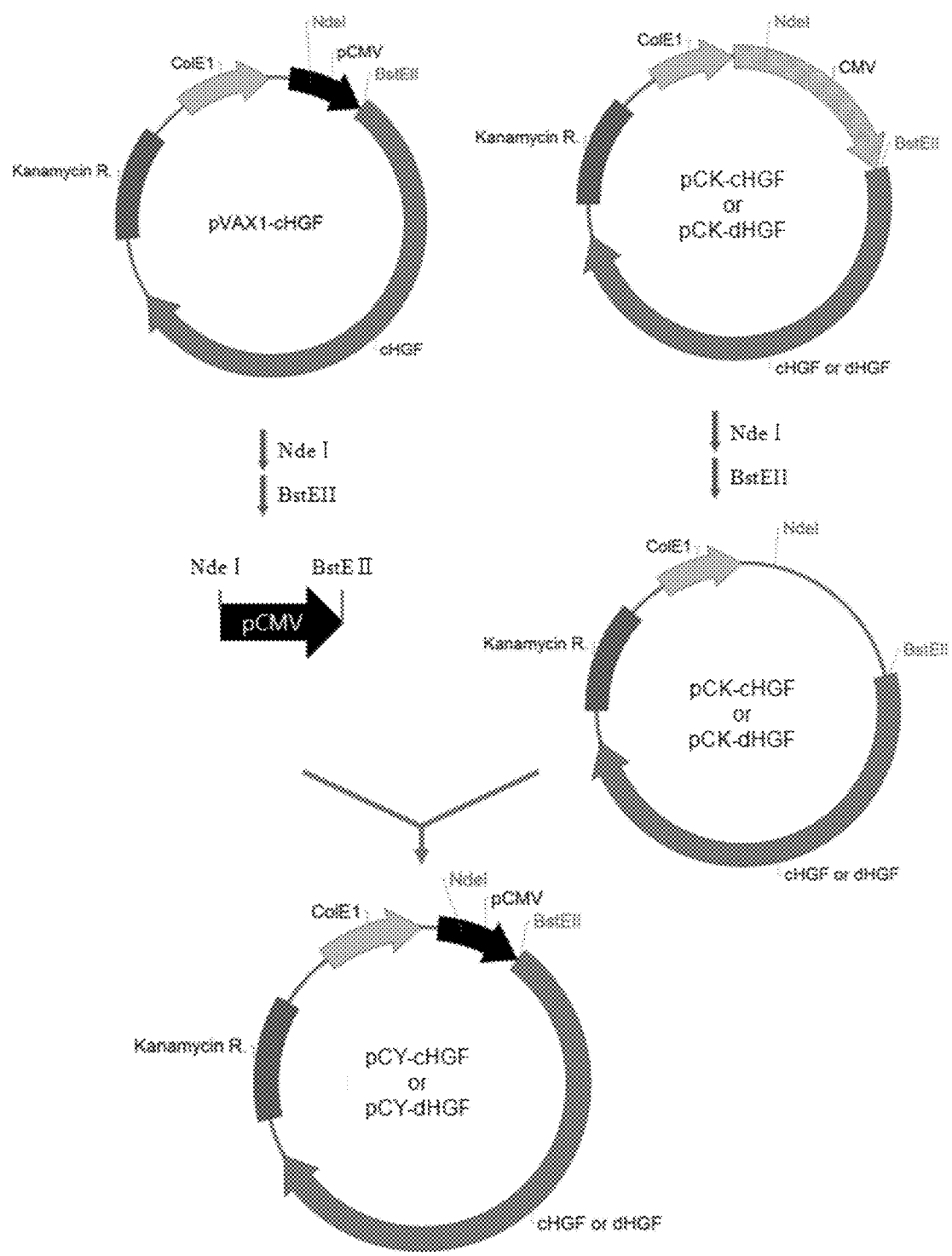
FIG. 3 is a diagram showing a procedure for constructing pCY-cHGF and pCY-dHGF.
Figure 4:
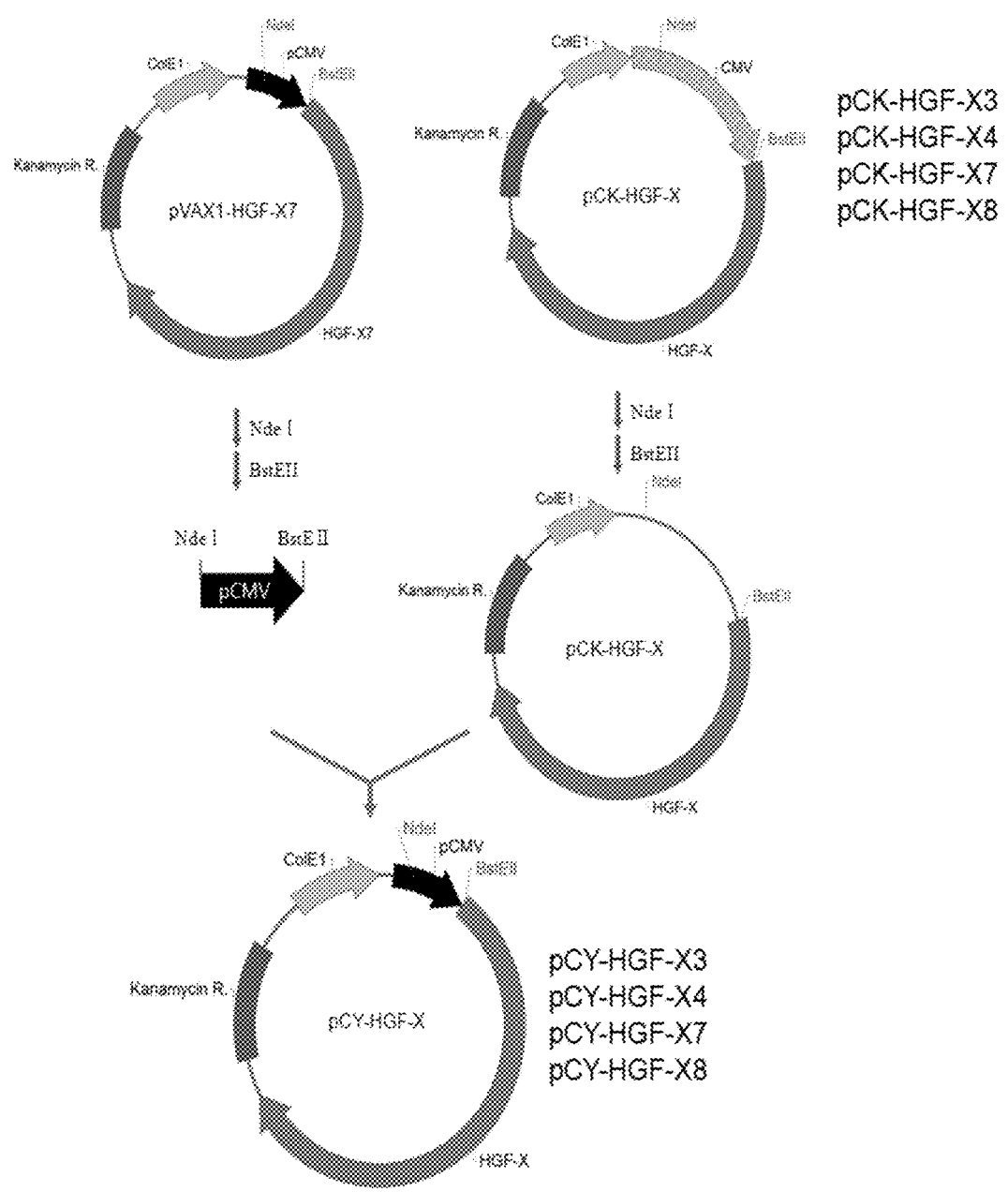
FIG. 4 is a diagram showing a procedure for constructing pCY-HGF-X3, pCY-HGF-X4, pCY-HGF-X7, and pCY-HGF-X8.
Figure 5:
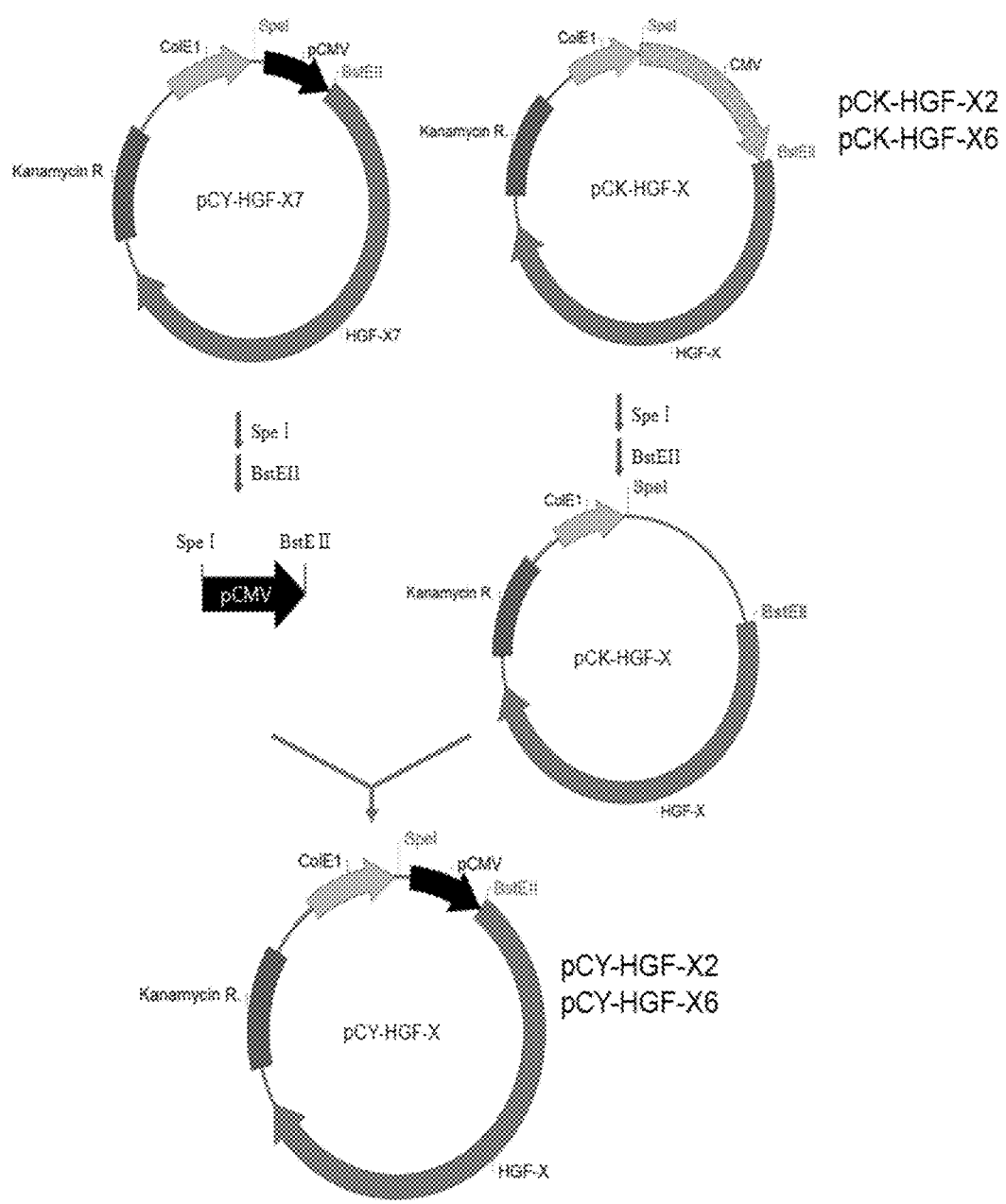
FIG. 5 is a diagram showing a procedure for constructing pCY-HGF-X2 and pCY-HGF-X6.
Figure 6:
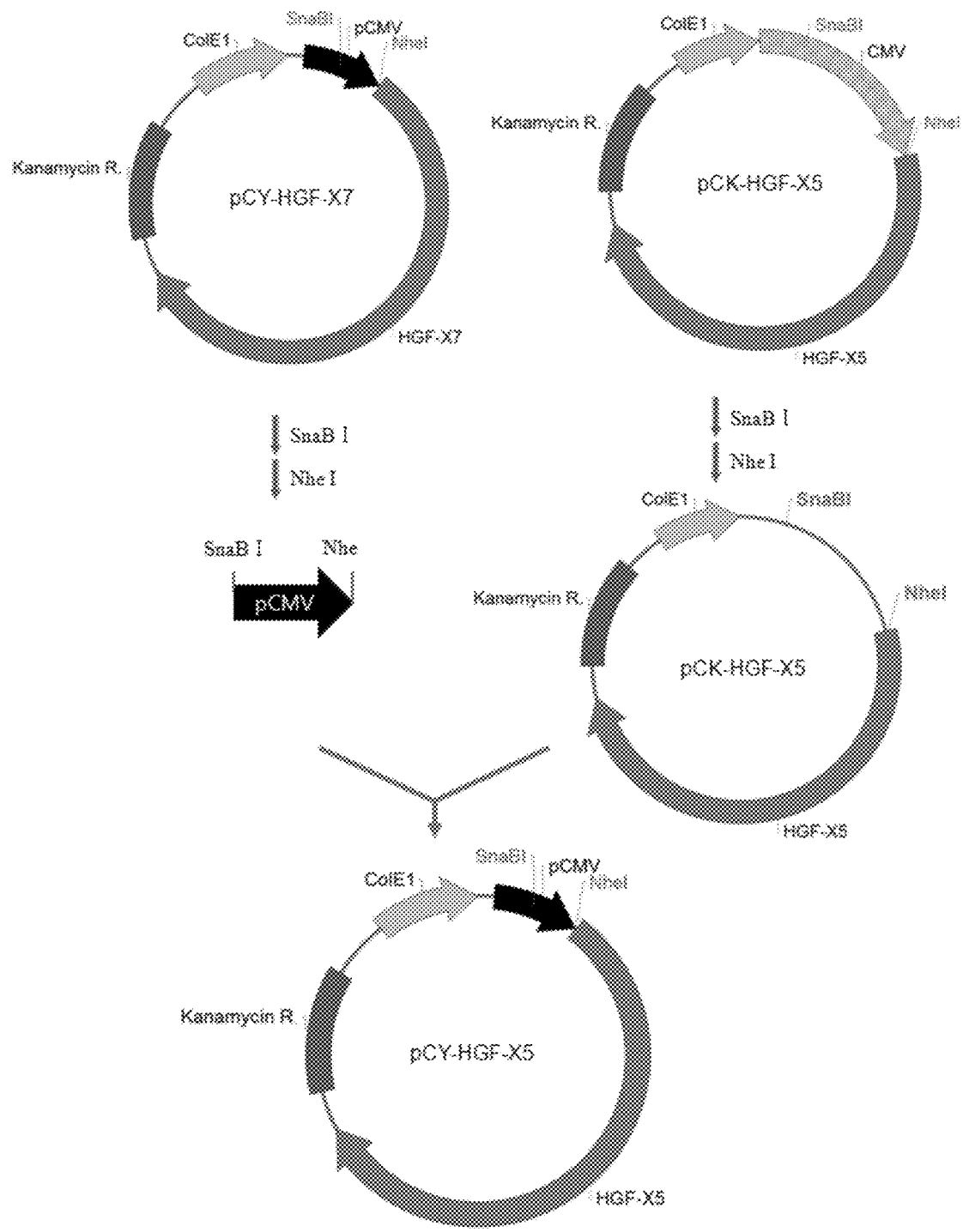
FIG. 6 is a diagram showing a procedure for constructing pCY-HGF-X5.

The promoter obtained by treating the pVAX1-cHGF with NdeI and BstEII was inserted into the pCK-cHGF and pCK-dHGF without promoters, respectively, which were obtained by treatment with the same enzymes, to construct new plasmids, pCY-cHGF and pCY-dHGF, using the term pCY, respectively (FIG. 3). The pVAX1-HGF-X7 was treated with NdeI and BstEII to obtain a promoter, which was then inserted into the pCK-HGF-X3, pCK-HGF-X4, pCK-HGF-X7, and pCK-HGF-X8 without promoters, respectively, which were obtained by treatment with the same enzymes, to construct pCY-HGF-X3, pCY-HGF-X4, pCY-HGF-X7, and pCY-HGF-X8, respectively (FIG. 4). The pCY-HGF-X7 was treated with SpeI and BstEII to obtain a promoter, which was then inserted into the pCK-HGF-X2 and pCK-HGF-X6 without promoters, respectively, which were obtained by treatment with the same enzymes, to construct pCY-HGF-X2 and pCY-HGF-X6, respectively (FIG. 5). The pCY-HGF-X7 was treated with SnaBI and NheI to obtain a promoter, which was then inserted into the pCK-HGF-X5 without promoters, which was obtained by treatment with the same enzymes, to construct pCY-HGF-X5 (FIG. 6).

2-2. Verification of RNA Expression of Isoforms of HGF

Each of the plasmid DNAs was transfected into $1 \times 10^6$ cells of 293T cells (ATCC CRL 1573) using FuGENE6 (Roche, USA) according to the manufacturer's instructions. At 48 hours after transfection, cells for each of the plasmids were harvested. RNA was extracted from the harvested 293T cells using the Trizol method (Trizol; Invitrogen, USA), and subjected to RT-PCR to obtain cDNA. PCR was conducted using the harvested cDNA as a template DNA and synthetic oligonucleotides of SEQ ID NO: 15 and SEQ ID NO: 16 as a primer pair. The PCR was conducted such that 3 µℓ of the template DNA, 1 µℓ each of 10 pmol/µℓ primer, 5 µℓ of 2.5 mM dNTP, 3.5 units of High fidelity enzyme mix (Roche, USA), and 5 µℓ of an enzyme buffer solution were mixed to prepare a total of 50 µℓ of a mixture liquid, which was then subjected to PCR amplification under conditions of 40 cycles of 30 seconds at 95°, 30 seconds at 60°, and 30 seconds at 72°. The thus amplified PCR products correspond to the boundary region between exon 4 and exon 5 of the HGF gene. Here, the nucleotide sequence of 142 bp is amplified for cHGF cDNA and the nucleotide sequence of 127 bp is amplified for dHGF cDNA.

Figure 7:
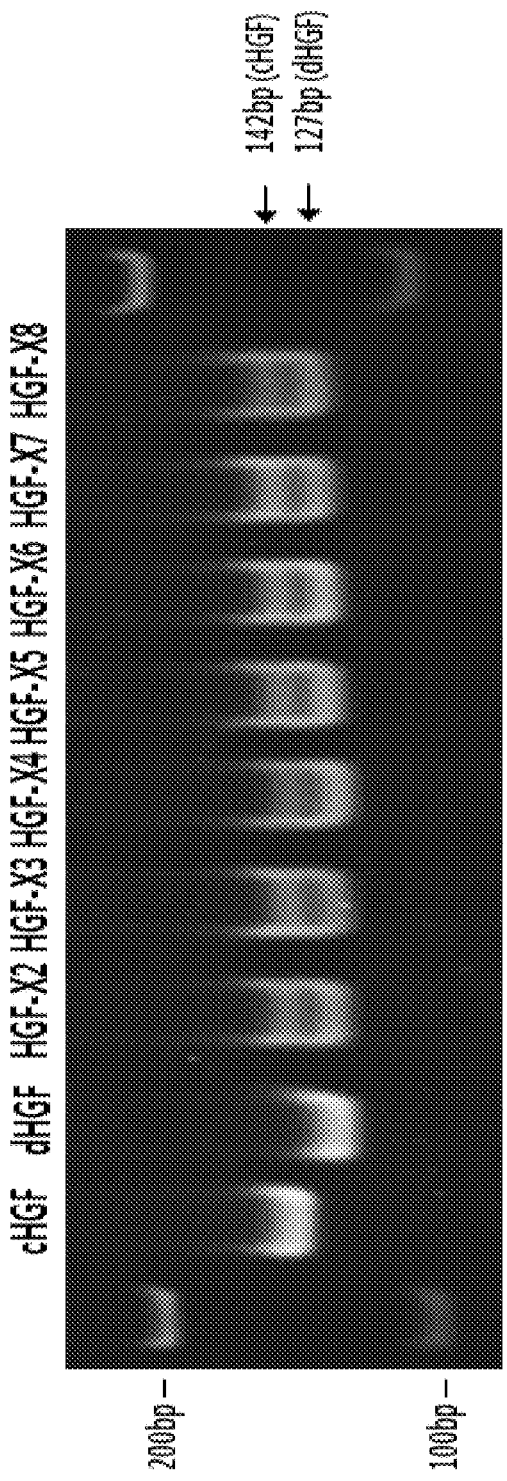
FIG. 7 shows results of RNA expression of respective isoforms of HGF.

As for the HGF-X gene, nucleotide sequences of at least 1 kb are amplified when the splicing does not occur, and both of the nucleotide sequences of 142 bp and 127 bp are amplified when alternative splicing occurs and thus cHGF and dHGF simultaneously are produced. The amplified PCR products were confirmed by electrophoresis on 15% polyacrylamide gels. As a result, the bands of 142 bp and 127 bp were detected for cHGF cDNA and dHGF cDNA, respectively, and both bands of 142 bp and 127 bp were detected for the hybrid HGF (FIG. 7).

2-3. Verification of Protein Expression of Isoforms of HGF

Each of the plasmid DNAs was transfected into $1 \times 10^6$ cells of 293T cells (ATCC CRL 1573) using FuGENE6 (Roche, USA) according to the manufacturer's instructions. At 48 hours after transfection, the supernatant of each of the plasmid DNAs was harvested. The amount of HGF protein in the supernatant was measured using an enzyme-linked immunosorbent assay (ELIS; R&D System, MN, USA). As a result, it was verified that, among the hybrid HGF genes, HGF-X7 showed the highest protein expression level.

Example 3: Effect of Hybrid HGF Expressed in pCK Vector on Growth and Survival of Neuronal Cells 3-1. Effect of Hybrid HGF on Growth of Neuronal Cells (1) Cell Line and Cell Culture Rat-derived P12 pheochromocytoma (CRL-1721; ATCC, MD, USA) was used in this experiment. P12 cells are commonly used in the research of diabetic neuropathy. It has been recently validated that glucose reduces neuritis of PC12 cells (Fan Zhang et al., THE JOURNAL OF PHARMACOLOGY AND EXPERIMENTAL THERAPEUTICS. 323:508-515 (2007)). In addition, it has been reported that glucose induces the reduction in proliferation of PC12 cells and DNA disruption, resulting in apoptosis of PC12 cells (EFRAT LELKES et al., Neurotoxicity research. 3:189-203 (2000)). PC12 cells were cultured in Dulbecco's Modified Eagle's medium (DMEM) supplemented with 15% fetal bovine serum and antibiotics under 37° and 5% $CO_2$. The cell culture medium, reagent, and serum were purchased from Gibco (Gibco BRL life technologies, inc., MD, USA), and plastic products for culture were purchased from BD Falcon (BD Falcon, NJ, USA).

(2) Preparation of Supernatants Containing Hybrid HGF Proteins and Recombinant Human HGF Protein Supernatants expressing hybrid HGF proteins, that is, HGF-X2, HGF-X3, HGF-X4, HGF-X5, HGF-X6, HGF-X7, and HGF-X8 were produced using DNA transfection. The transfection was conducted by using the Cellphect phosphate calcium transfection system (GE Healthcare BioSciences, NJ, USA) according to the manufacture's protocol. 293T cell lines seeded at $1 \times 10^6$ cells per well one day before were transfected with pCK, pCK-HGF-X2, pCK-HGF-X3, pCK-HGF-X4, pCK-HGF-X5, pCK-HGF-X6, pCK-HGF-X7, and pCK-HGF-X8, and then the cells were incubated for 48 hours. Upon the completion of culturing, the supernatants were all harvested, and then filtered through a 0.22-µm filter. The harvested protein supernatants were frozen at −80° before use.

Recombinant human HGF protein was purchased from R&D (R&D Systems, Inc., MSP, USA) for use.

(3) Verification of Protein Expression and Protein Quantification

In order to verify the expression of the respective proteins in the supernatants of 293T cells, the human HGF immunoassay by R&D (R&D Systems, Inc., MSP, USA) was used. The expression levels of the respective proteins were measured, and then the respective supernatants were again diluted to 1 µg/ml for the use of experiments.

(4) Comparison of Cell Growth Among Hybrid HGF Proteins in PC12 Cells

Figure 9:
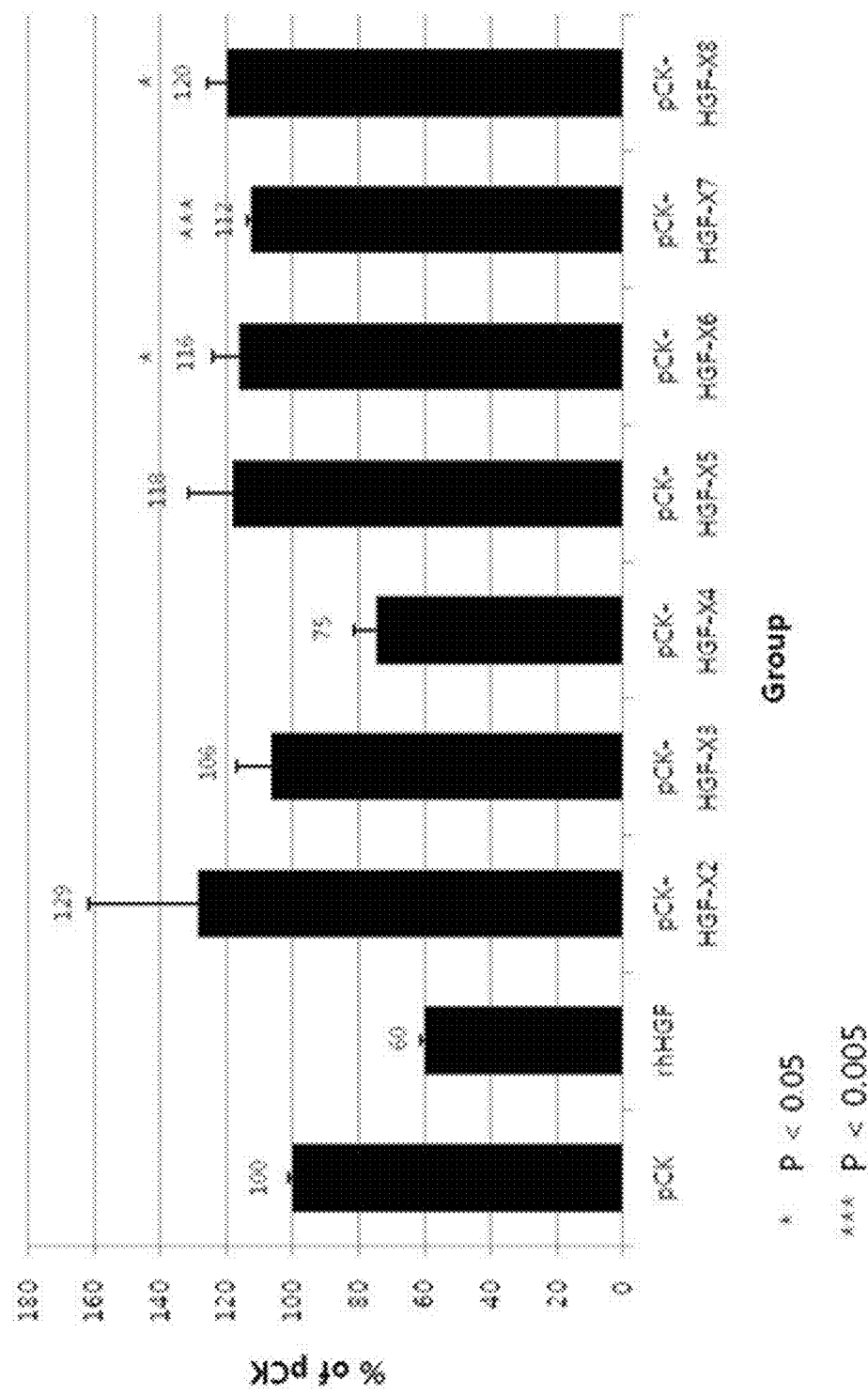
FIG. 9 shows effects of isoforms of HGF on the growth of PC12 cells.

In order to compare effects of hybrid HGF proteins on the growth of neuronal cells, the following experiment was conducted using PC12 cells. PC12 cells were seeded in a 6-well plate at $1 \times 10^5$ cells per well, and the next day, the medium was exchanged with a medium containing 1% FBS. The 293T cell supernatant expressing each protein was added thereto at a concentration of 5 ng/ml, followed by culturing for 7 days, and then cell counting was conducted. As control groups, the supernatant of 293T cells transfected with the pCK vector and the recombinant human HGF protein were used. As a result, all the experiment groups added with the supernatants expressing all the hybrid HGF proteins excluding HGF-X4 were observed to exhibit higher cell growth than the control groups. The experiment groups added with the supernatants expressing HGF-X6, HGF-X7, and HGF-X8 showed statistically significant differences as compared with the control group (pCK vector) (P<0.05 or P<0.005; FIG. 9).

Figure 8:
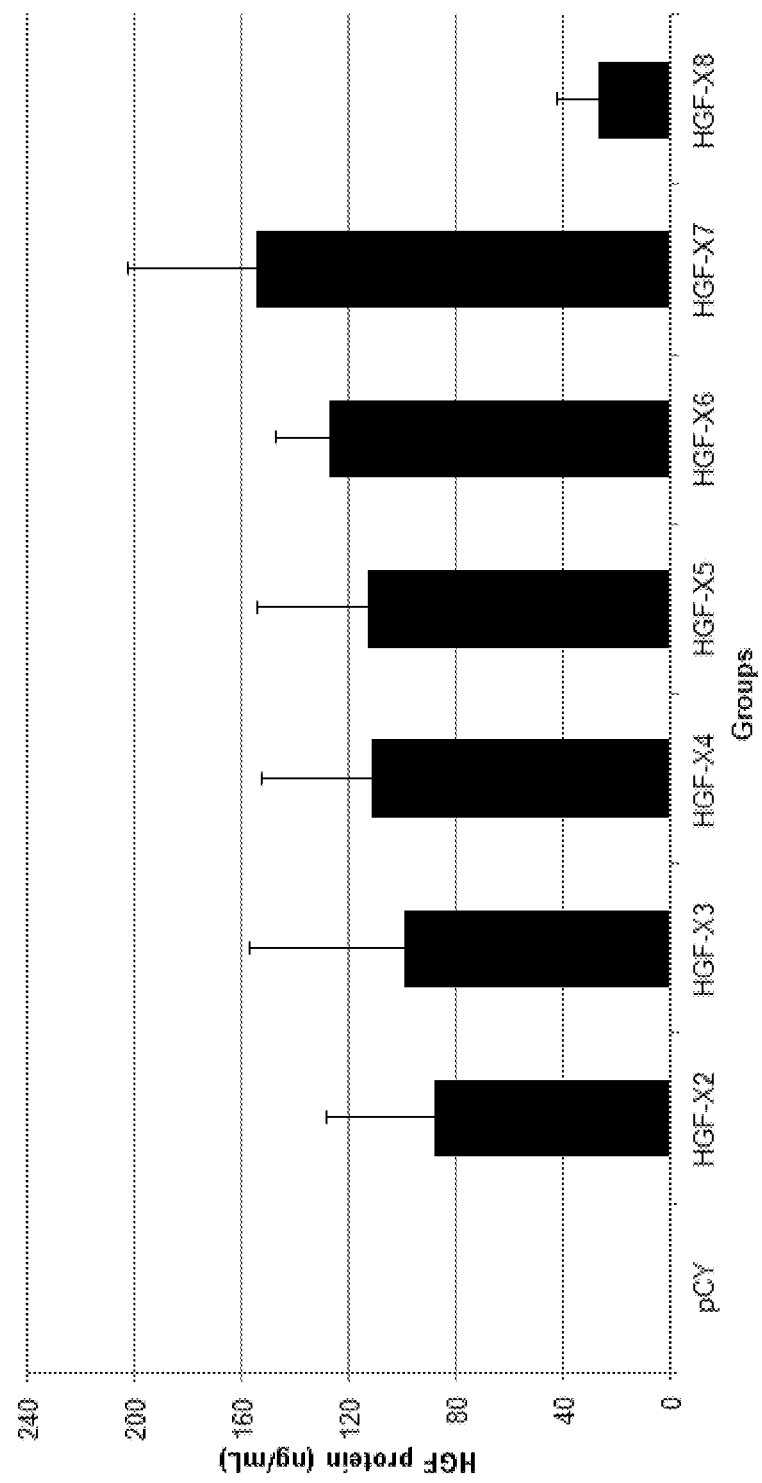
FIG. 8 shows results of protein expression of respective isoforms of HGF.

Since the pCK-HGF-X7 showed the highest gene expression level among the hybrid HGF genes (see, FIG. 8) and the distinctive statistical significance (P<0.005) in the growth of PC12 cells, the pCK-HGF-X7 was used in the following experiments and clinical trials.

3-2. Comparison Between Effects of HGF-X7 and cHGF on Growth of Neuronal Cells (1) Cell Line and Cell Culture Cell lines used in the present experiment were a total of two, PC12 cell line and human-derived SH-SY5Y neuroblasts (22266; KCLB, Korea). The SH-SY5Y cell line, like the PC12 cell line, is one of the most used cell lines for research of diabetic neuropathy. According to the study on diabetic neuropathy using SH-SY5Y cells, it has been known that glucose increases the depolarization of mitochondrial membranes of the SH-SY5Y cells and activates inactivated caspase-3, leading to apoptosis of the SH-SY5Y cells (G M Leinninger et al., Cell Death and Differentiation. 11:885-896 (2004)). All the cells were cultured under conditions of 37° and 5% $CO_2$. The PC12 cells were cultured in Dulbecco's Modified Eagle's medium (DMEM) supplemented with 15% fetal bovine serum and antibiotics, and the SH-SY5Y cells were cultured in Minimum Essential Medium (MEM) supplemented with 10% fetal bovine serum and antibiotics. The cell culture medium, reagent, and serum were purchased from Gibco and the ATCC (American Type Culture Collection, MD, USA).

(2) Production and Quantification of Supernatants Expressing HGF Proteins 293T cells were seeded at $1\times10^6$ cells, and the next day, the cells were transfected with pCK, pCK-cHGF, pCK-dHGF, and pCK-HGF-X7. After culturing for 48 hours, the supernatants were all harvested, and then filtered through a 0.22-μm filter. The expression levels of the HGF proteins contained in the respective supernatants were measured using human HGF immunoassay. The respective supernatants were again diluted to 1 μg/mℓ for the use of experiments.

(3) Comparison Between Growths of PC12 Cells by HGF-X7 and cHGF

In order to compare effects on the growth of neuronal cells, the cell proliferation degrees by the respective proteins were evaluated using PC12 cells. For achieving this, PC12 cells were seeded in a 6-well plate at $1\times10^5$ cells per well, and the next day, the medium was exchanged with a medium containing FBS. The respective proteins obtained from 293T cells transfected with pCK, pCK-cHGF, pCK-dHGF, and pCK-HGF-X7 were added thereto at concentrations of 5 ng/mℓ. The pCK vector was used for a control group.

Figure 10:
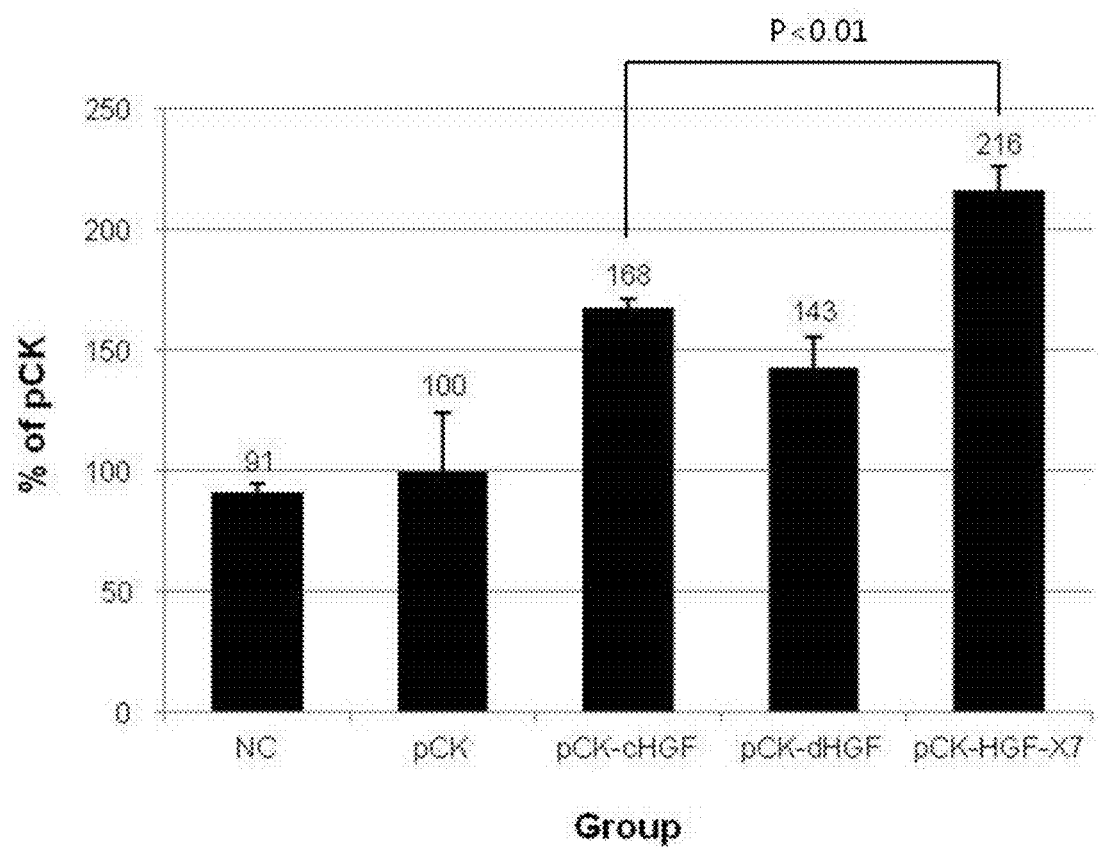
FIG. 10 shows an effect of pCK-HGF-X7 on the growth of PC12 cells.

As a result of cell counting after culturing for 7 days, the experiment group added with the supernatant of 293T cells containing HGF-X7 was verified to have the highest cell number. The experiment group added with HGF-X7 showed a cell growth effect, which was about 50% higher than that in cHGF and about 70% higher than that in dHGF (FIG. 10).

(4) Comparison Between Cell Growths of SH-SY5Y Cells by HGF-X7 and cHGF

In order to compare effects on the growth of neuronal cells, SH-SY5Y cells, the cell proliferation degrees by the respective proteins were measured. For achieving this, SH-SY5Y cell line was seeded in a 6-well plate at $5\times10^4$ cells per well. The next day, the medium was exchanged with a medium containing 1% FBS. The respective proteins obtained from 293T cells transfected with pCK, pCK-cHGF, pCK-dHGF, and pCK-HGF-X7 were added thereto at concentrations of 5 ng/mℓ. The pCK vector was used for a control group.

Figure 11:
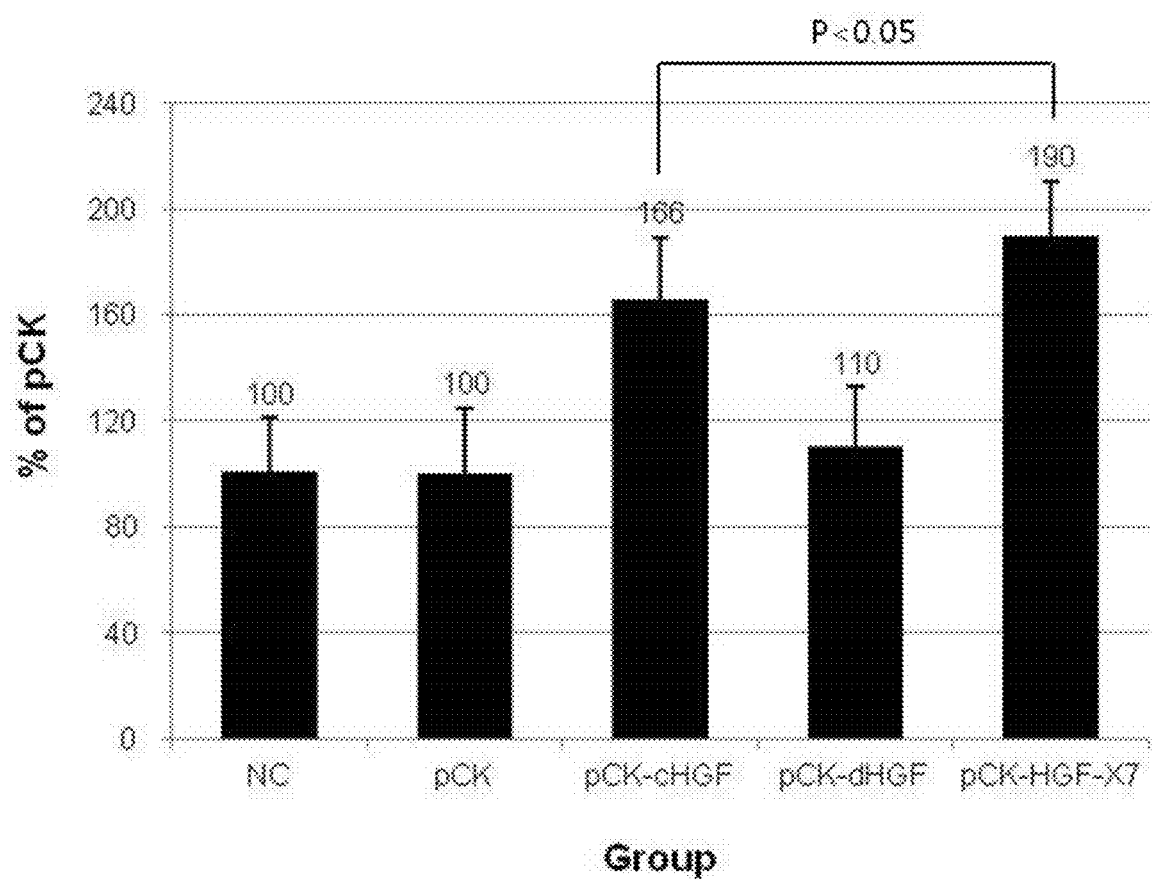
FIG. 11 shows an effect of pCK-HGF-X7 on the growth of SH-SY5Y cells.
Figure 12:
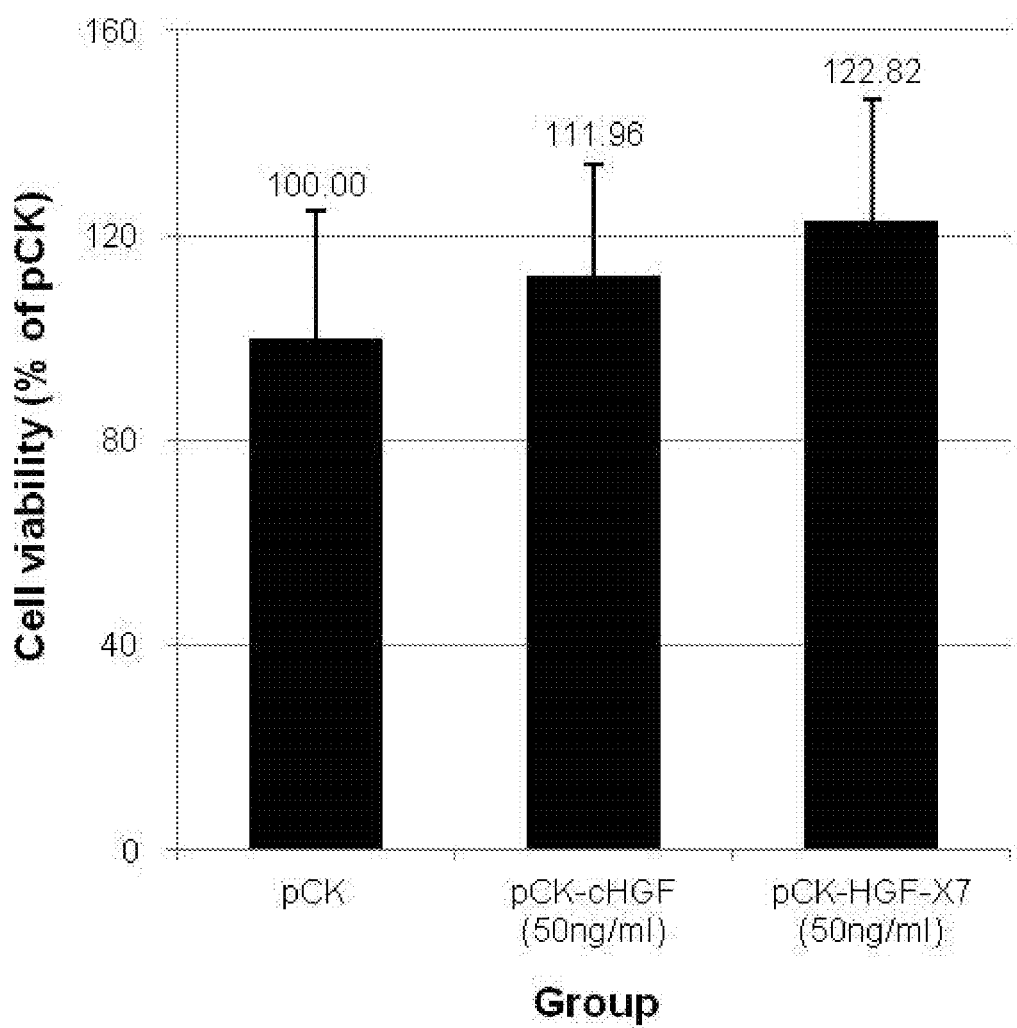
FIG. 12 shows an effect of pCK-HGF-X7 on PC12 cells that are growth-inhibited by high-concentration glucose.

As a result of cell counting after culturing for 7 days, the experiment group added with the supernatant of 293T cells containing HGF-X7 was verified to have the highest cell number. The experiment group added with HGF-X7 showed a cell growth effect, which was about 25% higher than that in cHGF and about 80% higher than that in dHGF (FIG. 11).

3-3. Effect of HGF-X7 on Growth of PC12 Cells in Culture Conditions of High-Concentration Glucose (1) Selection of Glucose Concentration and Culture Time for Inhibition of Growth of PC12 Cells Prior to the verification of an effect of HGF-X7 on the growth of PC12 cells under the culture conditions of high-concentration glucose, the glucose concentration and the culture time for inhibiting the growth of PC12 cells were selected. PC12 cells were seeded in a 96-well plate at $5\times10^4$ cells per well, and the next day, the medium was exchanged with 100 mM and 200 mM glucose media containing 1% FBS, respectively. As a control group, a medium containing 50 mM glucose, which was a culture medium of PC12 cells, was used. At 24, 48, and 72 hours after medium exchange, the cell growth was measured using the CellTiter-Glo Luminescent Cell Viability Assay (Promega, Wis., USA). The growth of PC12 cells was verified to be reduced in the high-concentration glucose medium. In particular, the growth of PC12 cells was observed to be reduced by about 50% in the 200 mM glucose medium at 48 hours and 72 hours. Based on these results, the glucose concentration and the culture time for inhibiting the growth of PC12 cells were selected to be 200 mM and 72 hours, respectively.

(2) Verification of Effect of HGF-X7 on Growth of PC12 Cells in Culture Conditions of High-Concentration Glucose The effect of HGF-X7 on the growth of PC12 cells in the culture conditions of high-concentration glucose was confirmed. PC12 cell line was seeded in a 96-well plate at $5\times10^4$ cells per well. The next day, the medium was exchanged with a 200 mM glucose medium, and then 50 ng/ml of the 293T cell supernatant expressing HGF-X7 was added thereto.

As a result of confirming the cell growth after culturing for 72 hours, it was observed that the experiment group added with the supernatant expressing HGF-X7 showed an increase by about 23% or more in cell growth as compared with the control group (pCK vector), and an increase by about 10% or more in cell growth as compared with the experiment group added with the same concentration of the supernatant containing cHGF.

3-4. Effect of HGF-X7 on Apoptosis Inhibitory Effect of PC12 Cells Under the Culture Conditions of High-Concentration Glucose (1) Selection of Glucose Concentration and Culturing Time for Inducing Apoptosis of PC12 Cells Prior to the estimation of an effect of HGF-X7 on apoptosis of PC12 cells under the culture conditions of high-concentration glucose, the glucose concentration and the culture time for inducing apoptosis of PC12 cells were selected. The PC12 cell line was seeded in a 6-well plate at $1\times10^5$ cells per well, and the next day, the medium for the PC12 cell line was exchanged with 50 mM, 100, mM, and 200 mM glucose media containing 1% FBS. The cells were cultured for 48 hours or 72 hours, and then all the cells were collected. The supernatants were removed by centrifugation for 3 minutes at 12000 rpm, followed by washing with PBS. This procedure was repeated once more. The degrees of apoptosis for the collected cells were measured using the Annexin V apoptosis assay system (BD Biosciences, NJ, USA). A 1× Annexin V binding buffer was put into the collected cells at a volume of 1 ml per $1\times10^6$ cells, so that the cells were suspended in the buffer. 5 μℓ of Annexin-V and a propidium iodide buffer were added to 100 μℓ of the suspended cells to stain the suspended cells for 20 minutes in the dark. 400 μℓ of a 1× Annexin V binding buffer was further added to the stained cells to detect apoptosis by flow cytometry.

As a result, the apoptosis of PC12 cells was not induced when the cells were cultured in the 100 mM glucose medium for 48 hours, as compared with the control group, but about 2.5-fold of apoptosis was induced in the 200 mM glucose medium as compared with the control group. Whereas, it was verified that, under the culture conditions for 72 hours, the apoptosis was induced in both 100 mM and 200 mM glucose media as compared with the control group, and the significant difference between 100 mM and 200 mM glucose media was not shown. Based on these results, the glucose concentration and the culture time for inducing apoptosis of PC12 cells were selected to be 200 mM and 48 hr, respectively.

(2) Effect of HGF-X7 on Apoptosis of PC12 Cells in Culture Conditions of High-Concentration Glucose The PC12 cell line was seeded in a 6-well plate at seeded in at $1 \times 10^5$ cells per well, and the next day, the medium for the PC12 cell line was exchanged with 200 mM glucose medium containing 1% FBS. 50 ng/ml of the 293T cell supernatant expressing cHGF or HGF-X7 was added thereto. As a control group, the supernatant of 293T cells transfected with the pCK vector was used. After culturing for 48 hours, all the cells were collected. Staining was conducted using the Annexin V apoptosis assay system, and then the degrees of apoptosis were confirmed by flow cytometry.

Figure 13:
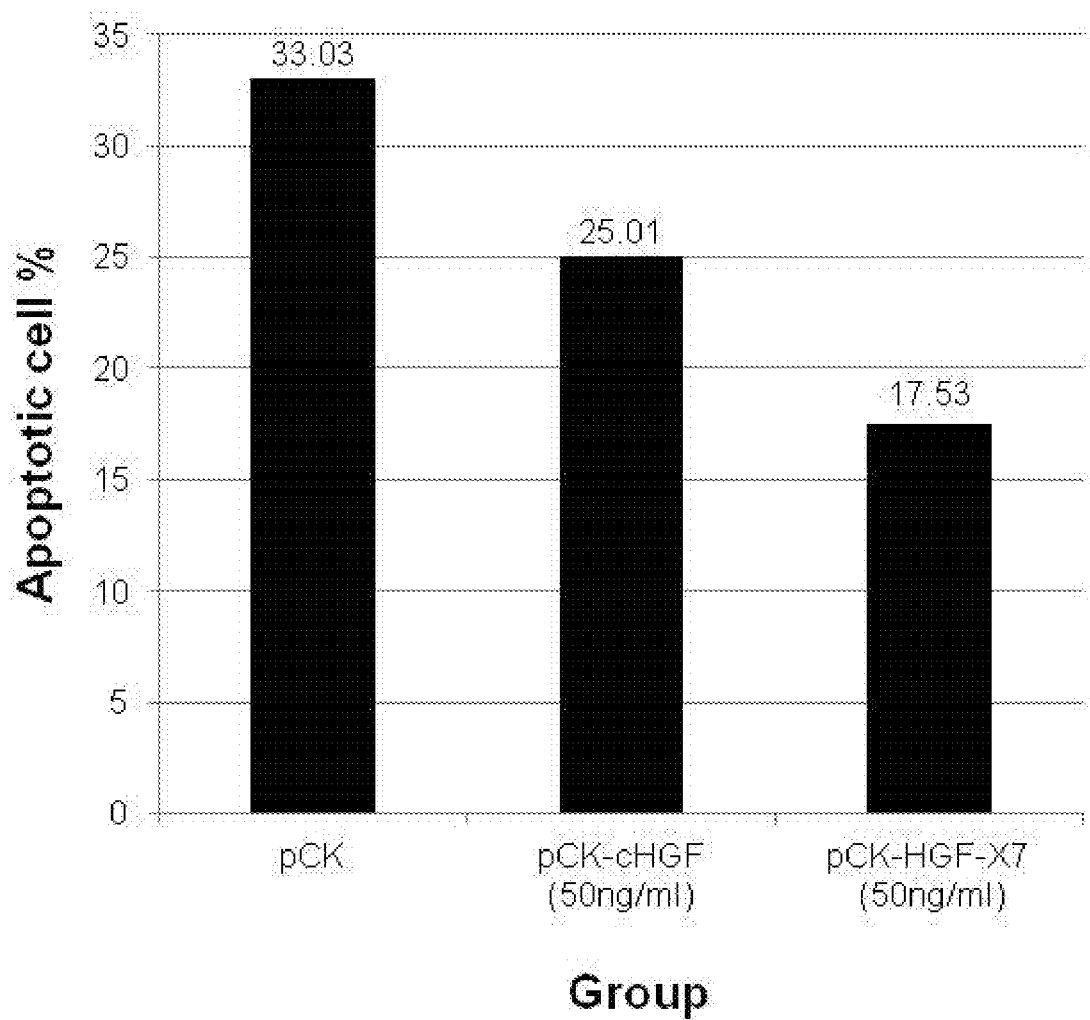
FIG. 13 shows an effect of pCK-HGF-X7 on apoptosis of PC12 cells, induced by high-concentration glucose.

As a result, the experiment group added with the 293T cell supernatant expressing HGF-X7 was verified to lead to a 2-fold decrease in apoptosis as compared with the control group added with the 293T cell supernatant expressing the pCK vector and show an apoptosis inhibitory effect of about 1.5 times or higher as compared with the experiment group added with the supernatant containing cHGF (FIG. 13).

Example 4: Clinical Trial of pCK-HGF-X7 Against Diabetic Neuropathy 4-1. Subjects and Administration A phase I clinical trial for safety and efficacy of pCK-HGF-X7 was conducted for 12 patients diagnosed with diabetic neuropathy. The time and dose of administration were different for three trial groups as shown in Table 1.

TABLE 1

| Trial group | Dose of administration | Number of times of administration | | Total dose of administration |
|---|---|---|---|---|
| | | Day 0 | Day 14 | |
| I | 4 mg | 8 | 8 | 8 ml |
| II | 8 mg | 16 | 16 | 16 ml |
| III | 16 mg | 32 | 32 | 32 ml |

4-2. Methods (1) Informed Consent Form and Screening Procedure

After receiving informed consent forms from patients, a screening procedure for checking the possibility of participating in the present clinical trial was conducted. The screening procedure was conducted within 30 days before day 0 of primary administration, and the possibility of participating in the present clinical trial was determined for each of the patients based on the following items.

a. complete medical history
b. complete physical exam
c. cancer screening tests
d. retinal fundoscopy
e. viral screening tests
f. hematology and serum chemistry
g. urinalysis
h. urine pregnancy test (for only females)
i. Ulcer screening (if possible)
j. ECG
k. Michigan Neuropathy Screening Instrument
l. Visual Analogue Scale (2) Administration of Trial Drug The pCK-HGF-X7 was injected in the right calf muscle of each of the subjects undergoing screening at an interval of two weeks (Day 0 and Day 14). The subjects assigned to trial group I were administered with 2 mg of pCK-HGF-X7 on Day 0, and again administered with 2 mg of pCK-HGF-X7 on Day 14. Therefore, trial group I was administered with a total of 4 mg of pCK-HGF-X7. On Day 0, each of the subjects was administered with 2 mg of pCK-HGF-X7, which was injected in eight sites of the calf muscle at a divided dose of 0.25 mg/0.5 ml/site. On Day 14, the administration was also conducted in the same manner. Trial group II was administered with a total of 8 mg of pCK-HGF-X7 (4 mg on Day 0 and 4 mg on Day 14). The administration was conducted similarly to trial group I. That is, on Day 0, each of the subjects of trial group II was administered with 4 mg of pCK-HGF-X7, which was injected in 16 sites of the calf muscle at a divided dose of 0.25 mg/0.5 ml/site. On Day 14, the administration was conducted in the same manner. Trial group III was administered with a total of 16 mg of pCK-HGF-X7 (8 mg on Day 0 and 8 mg on Day 14). On Day 0, each of the subjects of trial group III was administered with 8 mg of pCK-HGF-X7, which was injected in 32 sites of the calf muscle at a divided dose of 0.25 mg/0.5 ml/site. On Day 14, the injection in 32 sites was conducted in the same manner.

4-3. Clinical Evaluation Indicator

The primary endpoint of the present clinical trial is to confirm the safety of pCK-HGF-X7 injected in the calf muscle of each of the patients with diabetic neuropathy, and the secondary endpoint of the present clinical trial is to confirm the efficacy of pCK-HGF-X7 on pain, which is a main symptom of diabetic neuropathy.

(1) Safety Analysis

All the subjects administered with the trial drug in the present clinical trial are to be tested for safety analysis. Through follow-up observation of 12 months after administration, adverse event data (including adverse events and adverse events to stop administration of trial drug) were all recorded according to the extents thereof and relations with the trial drug. If possible, safety analysis was conducted through all statistical analysis. In addition, in order to avoid risks associated with cancers, all the subjects were screened by the method specified in the American Cancer Society Cancer Screening Guideline during the screening procedure.

(2) Pharmacokinetic Analysis

The level of HGF protein in serum of the subject and the amount of pCK-HGF-X7 in blood of the subject were measured before and after the administration of the trial drug of Day 0, and before and after the administration of the trial drug of Day 14, on Day 21, on Day 30, on Day 60, and on Day 90.

(3) Efficacy Analysis

Figure 14:
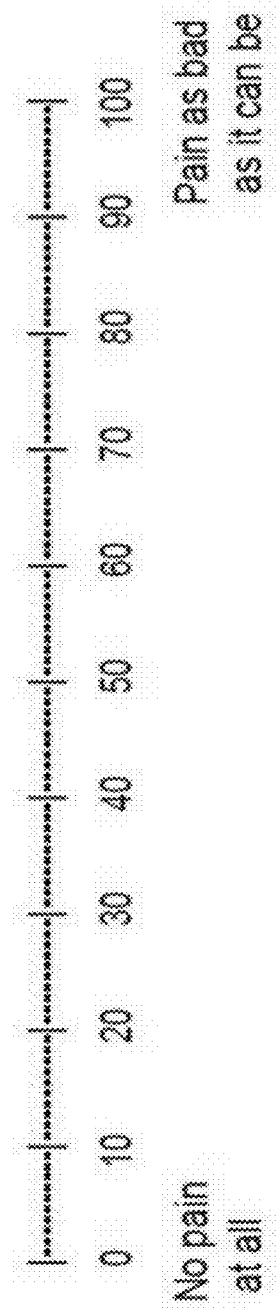
FIG. 14 is a diagram illustrating the visual analogue scale (VAS) estimation.

A visual analogue scale (VAS) method was used to record the change in pain for all the subjects. According to the VAS method, the individual preference for a health state was directly measured. That is, each of the subjects is allowed to directly score a scale for the severity of pain. A 100 mm-long line was drawn, and "No pain at all" was marked at one side of the line and "Pain as bad as it can be" was marked at the other side of the line. Then, the subjects are allowed to determine and record the severity of pain by themselves according to the VAS indicator. This method cannot show the comparison between different subjects, but can show the change in the severity of pain for the same subject (FIG. 14). In order to deduce clinically significant results, the safety analysis was conducted through every possible statistical analysis.

4-4. Results (1) Safety Results (Adverse Event Report)

As for the adverse events due to administration of pCK-HGF-X7 of the present invention, seven adverse events occurred in a total of three subjects of trial group I; two adverse events occurred in two subjects of trial group II; and two adverse events occurred in two subjects of trial group III. The adverse events were reported to be dry eyes, injection site pain, dry mouth, diarrhea, and the like in trial group I; back pain and sinusitis in trial group II; and right rib pain and viral syndrome in trial group III. The number of adverse drug events was five, which were reported in two subjects of trial group I, dry eyes (two events), injection site pain, dry mouth, and diarrhea, but they correspond to mild adverse drug events and thus recovered soon. Whereas, no serious adverse events were reported.

(2) Pharmacodynamics (PD) Results

Figure 15:
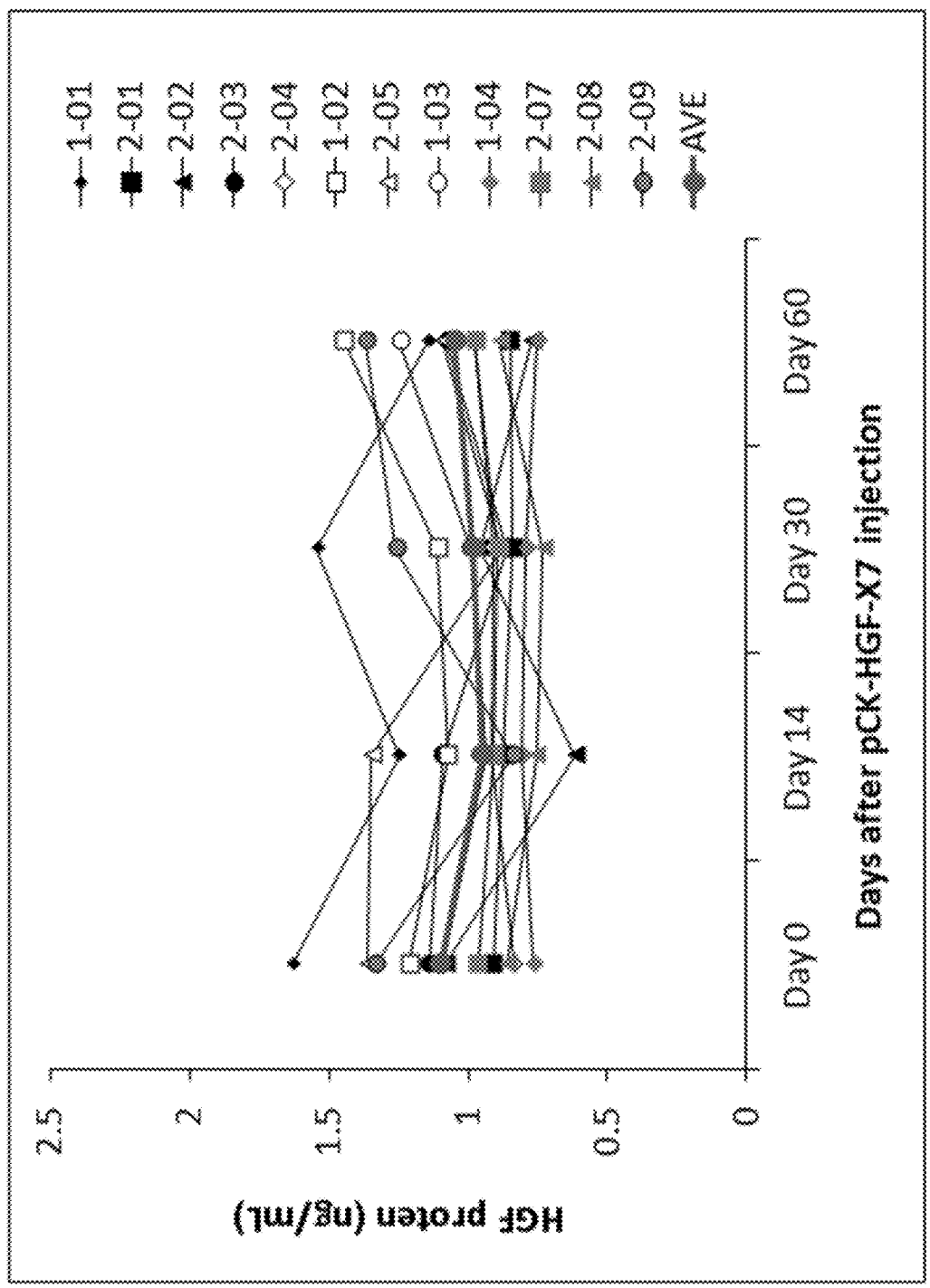
FIG. 15 shows results of pharmacodynamics of pCK-HGF-X7.

As a result of confirming the amount of HGF protein produced in serum after administration of pCK-HGF-X7, it was verified that the level of HGF protein in serum after administration of pCK-HGF-X7 was not increased but maintained during the clinical trial (FIG. 15).

(3) Pharmacokinetics (PK) Results

As a result of confirming the amount of pCK-HGF-X7 remaining after pCK-HGF-X7 treatment, the pCK-HGF-X7 DNA was not detected in ten subjects during follow-up observation of 60 days, and was detected at under 100 copies/mℓ for all the subjects (Table 2).

Figure 17:
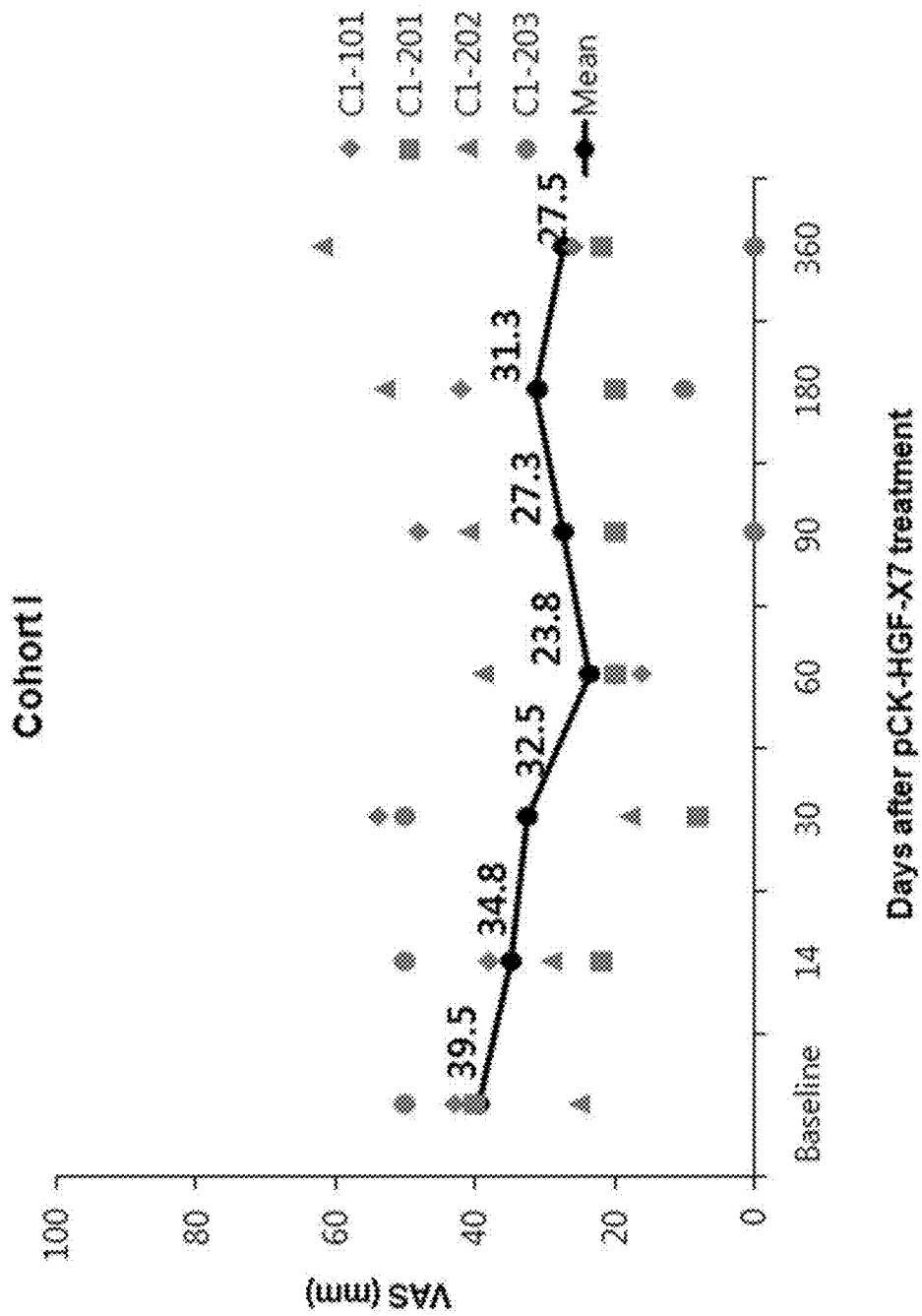
FIG. 17 shows results of efficacy of pCK-HGF-X7 in a first dose group (4 mg).

In the case of the first dose group (4 mg), the mean baseline VAS value was 39.5, and the mean VAS value at two months after treatment was 23.8, which showed a 39.7% reduction in the pain VAS value, but the mean VAS value at six months after treatment was 31.3, which merely showed a 20.8% reduction in the pain VAS value as compared with the baseline value. In the first dose group, the pain reduction was observed in three of four subjects and the pain reduction of 50% or higher was observed in two of four subjects (FIG. 17).

Figure 18:
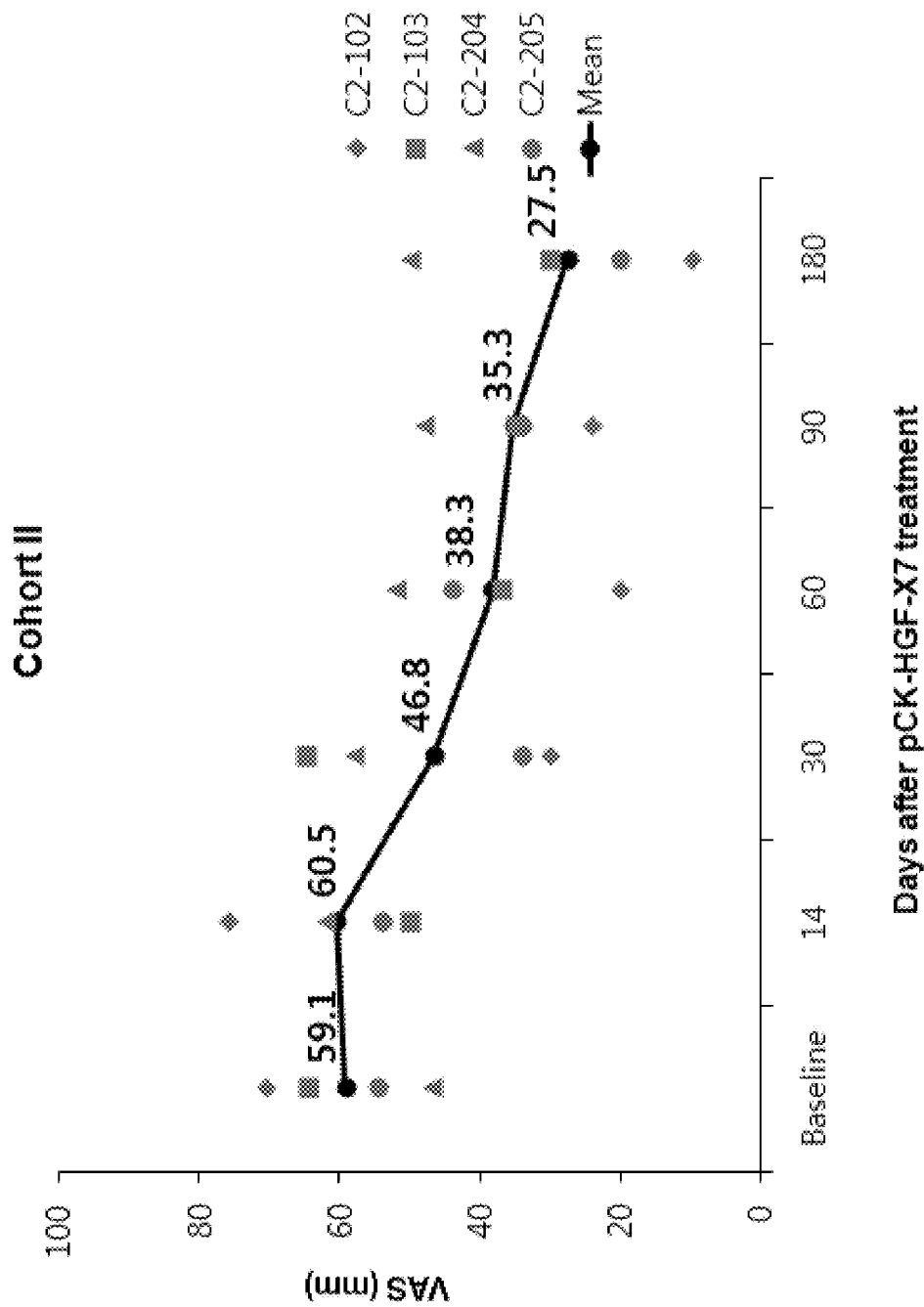
FIG. 18 shows results of efficacy of pCK-HGF-X7 in a second dose group (8 mg).

In the case of the second dose group (8 mg), the mean baseline VAS value was 59.1, and the VAS value from one month after treatment was sharply reduced and the mean VAS value at six months after treatment was 27.5, which showed a 53.5% reduction in the pain VAS value as compared with the baseline value (FIG. 18).

Figure 19:
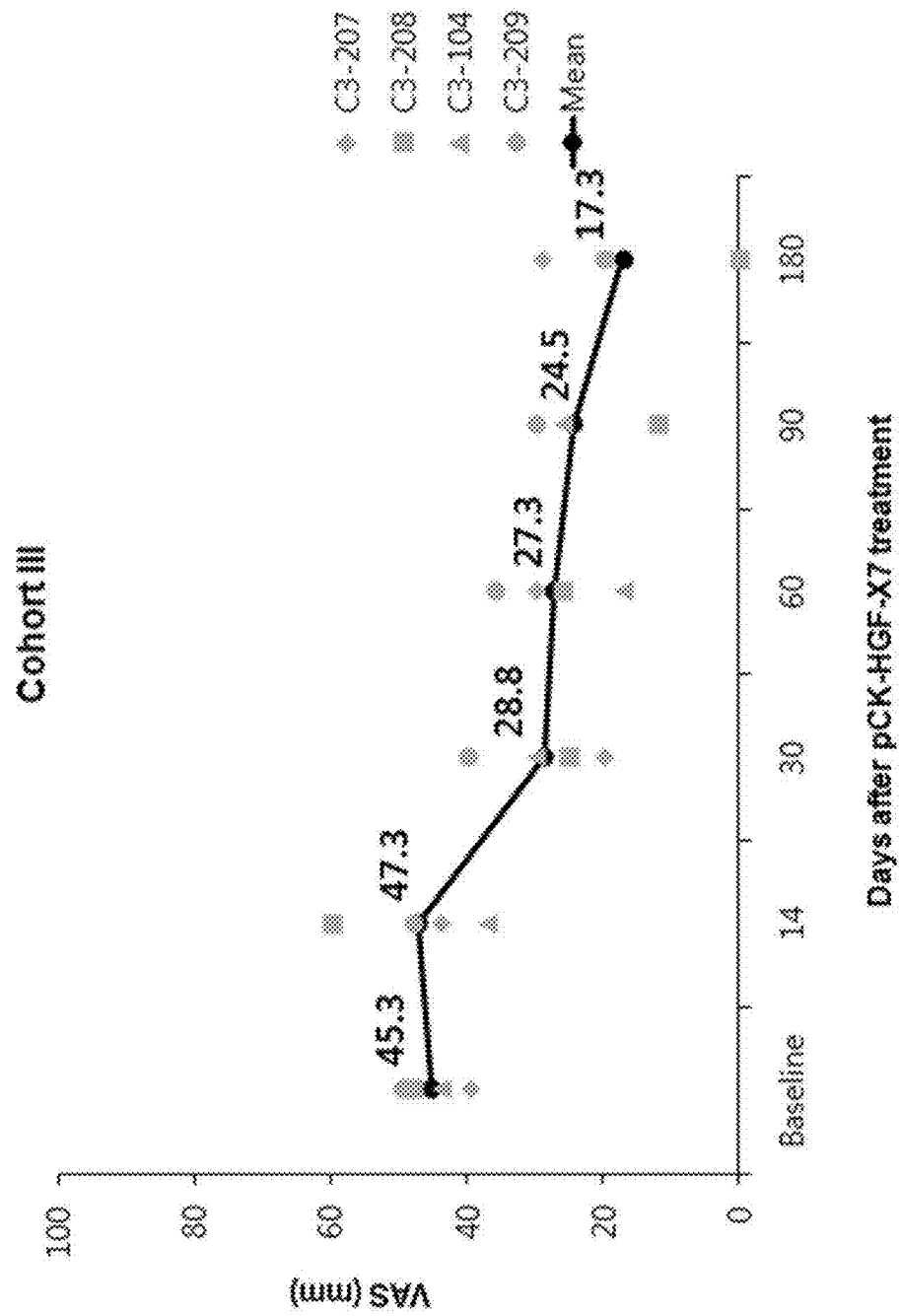
FIG. 19 shows results of efficacy of pCK-HGF-X7 in a third dose group (16 mg).

In the case of the third dose group (16 mg), the mean baseline VAS value was 45.3. Similarly to the second dose group, the VAS value from one month after treatment was sharply reduced and the mean VAS value at six months after treatment was 17.3, which showed a 61.4% reduction in the pain VAS value as compared with the baseline value. In the third dose group, the pain reduction was observed in all four subjects and the pain reduction of 50% or higher was observed in three of four subjects (FIG. 19).

Figure 20:
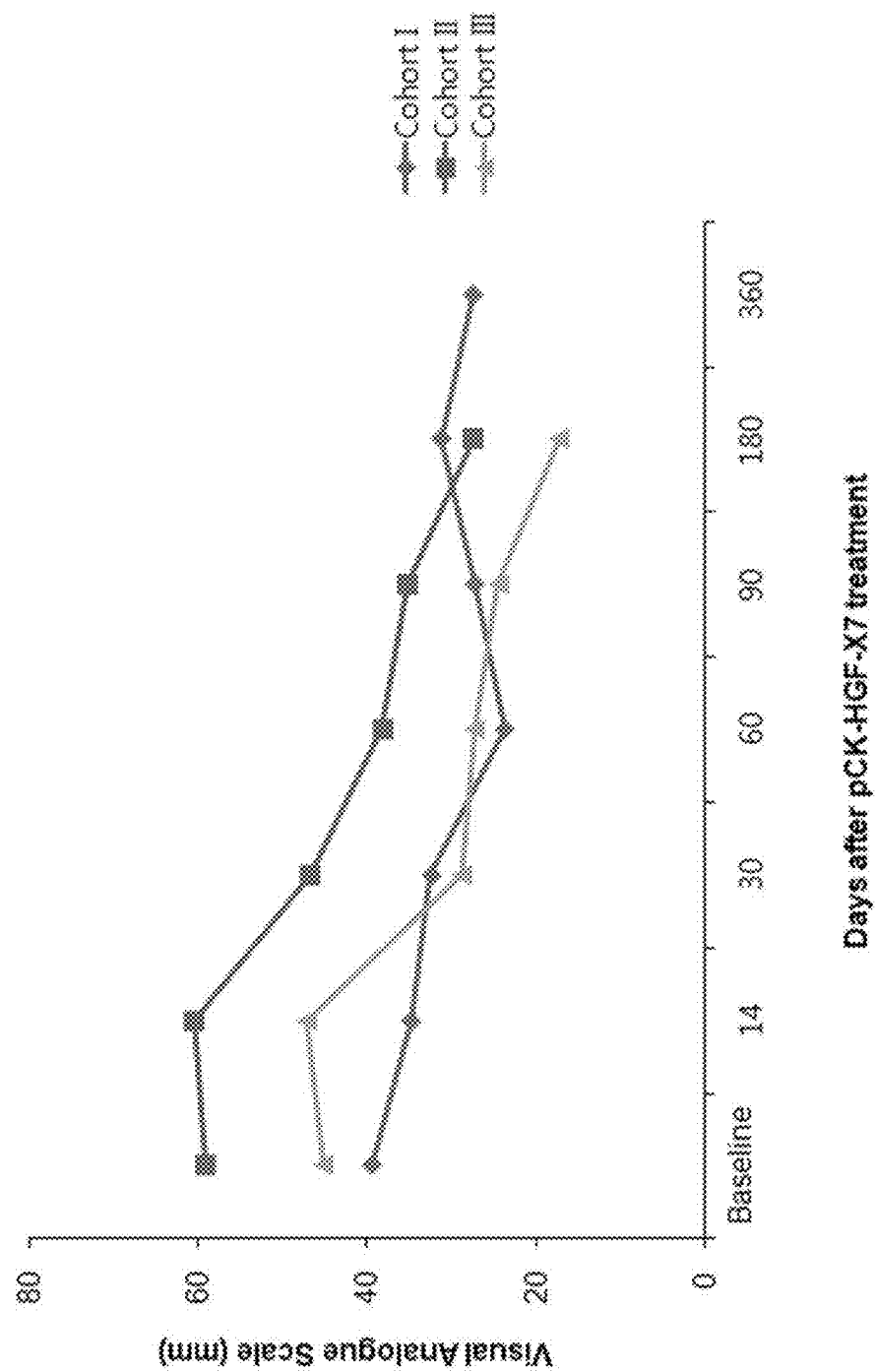
FIG. 20 shows the comparison of VAS among three dose groups (4 mg, 8 mg, and 16 mg).

As a result of surveying the efficacy using the pain VAS, the pain, which is the main symptom of diabetic neuropathy, was reduced after the pCK-HGF-X7 injection, and the pain reduction rate and the response rate to pain reduction were more remarkable in the medium-dose group (8 mg) or the high-dose group (16 mg) than in the low-dose group (4 mg). These results supported that the pain reduction observed in the present clinical trial was due to the administration of pCK-HGF-X7 and not the placebo effect (FIG. 20).

TABLE 2

| Trial group | Patient ID | Day 0 | | Day 14 | | Day 21 | Day 30 | Day 60 | Day 90 |
| | | Prior administration | Post administration | Prior administration | Post administration | | | | |
| --- | --- | --- | --- | --- | --- | --- | --- | --- | --- |
| I | 1-01 | NEG | 45846.3 | NEG | 62,762.8 | 10.0 | 7.1 | NEG | NEG |
| | 2-01 | NEG | 38401.5 | NEG | 18,215.9 | NEG | NEG | NEG | NEG |
| | 2-02 | NEG | 5871.8 | NEG | 38,401.5 | NEG | NEG | NEG | NEG |
| | 2-03 | NEG | 18215.9 | NEG | 5,871.8 | NEG | NEG | NEG | NEG |
| II | 2-04 | NEG | 562,669.0 | NEG | 300,852.0 | 51.0 | NEG | 38.1 | NEG |
| | 1-02 | NEG | 114,319.0 | 333.0 | 139,297.0 | 56,266.9 | 219.0 | 91.1 | NEG |
| | 2-05 | NEG | 183,514.0 | 63.0 | 582,978.0 | 3,875.0 | 69.0 | NEG | 28.9 |
| | 1-03 | 5.1 | 177,131.0 | 319.0 | 1,532,729.0 | 262.8 | 108.1 | NEG | NEG |
| III | 1-04 | NEG | 1,920,770.8 | 148 | 6,252,606.8 | 1,637.5 | 162.2 | NEG | 42.7 |
| | 2-07 | NEG | 368,173.0 | NEG | 23,198.3 | 32.9 | NEG | NEG | NEG |
| | 2-08 | NEG | 76,888.4 | 170.7 | 101,424.0 | 157.6 | 58.6 | 50.6 | NEG |
| | 2-09 | NEG | 491,690.2 | 77.1 | 432,454.6 | 77.6 | 33.7 | NEG | NEG |

(4) Efficacy Test Results

Figure 16:
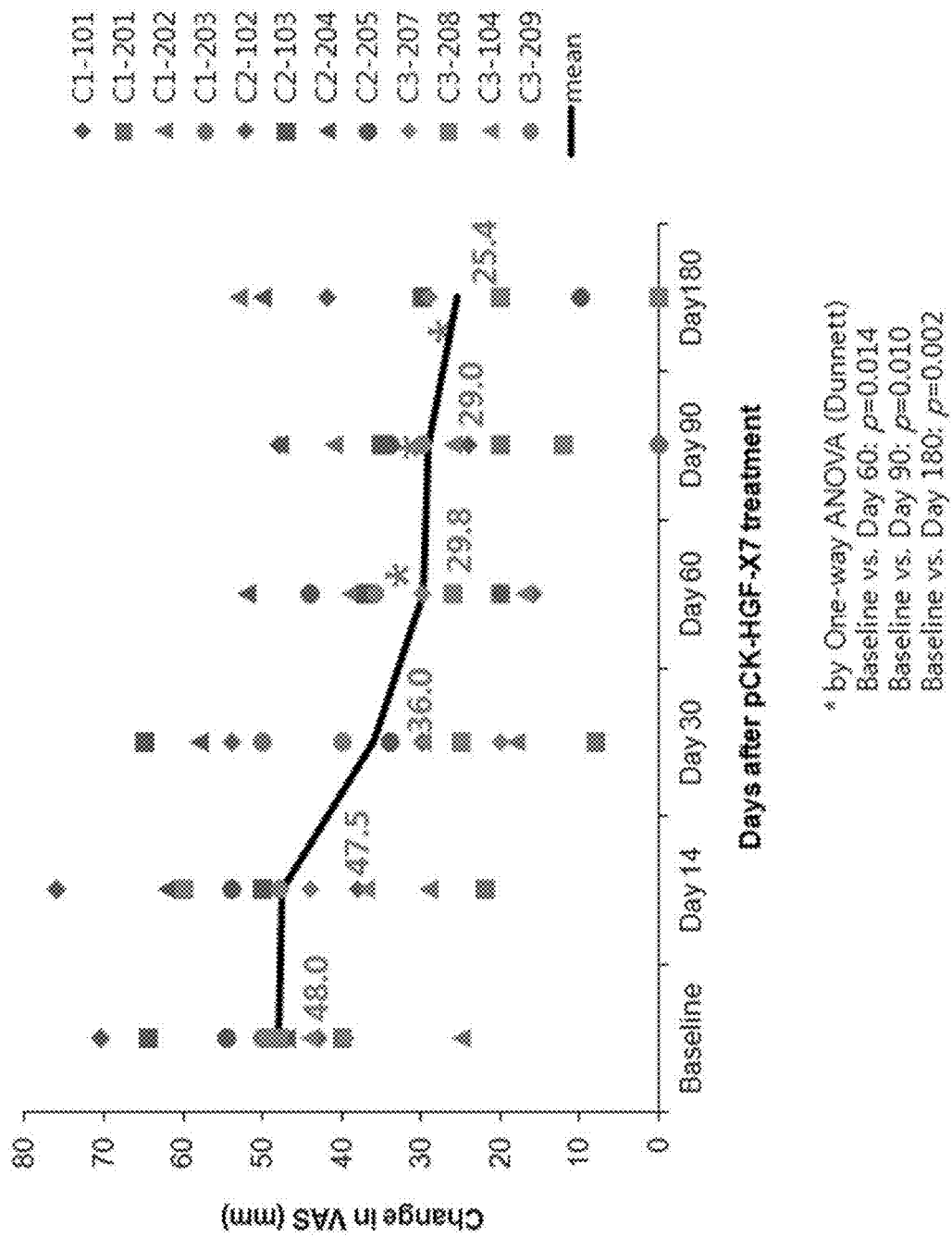
FIG. 16 shows results of efficacy of pCK-HGF-X7.

The severity of pain was measured through the Pain VAS (Visual Analogue Scale). As for a total of twelve subjects, the mean baseline VAS value was 48.0, and the mean VAS value at six months after the pCK-HGF-X7 treatment was 25.4, which showed a 47% reduction in the pain VAS value (FIG. 16).

Having described a preferred embodiment of the present invention, it is to be understood that variants and modifications thereof falling within the spirit of the invention may become apparent to those skilled in this art, and the scope of this invention is to be determined by appended claims and their equivalents.

The invention claimed is:

1. A method for treating a human subject having painful diabetic peripheral neuropathy, the method comprising:
intramuscularly administering to an affected limb of the human subject in need thereof, a pCK-HGF-X7 DNA construct at a dose of 8 mg per affected limb, equally divided into a plurality of injections to reduce pain in said human subject, wherein the pCK-HGF-X7 DNA construct comprises the nucleotide sequence as set forth in SEQ ID NO: 13, and
wherein each of the plurality of injections is performed with 0.25 mg of the pCK-HGF-X7 DNA construct.

2. The method of claim 1, wherein the step of intramuscularly administering to the affected limb is done at a dose of 8 mg, equally divided into 32 injections over two visits.

* * * * *